(12) United States Patent
Brennan et al.

(10) Patent No.: US 9,719,107 B2
(45) Date of Patent: Aug. 1, 2017

(54) CONSTRUCTION OF FULLY-DELETED ADENOVIRUS-BASED GENE DELIVERY VECTORS AND USES THEREOF

(71) Applicant: Isogenis, Inc., Aurora, CO (US)

(72) Inventors: Miles B. Brennan, Denver, CO (US);
Erin K. Spiegel, Aurora, CO (US);
Uwe D. Staerz, Denver, CO (US);
Charles Wall, Littleton, CO (US);
Janae Wheeler, Brighton, CO (US);
William J. Maslanik, Denver, CO (US); Xianghua Zhang, Auroroa, CO (US)

(73) Assignee: Isogenis, Inc., Aurora, CO (US)

( * ) Notice: Subject to any disclaimer, the term of this patent is extended or adjusted under 35 U.S.C. 154(b) by 0 days.

(21) Appl. No.: 14/921,421

(22) Filed: Oct. 23, 2015

(65) Prior Publication Data
US 2016/0168591 A1    Jun. 16, 2016

Related U.S. Application Data

(63) Continuation of application No. 14/494,991, filed on Sep. 24, 2014, now Pat. No. 9,169,493, which is a continuation of application No. 12/561,966, filed on Sep. 17, 2009, now Pat. No. 8,871,515.

(60) Provisional application No. 61/097,735, filed on Sep. 17, 2008, provisional application No. 61/143,281, filed on Jan. 8, 2009, provisional application No. 61/236,577, filed on Aug. 25, 2009.

(51) Int. Cl.
| C12N 5/00 | (2006.01) |
|---|---|
| C12N 15/86 | (2006.01) |
| C12N 7/00 | (2006.01) |

(52) U.S. Cl.
CPC .............. *C12N 15/86* (2013.01); *C12N 7/00* (2013.01); *C12N 2710/10043* (2013.01); *C12N 2710/10052* (2013.01); *C12N 2710/10343* (2013.01); *C12N 2710/10352* (2013.01)

(58) Field of Classification Search
None
See application file for complete search history.

(56) References Cited

U.S. PATENT DOCUMENTS

| 5,078,998 | A | 1/1992 | Bevan et al. |
|---|---|---|---|
| 5,242,687 | A | 9/1993 | Tykocinski et al. |
| 5,540,926 | A | 7/1996 | Aruffo et al. |
| 5,601,828 | A | 2/1997 | Tykocinski et al. |
| 5,623,056 | A | 4/1997 | Tykocinski et al. |
| 5,851,806 | A | 12/1998 | Kovesdi et al. |
| 6,060,054 | A | 5/2000 | Staerz |
| 6,156,497 | A | 12/2000 | Kaleko |
| 6,193,980 | B1 | 2/2001 | Efstathiou et al. |
| 6,207,456 | B1 | 3/2001 | Baru et al. |
| 6,264,950 | B1 | 7/2001 | Staerz |
| 6,303,379 | B1 | 10/2001 | Selden et al. |
| 6,509,150 | B1 | 1/2003 | Salvetti et al. |
| 6,525,029 | B1 | 2/2003 | Falck-Pedersen et al. |
| 6,544,506 | B2 | 4/2003 | Reisner |
| 7,026,121 | B1 | 4/2006 | Wohlgemuth et al. |
| 7,052,906 | B1 | 5/2006 | Lawson et al. |
| 7,235,358 | B2 | 6/2007 | Wohlgemuth et al. |
| 7,270,810 | B2 | 9/2007 | Reisner |
| 8,871,515 | B2 | 10/2014 | Brennan et al. |
| 9,169,493 | B2 | 10/2015 | Brennan et al. |
| 2002/0127205 | A1 | 9/2002 | Edge |
| 2003/0119192 | A1 | 6/2003 | Vogels et al. |
| 2005/0042217 | A1 | 2/2005 | Qi et al. |
| 2005/0118676 | A1 | 6/2005 | Qi et al. |
| 2009/0023196 | A1 | 1/2009 | Fallaux et al. |
| 2009/0053249 | A1 | 2/2009 | Qi et al. |

(Continued)

FOREIGN PATENT DOCUMENTS

| WO | WO 90/10285 | 9/1990 |
|---|---|---|
| WO | WO 90/10385 | 9/1990 |
| WO | WO 96/32140 | 10/1996 |

(Continued)

OTHER PUBLICATIONS

Kovesdi, Imre et al., "Adenoviral Producer Cells", 2010, Viruses, vol. 2: pp. 1681-1703.*
Parks, R., "Adenovirus Protein IX: A New Look at an Old Protein", 2005, Mol. Therapy, vol. 11: pp. 19-25.*
Akusjarvi, G., Proteins with transcription regulatory properties encoded by human adenoviruses. *Trends in Microbiology* 1(5): 163-170 (Aug. 1993).
Ali et al., Co-injection of adenovirus expressing CTLA4-Ig prolongs adenovirally mediated lacZ reporter gene expression in the mouse retina *Gene Therapy* 5(11): 1561-1565 (Nov. 1998).
Andrews et al., Evaluation of the duration of human factor VIII expression in nonhuman primates after systemic delivery of an adenoviral vector. *Human Gene Therapy* 13(11): 1331-6 (Jul. 20, 2002).
Andrews et al., Generation and characterization of E1/E2a/E3/E4-deficient adenoviral vectors encoding human factor VIII. *Molecular Therapy* 3(3): 329-36 (Mar. 2001).

(Continued)

*Primary Examiner* — Michael Burkhart
(74) *Attorney, Agent, or Firm* — Greenberg Traurig, LLP; Chinh H. Pham; Fang Xie

(57) ABSTRACT

The embodiments disclosed herein relate to the construction of fully-deleted Adenovirus-based gene delivery vectors packaged without helper Adenovirus, and more particularly to their use in gene therapy for gene and protein expression, vaccine development, and immunosuppressive therapy for allogeneic transplantation. In an embodiment, a method for propagating an adenoviral vector includes (a) providing an Adenovirus packaging cell line; (b) transfecting a fully-deleted Adenoviral vector construct into the cell line; and optionally (c) transfecting a packaging construct into the cell line, wherein the fully-deleted Adenoviral vector construct and optionally the packaging construct can transfect the Adenovirus packaging cell line resulting in the encapsidation of a fully-deleted Adenoviral vector independent of helper Adenovirus. In an embodiment, a target cell is transduced with the encapsidated fully-deleted Adenoviral vector for treating a condition, disease or a disorder.

25 Claims, 10 Drawing Sheets

(56) References Cited

U.S. PATENT DOCUMENTS

| | | |
|---|---|---|
| 2010/0120155 A1 | 5/2010 | Brennan et al. |
| 2015/0093831 A1* | 4/2015 | Brennan ................. C12N 7/00 435/456 |

FOREIGN PATENT DOCUMENTS

| | | |
|---|---|---|
| WO | WO 99/21576 | 5/1999 |
| WO | WO 99/23229 | 5/1999 |
| WO | WO 00/63406 | 10/2000 |
| WO | WO 02/102852 | 12/2002 |
| WO | WO 2004/042346 | 5/2004 |
| WO | WO 2004/083244 | 9/2004 |
| WO | WO 2004/083404 | 9/2004 |
| WO | WO 2006/003406 | 1/2006 |
| WO | WO 2006/012416 | 2/2006 |
| WO | WO 2010/033722 | 3/2010 |

OTHER PUBLICATIONS

Apostolopoulos, V. and Plebanski, M., The evolution of DNA vaccines. *Current Opinion in Molecular Therapeutics* 2(4): 441-7 (Aug. 2000).

Baim et al., A chimeric mammalian transactivator based on the lac repressor that is regulated by temperature and isopropyl beta-D-thiogalactopyranoside. *Proceedings of the National Academy of Sciences of the United States of America* 88(12): 5072-6 (Jun. 1991).

Baron et al., Tetracycline-controlled transcription in eukaryotes: novel transactivators with graded transactivation potential. *Nucleic Acids Research* 25(14): 2723-2729 (Jul. 15, 1997).

Batshaw et al, Recombinant adenovirus gene transfer in adults with partial ornithine transcarbamylase deficiency (OTCD). *Human Gene Therapy* 10(14): 2419-2437 (Sep. 20, 1999).

Bergelson et al., Isolation of a common receptor for Coxsackie B viruses and adenoviruses 2 and 5. *Science* 275(5304): 1320-3 (Feb. 28, 1997).

Bergmann et al., An endogenously synthesized decamer peptide efficiently primes cytotoxic T cells specific for the HIV-1 envelope glycoprotein. *European Journal of Immunology* 23(11): 2777-2781 (Dec. 8, 2005).

Bergmann et al., Flanking Residues Alter Antigenicity and Immunogenicity of Multi-Unit CTL Epitopes[1]. *The Journal of Immunology* 157 (8): 3242-3249 (Oct. 1996).

Berkner, K., Development of Adenovirus Vectors for the Expression of Heterologous Genes. *BioTechniques* 6 (7): 616-629 (Jul. 1, 1988).

Blacklow et al., Serologic evidence for human infection with adenovirus-associated viruses. *Journal of the National Cancer Institute* 40(2): 319-27 (Feb. 1968).

Blaese et al., T lymphocyte-directed gene therapy for ADA- SCID: initial trial results after 4 years. *Science* 270(5235): 475-80 (Oct. 20, 1995).

Blaese et al., Treatment of severe combined immunodeficiency disease (SCID) due to adenosine deaminase deficiency with CD34+ selected autologous peripheral blood cells transduced with a human ADA gene. *Human Gene Therapy* 4(4): 521-7 (Aug. 1993).

Bonyhadi et al., RevM10-Expressing T Cells Derived In Vivo from Transduced Human Hematopoietic Stem-Progenitor Cells Inhibit Human Immunodeficiency Virus Replication. *Journal of Virology* 71(6): 4707-4716 (Jun. 1997).

Bordignon et al., Transfer of the ADA gene into bone marrow cells and peripheral blood lymphocytes for the treatment of patients affected by ADA-deficient SCID. *Human Gene Therapy* 4(4): 513-20 (Aug. 1993).

Bristol et al., Adenovirus-mediated factor VIII gene expression results in attenuated anti-factor VIII-specific immunity in hemophilia a mice compared with factor VIII protein infusion. *Human Gene Therapy* 12(13): 1651-61 (Sep. 1, 2001).

Brown et al., Helper-dependent adenoviral vectors mediate therapeutic factor VIII expression for several months with minimal accompanying toxicity in a canine model of severe hemophilia A. *Blood* 103(3): 804-10 (Feb. 1, 2004).

Calos et al., Transposable elements. *Cell* 20(3): 579-95 (Jul. 1980).

Cavazzana-Calvo et al., Gene therapy of human severe combined immunodeficiency (SCID)-X1 disease. *Science* 288(5466): 669-72 (Apr. 28, 2000).

Chao et al., Induction of tolerance to human factor VIII in mice. *Blood* 97(10): 3311-2 (May 15, 2001).

Chinese Science Bulletin, 42(1):84-88 (Jan. 1997). (English Abstract attached).

Chirmule et al., Readministration of adenovirus vector in nonhuman primate lungs by blockade of CD40-CD40 ligand interactions. *Journal of Virology* 74(7): 3345-52 (Apr. 2000).

Choksi et al., A CD8 DE Loop Peptide Analog Prevents Graft-versus-Host Disease in a Multiple Minor Histocompatibility Antigen-Mismatched Bone Marrow Transplantation Model. *Biology of Blood and Marrow Transplantation* 10: 669-680 (Oct. 2004).

Chow et al., Complex Splicing Patterns of RNAs from the Early Regions of Adenovirus-2. *Journal of Molecular Biology* 134: 265-303 (May 1979).

Chroboczek et al., Adenovirus Fiber, *Current Topics in Microbiology and Immunology* 199, Pt. 1: 176-195 (1995).

Chuah et al., Clinical gene transfer studies for hemophilia A. *Seminars in Thrombosis and Hemostasis* 30(2): 249-56 (Apr. 2004).

Chuah et al., Therapeutic factor VIII levels and negligible toxicity in mouse and dog models of hemophilia A following gene therapy with high-capacity adenoviral vectors. *Blood* 101(5): 1734-43 (Mar. 1, 2003).

Chung et al., Molecular Diagnosis in Sepsis: From Bedside to Bench. J. *American College of Surgeons* 203(5): 585-598 (Nov. 2006).

Connolly et al., The Lyt-2 Molecule Recognizes Residues in the Class I a3 Domain in Allogeneic Cytotoxic T Cell Responses. *J. Exp. Med.* vol. 168: 325-341 (Jul. 1988).

Donahue et al., Ultrarapid, highly efficient viral gene transfer to the heart. *Proceedings of the National Academy of Sciences of the United States of America* 94: 4664-4668 (Apr. 1997).

Ebner et al., Comparative Sequence Analysis of the Hexon Gene in the Entire Spectrum of Human Adenovirus Serotypes: Phylogenetic, Taxonomic, and Clinical Implications. *Journal of Virology* 79 (20): 12635-12642 (Oct. 2005).

Fink P., et al., "Haplotype-specific suppression of cytoxic T cell induction by antigen inappropriately presented on T cells," *J. Exp. Med.* 157(1):141-154 (Jan. 1983).

Flint et al.,Viral transactivating proteins. *Annual Review of Genetics* 31: 177-212 (Dec. 1997).

Fontana et al., General Strategy for Broadening Adenovirus Tropism. *Journal of Virology* 77 (20): 11094-11104 (Oct. 2003).

Gaden et al., Gene transduction and cell entry pathway of fiber-modified adenovirus type 5 vectors carrying novel endocytic peptide ligands selected on humna tracheal glandular cells. *Journal of Virology* 78 (13): 7227-7247 (Jul. 2004).

Gaines, et al., pIRES-CD4t, a Dicistronic Expression Vector for MACS- or FACS-Based Selection of Transfected Cells, BioTechniques, 26:683-688 (Apr. 1999).

Game, D., et al., "Rejection Mechanisms in Transplantation", *Wien Klin. Wochenschr.* 113(20-21): 823-838 (Oct. 2001).

Gao et al., Molecular interactions of coreceptor CD8 and MHC class I: the molecular basis for functional coordination with the T-cell receptor. *Immunology Today* 21 (12): 630-636 (Dec. 2000).

Ge et al., Factors influencing the development of an anti-factor IX (FIX) immune response following administration of adeno-associated virus-FIX. *Blood Journal* 97(12): 3733-7 (Jun. 15, 2001).

Gorziglia et al., Elimination of both E1 and E2 from adenovirus vectors further improves prospects for in vivo human gene therapy. *Journal of Virology* 70(6): 4173-8 (Jun. 1996).

Gossen. al., Tight control of gene expression in mammalian cells by tetracycline-responsive promoters. *Proceedings of the National Academy of Sciences of the United States of America* 89(12): 5547-51 (Jun. 1992).

Gossen. et. al., Transcriptional Activation by Tetracyclines in Mammalian Cells. *Science* 268 (5218): 1766-1769 (Jun. 23, 1995).

(56) References Cited

OTHER PUBLICATIONS

Graham et al., Characteristics of a human cell line transformed by DNA from human adenovirus type 5, *Journal of General Virology* 36(1): 59-72 (Jul. 1977).
Grignani, et al., High-Efficiency Gene Transfer and Selection of Human Hematopoietic Progrenitor Cells with a Hybrid EBV/Retroviral Vector Expressing the Green Fluorescence Protein, 58:14-19 (Jan. 1, 1998).
Guangdong Pharmaceutical Journal, vol. 10, No. 5, pp. 1-5, Oct. 5, 2000 (English Abstract attached).
Hackett et al., Antivector and antitransgene host responses in gene therapy. *Current Opinion in Molecular Therapeutics* 2(4): 376-82 (2000).
Halbert et al., Transduction by adeno-associated virus vectors in the rabbit airway: efficiency, persistence, and readministration. *Journal of Virology* 71(8): 5932-41 (Aug. 1997).
Hambor et al., CD8 Functions as an Inhibitory Ligand in Mediating the Immunoregulatory Activity of CD8+ Cells, *Journal of Immunology*, 145(6):1646-1652 (Sep. 15, 1990).
Hambor et al., Regulation of Allogeneic Responses by Expression of CD8 a-chain of Stimulator Cells, *Int. Immunol.* 2(9):C3 (Sep. 1990).
Hammerschmidt, D., Development of a gutless vector. *The Journal of Laboratory and Clinical Medicine* 134(3): C3 (Sep. 1999).
Harui et al., Frequency and stability of chromosomal integration of adenovirus vectors. *Journal of Virology* 73(7): 6141-6 (Jul. 1999).
He et al., A simplified system for generating recombinant adenoviruses. *Proceedings of the National Academy of Sciences of the United States of America* 95(5): 2509-14 (Mar. 1998).
Heeger, P., T-Cell allorecognition and transplant rejection: A Summary and Update. *American Journal of Transplantation* 3: 525-533 (Jan. 2003).
Hernandez et al., Latent adeno-associated virus infection elicits humoral but not cell-mediated immune responses in a nonhuman primate model. *Journal of Virology* 73(10): 8549-58 (Oct. 1999).
Herzog et al., Immune implications of gene therapy for hemophilia. *Seminars in Thrombosis and Hemostasis* 30(2): 215-26 (Apr. 2004).
Hillgenberg et al., Chromosomal integration pattern of a helper-dependent minimal adenovirus vector with a selectable marker inserted into a 27.4-kilobase genomic stuffer. *Journal of Virology* 75(20): 9896-9908 (Oct. 2001).
Hodges et al., The spf$^{ash}$ mouse: a missense mutation in the ornithine transcarbamylase gene also causes aberrant mRNA splicing. *Proceedings of the National Academy of Sciences of the United States of America* 86(11): 4142-6 (Jun. 1989).
Hofmann et al., Ovine adenovirus vectors overcome preexisting humoral immunity against human adenoviruses in vivo. *Journal of Virology* 73(8): 6930-6 (Aug. 1999).
Hong et al., Enhancement of Adenovirus-Mediated Gene Delivery by Use of an Oligopeptide with Dual Binding Specificity. *Human Gene Therapy* 10: 2577-2586 (Nov. 1, 1999).
Jaeken et al., An infantile autistic syndrome characterised by the presence of succinylpurines in body fluids. *The Lancet* 2(8411): 1058-61 (Nov. 10, 1984).
Jaffe et al., Adenoviral Mediated Transfer and Expression of a Normal Human a1Antitrypsin cDNA in Primary Rat Hepatocytes. *Clinical Research* 39 (2): 302A (May 1991).
Johnson-Saliba et al., Gene Therapy: Optimising DNA Delivery to the Nucleus. *Current Drug Targets*, vol. 2: 371-399 (Dec. 2001).
Jooss et al., Blunting of immune responses to adenoviral vectors in mouse liver and lung with CTLA4Ig. *Gene Therapy* 5(3): 309-319 (Mar. 1998).
Kaplan, D., et al., "An Immunoregulatory function for the CD8 molecule," *Proc. Natl. Acad. Sci. USA* 86(21):8512-8515 (Nov. 1989).
Kern et al., Expression, Purification, and Functional Analysis of Murine Ectodomain Fragments of CD8αα and CD8αβ Dimers. *Journal of Bio. Chemistry* 274 (38): 27237-27243 (Sep. 17, 1999).

Kern, et al., Structural Basis of CD8 Coreceptor Function Revealed by Crystallographic Analysis of a Murine CD8aa Ectodomain Fragment in Complex with H-2K$^b$, *Immunity* 9(4): 519-530 (Oct. 1998).
Kleckner et al., Mutagenesis by insertion of a drug-resistance element carrying an inverted repetition. *Journal of Molecular Biology* 97(4): 561-75 (Oct. 5, 1975).
Krasnykh et al., Generation of Recombinant Adenovirus Vectors with Modified Fibers for Altering Viral Tropism. *Journal of Virology* 70(10):6839-6846 (Oct. 1996).
Krieger et al., CD4+ but not CD8+ Cells Are Essential for Allorejection. *J. Exp. Med.* vol. 184: 2013-2018 (Aug. 1996).
Leahy, D., A Structural View of CD4 and CD8. *The FASEB Journal* 9: 17-25 (Jan. 1995).
Leahy et al., Crystal Structure of a Soluble Form of the Human T Cell Coreceptor CD8 at 2.6 A Resolution. *Cell* 68(6): 1145-1162 (Mar. 20, 1992).
Lee et al., Glucocorticoids selectively inhibit the transcription of the interleukin 1 beta gene and decrease the stability of interleukin 1 beta mRNA. *Proceedings of the National Academy of Sciences of the United States of America* 85(4): 1204-8 (Feb. 1988).
Liang et al., Monitoring Adenoviral DNA Delivery, Using a Mutant Herpes Simplex Virus Type 1 Thymidine Kinase Gene as a PET Reporter Gene. *Gene Therapy* 9(24): 1659-1666, (Dec. 2002).
Liebermann, H et al., Mapping of Linear Epitopes on Fibre Knob of Human Adenovirus Serotype 5. *Virus Research* 73 (2): 145-151 (Mar. 2001).
Louis et al., Cloning and sequencing of the cellular-viral junctions from the human adenovirus type 5 transformed 293 cell line. *Virology* 233(2): 423-9 (Jul. 7, 1997).
Lozier et al., Adenovirus-mediated expression of human coagulation factor IX in the rhesus macaque is associated with dose-limiting toxicity. *Blood* 94(12): 3968-75 (Dec. 15, 1999).
Lu et al., Complete correction of hemophilia A with adeno- associated viral vectors containing a full-size expression cassette. *Human Gene Therapy* 19(6): 648-54 (Jun. 2008).
Mah et al., Dual vectors expressing murine factor VIII result in sustained correction of hemophilia A mice. *Human Gene Therapy* 14(2): 143-52 (Jan. 20, 2003).
Martin, P., Donor CD8 Cells Prevent Allogeneic Marrow Graft Rejection in Mice: Potential Implications for Marrow Transplantation in Humans. *J. Exp. Med.* vol. 178: 703-712 (Aug. 1993).
Mayo, D., Differentiation of herpes simplex virus types 1 and 2 by sensitivity to (E)-5-(2-bromovinyl)-2'—deoxyuridine. *Journal of Clinical Microbiology* 15(4): 733-6 (Apr. 1982).
McKelvey et al., T-cell response to adenovirus hexon and DNA-binding protein in mice. *Gene Therapy* 11(9): 791-6 (Feb. 12, 2004).
Miller et al., Chromosomal effects of adeno-associated virus vector integration. *Nature Genetics* 30(2): 147-8 (Feb. 2002).
Moffatt et al., Circumvention of vector-specific neutralizing antibody response by alternating use of human and non-human adenoviruses: implications in gene therapy. *Virology* 272(1): 159-67 (Jun. 20, 2000).
Moscioni et al., Long-term correction of ammonia metabolism and prolonged survival in ornithine transcarbamylase-deficient mice following liver-directed treatment with adeno-associated viral vectors. *Molecular Therapy* 14(1): 25-33 (Jul. 2006).
Moskalenko et al., Epitope mapping of human anti-adeno-associated virus type 2 neutralizing antibodies: implications for gene therapy and virus structure. *Journal of Virology* 74(4): 1761-6 (Feb. 2000).
Murphy et al., Gene therapy for haemophilia. *British Journal of Haematology* 140(5): 479-87 (Mar. 2008).
Muruve et al., Helper-dependent adenovirus vectors elicit intact innate but attenuated adaptive host immune responses in vivo. *Journal of Virology* 78(11): 5966-72 (Jun. 2004).
Nagel et al., The xvβ5 Integrin of Hematopoietic and Nonhematopoietic cells is a transduction Receptor of RGD-4C Fiber-Modified Adenoviruses. *Gene Therapy* 10: 1643-1653 (Jan. 2003).
Nicol et al., Effect of Adenovirus Serotype 5 Fiber and Penton Modifications on in Vivo Tropism in Rats. *Molecular Therapy* 10(2): 344-354 (Aug. 2004).

(56) References Cited

OTHER PUBLICATIONS

Othman et al., Adenovirus-induced thrombocytopenia: the role of von Willebrand factor and P-selectin in mediating accelerated platelet clearance. *Blood* 109(7): 2832-9 (Apr. 1, 2007).
Palmer et al., Helper-dependent adenoviral vectors for gene therapy. *Human Gene Therapy* 16(1): 1-16 (Jan. 2005).
Parks et al., A helper dependent adenoviral vector system: Removal of the helper virus by Cre-mediated excision of the viral packaging signal. *Proceedings of the National Academy of Sciences of the United States of America* 93(24): 13565-13570 (Nov. 1996).
Parks et al., Effects of stuffer DNA on transgene expression from helper-dependent adenovirus vectors. *Journal of Virology* 73(10): 8027-34 (Oct. 1999).
Peng et al., Inhibition of Tumor Necrosis Factor Alpha by an Adenovirus-Encoded Soluble Fusion Protein Extends Transgene Expression in the Liver and Lung, Journal of Virology, 73(6):5098-5109 (Jun. 1999).
Pfeifer et al., Gene Therapy: Promises and Problems. *Annu. Rev. Genomics Hum. Genet.* 2: 177-211 (Sep. 2001).
Piedra et al., Incidence and prevalence of neutralizing antibodies to the common adenoviruses in children with cystic fibrosis: implication for gene therapy with adenovirus vectors. *Pediatrics* 101(6): 1013-9 (Jun. 1998).
Postle et al., Nucleotide sequence of the repressor gene of the TN10 tetracycline resistance determinant. *Nucleic Acids Research* 12(12): 4849-63 (Jun. 25, 1984).
Potter, et al., Substitution at Residue 227 of H-2 Class I Molecules Abrogates Recognition by CD7-Dependent but not CD8-Independent, Cytotoxic T Lymphocytes. *Nature* 337 (6202): 73-75 (Jan. 5, 1989).
Qi et al., Hybrid Antibody Mediated Veto of Cytotoxic T Lymphocyte Responses. *J. Exp. Med.* 183: 1973-1980 (May 1996).
Rammensee, et al. Class I Restricted Interaction between Suppressor and Cytolytic Cells in the Response to Minor Histocompatibility Antigens, *Journal of Immunology*, 132(2): 668-672 (Feb. 1984).
Rammensee, et al. Suppression of Cell-mediated Lymphocytoxicity against Minor Histocompatibility Antigens Mediated by Lyt-1+ and Lyt-2+ T Cells of Stimulator Strain Origin, *European Journal of Immunology*, 12(11): 930-934 (Nov. 1982).
Raper et al., A pilot study of in vivo liver-directed gene transfer with an adenoviral vector in partial ornithine transcarbamylase deficiency. *Human Gene Therapy* 13(1): 163-75 (Jan. 1, 2002).
Raper et al., Fatal systemic inflammatory response syndrome in a ornithine transcarbamylase deficient patient following adenoviral gene transfer. *Molecular Genetics and Metabolism* 80(1-2): 148-58 (Sep. 2003).
Reich-Zeliger et al., Anti-Third Party CD8+ CTLs as Potent Veto Cells: Coexpression of CD8 and FasL is a Prerequisite. *Immunity* 13: 507-515 (Oct. 2000).
Rosenfeld et al., Adenovirus-Mediated Transfer of a Recombinant a1-Antitrypsin Gene to the Lung Epithelium in Vivo. *Science*, New Series 252 (5004): 431-434 (Apr. 19, 1991).
Rosenfeld et al., In Vivo Transfer of the Human Cystic Fibrosis Gene to the Respiratory Epithelium: Biology of Epithelial Cells Featured Research Symposium. *Clinical Research* 39 (2) (May 1991).
Roth et al., Helper-dependent adenoviral vectors efficiently express transgenes in human dendritic cells but still stimulate antiviral immune responses. *Journal of Immunology* 169(8): 4651-6 (Oct. 15, 2002).
Sadowski et al., GAL4-VP16 is an unusually potent transcriptional activator. *Nature* 335(6190): 563-4 (Oct. 6, 1988).
Salter et al., A Binding Site for the T-Cell Co-Receptor CD8 on the $\alpha_3$ Domain of HLA-A2. *Nature*, 345: 41-46 (May 3, 1990).
Sambhara, S., et al., Programmed Cell Death of T Cells Signaled by th eT Cell Receptor and the a-3 Domain if Class I MHC, *Science*, 252 (5011):1424-1427 (Jun. 7, 1991).
Sarkar et al., Long-term efficacy of adeno-associated virus serotypes 8 and 9 in hemophilia a dogs and mice. *Human Gene Therapy* 17(4): 427-39 (Apr. 2006).

Sarkar et al., Partial correction of murine hemophilia A with neo-antigenic murine factor VIII. *Human Gene Therapy* 11(6): 881-94 (Apr. 10, 2000).
Seipel et al., Different activation domains stimulate transcription from remote ('enhancer') and proximal ('promoter') positions. *The EMBO Journal* 11(13): 4961-8 (Dec. 1992).
Sewell et al., Antagonism of Cytotoxic T-Lymphocyte Activation by Soluble CD8. *Nature Medicine* 5(4): 399-404 (Apr. 1999).
Shiue et al., A Second Chain of Human CD8 is Expressed on Peripheral Blood Lymphocytes. *Journal of Experimental Medicine* 168:1993-2005 (Dec. 1, 1988).
Shoji et al., Current Status of Delivery Systems to Improve Target Efficacy of Oligonucleotides. *Current Pharmaceutical Design* 10 (7): 785-796 (Mar. 2004).
Staerz, U., et al., Treatment of an Autoimmune Disease with 'Classical' T cell Veto: A Proposal, J. Clin. Immunol. 19(4):195-202 (Jul. 1999).
Stevenson et al., Human Adenovirus Serotypes 3 and 5 Bind to Two Different Cellular Receptors via the Fiber Head Domain. *Journal of Virology*, 69 (5): 2850-2857 (May 1995).
Stoilova-McPhie et al., 3-Dimensional structure of membrane-bound coagulation factor VIII: modeling of the factor VIII heterodimer within a 3-dimensional density map derived by electron crystallography. *Blood* 99 (4): 1215-23 (Feb. 15, 2002).
Suhrbier, A., Multi-Epitope DNA Vaccines. *Immunology and Cell Biology* 75: 402-408 (Apr. 17, 1997).
Trepel et al., Molecular Adaptors for Vascular-Targeted Adenoviral Gene Delivery. *Human Gene Therapy* 11: 1971-1981 (Sep. 20, 2000).
Uchida et al., Co-administration of adenovirus vector expressing CTLA4-Ig prolongs transgene expression in the brain of mice sensitized with adenovirus. *Brain Research* 898(2): 272-80 (Apr. 20, 2001).
Verma et al., Gene Therapy—Promises, Problems and Prospects. *Nature* 389: 239-242 (Sep. 18, 1997).
Weiss et al., Prevention and Treatment of Graft-Versus-Host Disease by Down-Regulation of Anti-Host Reactivity with Veto Cells of Host Origin. *Bone Marrow Transplantation* 23 (11): 1139-1143 (Jun. 1999).
Woodle, E., et al., Anti-human Class I MHC Antibodies Induce Apoptosis by a Pathway that is Distinct from the Fas Antigen-mediated Pathway, *Journal of Immunology* 158(5): 2156-2164 (Mar. 1997).
Wu et al., Construction and Characterization of Adenovirus Serotype 5 Packaged by Serotype 3 Hexon. *Journal of Virology* 76 (24): 12775-12782 (Dec. 2002).
Xiong et al., Regulatable gutless adenovirus vectors sustain inducible transgene expression in the brain in the presence of an immune response against adenoviruses. *Journal of Virology* 80(1): 27-37 (Jan. 2006).
Yang et al., Cellular immunity to viral antigens limits E1-deleted adenoviruses for gene therapy. *Proceedings of the National Academy of Sciences of the United States of America* 91(10): 4407-11 (May 1994).
Yang et al., Role of viral antigens in destructive cellular immune responses to adenovirus vector-transduced cells in mouse lungs. *Journal of Virology* 70(10): 7209-12 (Oct. 1996).
Ye et al., Transient depletion of CD4 lymphocyte improves efficacy of repeated administration of recombinant adenovirus in the ornithine transcarbamylase deficient sparse fur mouse. *Gene Therapy* 7(20): 1761-7 (Oct. 2000).
Yoshida et al., Generation of Fiber-Mutant Recombinant Adenoviruses for Gene Therapy of Malignant Glioma. *Human Gene Therapy* 9: 2503-2515 (Nov. 20, 1998).
Zerby et al., In vivo ligand-inducible regulation of gene expression in a gutless adenoviral vector system. *Human Gene Therapy* 14(8): 749-61 (May 20, 2003).
Zhang, P., et al., Transfer of activation-dependent gene expression into T cell lines by recombinant adeno-associated virus. *Gene Therapy* 6(2): 182-9 (Feb. 1999).

(56) References Cited

OTHER PUBLICATIONS

Zhang, Y., et al., CD40 ligand-dependent activation of cytotoxic T lymphocytes by adeno-associated virus vectors in vivo: role of immature dendritic cells. *Journal of Virology* 74(17): 8003-10 (Sep. 2000).

Zimmer et al., Efficient Mitochondrial Import of Newly Synthesized Ornithine Transcarbmylase (OTC) and Correction of Secondary Metabolic Alterations in spfash Mice Following Gene Therapy of OTC Deficiency. *Molecular Medicine* 5: 244-253 (Apr. 1999).

Office Action cited in U.S. Appl. No. 10/804,762 mailed May 2, 2006.

Office Action cited in U.S. Appl. No. 10/804,762 mailed Nov. 30, 2006.

Office Action cited in U.S. Appl. No. 10/804,762 mailed Aug. 23, 2007.

Office Action cited in U.S. Appl. No. 10/804,762 mailed May 14, 2008.

Office Action cited in U.S. Appl. No. 10/804,762 mailed May 11, 2009.

Office Action cited in U.S. Appl. No. 10/804,763 mailed Sep. 7, 2006.

Office Action cited in U.S. Appl. No. 10/804,763 mailed Feb. 13, 2008.

Office Action cited in U.S. Appl. No. 10/804,763 mailed Nov. 4, 2008.

Office Action cited in U.S. Appl. No. 10/804,763 mailed Jun. 3, 2009.

Office Action cited in U.S. Appl. No. 10/804,763 mailed Mar. 23, 2011.

International Search Report based on PCT/US2004/008567 mailed Nov. 11, 2004.

International Search Report based on PCT/US2004/008574 mailed Jun. 9, 2004.

International Search Report based on PCT/US2005/025878 mailed May 17, 2006.

Cheshenko et al., "A novel system for the production of fully deleted adenovirus vectors that does not require helper adenovirus," Gene Therapy. 36: 59-72 (2001).

Cheshenko et al., "A novel system for the production of fully deleted adenovirus vectors that does not require helper adenovirus" Gene Therapy. 8: 846-854 (2001).

Graham and Prevec, "Manipulation of Adenovirus Vectors." Methods in Molecular Biology. 7: 109-128 (1991).

Jogler et al., "Replication properties of human adenovirus in vivo and in cultures of primary cells from different animal species," Journal of Virology. 80(7): 3546-3558 (2006).

Krougliak and Graham, "Development of cell lines capable of complementing E1, E4, and protein IX defective adenovirus Type 5 mutants," Human Gene Therapy. 6: 1575-1586 (1995).

Vellinga et al., "A system for efficient generation of adenovirus protein IX-producing helper cell lines," The Journal of Gene Medicine. 8: 147-154 (2005).

International Search Report based on PCT/US09/57344 mailed on Oct. 24, 2011.

Alba et al., "Gutless adenovirus: last-generation adenovirus for gene therapy," Gene Therapy. 12: S18-S27 (2005).

Bertera et al., "Gene transfer of manganese superoxide dismutase extends islet graft Function in a mouse model of autoimmune diabetes," Diabetes. 52: 387-393 (2003).

Catalucci et al., "An adenovirus type 5 (Ad5) amplicon-based packaging cell line for production of high-capacity helper-independent $\Delta$E1-E2-E3-E4 Ad5 Vectors," Journal of Virology. 79(10): 6400-6409 (2005).

Rang and Will. "The tetracycline-responsive promoter contains functional interferon-inducible response elements," Nucleic Acids Research. 28(5): 1120-1125 (2000).

Norkin, Leonard, "Virology. Molecular Biology and Pathogenesis," ASM Press, Washington, DC. 452-454 (2010).

Supplemental European Search Report issued in European Application No. 09815212.7 dated Sep. 19, 2012.

U.S. Appl. No. 12/561,966, filed Sep. 17, 2009, Construction of Fully-Deleted Adenovirus-Based Gene Delivery Vectors and Uses Thereof.

U.S. Appl. No. 14/494,991, filed Sep. 24, 2014, Construction of Fully-Deleted.

\* cited by examiner

SEQUENCE LISTING

```
<160> NUMBER OF SEQ ID NOS: 24

<210> SEQ ID NO 1
<211> LENGTH: 126
<212> TYPE: DNA
<213> ORGANISM: Artificial Sequence
<220> FEATURE:
<223> OTHER INFORMATION: Multiple Cloning Site

<400> SEQUENCE: 1
agctaactat cccattaatt aaccgtccat tttcgaaaat gctacccggg aatacgttac      60
gtatgaatct ggcgcgccta acgtaggatc caatgctaac tagtataaga tatttaaata     120
agccca                                                                126

<210> SEQ ID NO 2
<211> LENGTH: 126
<212> TYPE: DNA
<213> ORGANISM: Artificial Sequence
<220> FEATURE:
<223> OTHER INFORMATION: Multiple Cloning Site

<400> SEQUENCE: 2
tcgatgggct tatttaaata tcttatacta gttagcattg gatcctacgt taggcgcgcc      60
agattcatac gtaacgtatt cccgggtagc attttcgaaa atggacggtt aattaatggg     120
atagtt                                                                126

<210> SEQ ID NO 3
<211> LENGTH: 30
<212> TYPE: DNA
<213> ORGANISM: Artificial Sequence
<220> FEATURE:
<223> OTHER INFORMATION: Multiple Cloning Site

<400> SEQUENCE: 3
```
gatccctacg gtacctacgt ctagacagtg                                30

<210> SEQ ID NO 4
<211> LENGTH: 30
<212> TYPE: DNA
<213> ORGANISM: Artificial Sequence
<220> FEATURE:
<223> OTHER INFORMATION: Multiple Cloning Site

<400> SEQUENCE: 4
aattcactgt ctagacgtag gtaccgtagg                                30

<210> SEQ ID NO 5
<211> LENGTH: 32
<212> TYPE: DNA
<213> ORGANISM: Artificial Sequence
<220> FEATURE:
<223> OTHER INFORMATION: Primer

<400> SEQUENCE: 5
ggtacctgta tccggtgcac ttgggaaatt tg                             32

<210> SEQ ID NO 6
<211> LENGTH: 31
<212> TYPE: DNA
<213> ORGANISM: Artificial Sequence
<220> FEATURE:
<223> OTHER INFORMATION: Primer

<400> SEQUENCE: 6
tctagaacac catggtcaaa tgctacctgg g                              31

<210> SEQ ID NO 7
<211> LENGTH: 62
<212> TYPE: DNA
<213> ORGANISM: Artificial Sequence
<220> FEATURE:
<223> OTHER INFORMATION: Primer

<400> SEQUENCE: 7
aatacccggg aatatgagct catcatgttt aaacaatcat catcaataat atacctattt    60
tg                                                              62

<210> SEQ ID NO 8
<211> LENGTH: 37
<212> TYPE: DNA
<213> ORGANISM: Artificial Sequence
<220> FEATURE:
<223> OTHER INFORMATION: Primer

<400> SEQUENCE: 8
acatatctag aaacagtctc cacgtaaacg gtcaaag                        37

<210> SEQ ID NO 9
<211> LENGTH: 52
<212> TYPE: DNA
<213> ORGANISM: Artificial Sequence
<220> FEATURE:
<223> OTHER INFORMATION: Primer

<400> SEQUENCE: 9
taacatgcat aatatgcccg ggcatagcgg cagcctaaca gtcagcctta cc        52

<210> SEQ ID NO 10
<211> LENGTH: 50

<212> TYPE: DNA
<213> ORGANISM: Artificial Sequence
<220> FEATURE:
<223> OTHER INFORMATION: Primer

<400> SEQUENCE: 10
aatgggccca tatagtttaa acatacatca tcaataatat acctattttg     50

<210> SEQ ID NO 11
<211> LENGTH: 28
<212> TYPE: DNA
<213> ORGANISM: Artificial Sequence
<220> FEATURE:
<223> OTHER INFORMATION: Primer

<400> SEQUENCE: 11
ataagcttga acatacacaa cagttagg     28

<210> SEQ ID NO 12
<211> LENGTH: 28
<212> TYPE: DNA
<213> ORGANISM: Artificial Sequence
<220> FEATURE:
<223> OTHER INFORMATION: Primer

<400> SEQUENCE: 12
ataagctttc tggcagcaac ttcataac     28

<210> SEQ ID NO 13
<211> LENGTH: 29
<212> TYPE: DNA
<213> ORGANISM: Artificial Sequence
<220> FEATURE:
<223> OTHER INFORMATION: Primer

<400> SEQUENCE: 13
ttatcgatga tgaagatttg ataaagtgg     29

<210> SEQ ID NO 14
<211> LENGTH: 31
<212> TYPE: DNA
<213> ORGANISM: Artificial Sequence
<220> FEATURE:
<223> OTHER INFORMATION: Primer

<400> SEQUENCE: 14
ttggcgcgcc gttatcctca aagtttcagg c     31

<210> SEQ ID NO 15
<211> LENGTH: 30
<212> TYPE: DNA
<213> ORGANISM: Artificial Sequence
<220> FEATURE:
<223> OTHER INFORMATION: Primer

<400> SEQUENCE: 15
ctgtcgacaa atgaatccaa accaaaagat     30

<210> SEQ ID NO 16
<211> LENGTH: 31
<212> TYPE: DNA
<213> ORGANISM: Artificial Sequence
<220> FEATURE:
<223> OTHER INFORMATION: Primer

<400> SEQUENCE: 16
tcgaagctta gttacttgtc aatggtaaat g                                              31

<210> SEQ ID NO 17
<211> LENGTH: 46
<212> TYPE: DNA
<213> ORGANISM: Artificial Sequence
<220> FEATURE:
<223> OTHER INFORMATION: Primer

<400> SEQUENCE: 17
aatactcgag ataatgaatt catatcgccc aggtgttttt ctcagg                              46

<210> SEQ ID NO 18
<211> LENGTH: 45
<212> TYPE: DNA
<213> ORGANISM: Artificial Sequence
<220> FEATURE:
<223> OTHER INFORMATION: Primer

<400> SEQUENCE: 18
aataggatcc ataatgaatt catagatcca aatccaaaca gagtc                               45

<210> SEQ ID NO 19
<211> LENGTH: 23
<212> TYPE: DNA
<213> ORGANISM: Artificial Sequence
<220> FEATURE:
<223> OTHER INFORMATION: Primer

<400> SEQUENCE: 19
atgagacata ttatctgcca cgg                                                       23

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
ttatggcctg gggcgtttac ag                                                        22

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
atgagcacca actcgtttga tg                                                        22

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
ttaaaccgca ttgggagggg                                                           20

<210> SEQ ID NO 23
<211> LENGTH: 21
<212> TYPE: DNA
<213> ORGANISM: Artificial Sequence -continued

```
<220> FEATURE:
<223> OTHER INFORMATION: Primer

<400> SEQUENCE: 23
cgcgttacat aacttacggt a                                                    21

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
ccagggaaga ctttatcatc                                                      20
```

CONSTRUCTION OF FULLY-DELETED ADENOVIRUS-BASED GENE DELIVERY VECTORS AND USES THEREOF

RELATED APPLICATIONS

This application is a continuation of U.S. application Ser. No. 14/494,991, filed Sep. 24, 2014, which is a continuation of U.S. application Ser. No. 12/561,966, filed Sep. 17, 2009, now U.S. Pat. No. 8,871,515, which claims the benefit of and priority to U.S. Provisional Application No. 61/097,735, filed Sep. 17, 2008, U.S. Provisional Application No. 61/143,281, filed Jan. 8, 2009, and U.S. Provisional Application No. 61/236,577, filed Aug. 25, 2009, the entirety of each of which applications is hereby incorporated herein by reference.

FIELD

The embodiments disclosed herein relate to the construction of fully-deleted Adenovirus-based gene delivery vectors packaged without helper Adenovirus, and more particularly to their use in gene therapy for gene and protein expression, vaccine development and immunosuppressive therapy.

BACKGROUND

Adenoviruses

Among the most commonly used vectors for the delivery of genetic material into human cells are the Adenoviruses. Adenoviruses have been isolated from a large number of different species, and more than 100 different serotypes have been reported. The overall organization of the Adenoviral genome is conserved among serotypes, such that specific functions are similarly positioned. The Ad2 and Ad5 genomes have been completely sequenced and sequences of selected regions of genomes from other serotypes are available. Most adults have been exposed to the Adenovirus serotypes most commonly used in gene therapy (serotypes 2 and 5).

The Ad5 genome is a linear, non-segmented, double stranded DNA, approximately 34-43 kbp (size varies from group to group) which has the theoretical capacity to encode 30-40 genes. The Ad5 genome is flanked on both sides by inverted terminal repeat sequences (LITR and RITR), which are essential to replication of Adenoviruses. The virus infectious cycle is divided into an early and a late phase. In the early phase, the virus is uncoated and the genome transported to the nucleus, after which the early gene regions E1-E4 become transcriptionally active.

The early region-1 (E1) contains two transcription regions named E1A and E1B. The E1A region (sometimes referred to as immediate early region) encodes two major proteins that are involved in modification of the host-cell cycle and activation of the other viral transcription regions. The E1B region encodes two major proteins, 19K and 55K, that prevent, via different routes, the induction of apoptosis resulting from the activity of the E1A proteins. In addition, the E1B-55K protein is required in the late phase for selective viral mRNA transport and inhibition of host protein expression. Early region-2 (E2) is also divided into an E2A and E2B region that together encode three proteins, DNA binding protein, viral polymerase and pre-terminal protein, all involved in replication of the viral genome. The E3 region is not necessary for replication in vitro but encodes several proteins that subvert the host defense mechanism towards viral infection. The E4 region encodes at least six proteins involved in several distinct functions related to viral mRNA splicing and transport, host-cell mRNA transport, viral and cellular transcription and transformation.

The late proteins necessary for formation of the viral capsids and packaging of viral genomes, are all generated from the major late transcription unit (MLTU) that becomes fully active after the onset of viral DNA replication. A complex process of differential splicing and polyadenylation gives rise to more than 15 mRNA species that share a tripartite leader sequence. The early proteins E1B-55K and E4-Orf3 and Orf6 play a pivotal role in the regulation of late viral mRNA processing and transport from the nucleus.

Packaging of newly formed viral genomes in pre-formed capsids is mediated by at least two Adenoviral proteins, the late protein 52/55K and an intermediate protein IVa2, through interaction with the viral packaging signal ($\Psi$) located at the left end of the Ad5 genome. A second intermediate protein, pIX, is part of the capsid and is known to stabilize the hexon-hexon interactions. In addition, pIX has been described to transactivate TATA-containing promoters like the E1A promoter and the major late promoter (MLP).

Adenovirus-Based Vectors and Adenoviral Packaging Cell Lines

Adenovirus-based vectors have been used as a means to achieve high-level gene transfer into various cell types, as vaccine delivery vehicles, for gene transfer into allogeneic tissue transplants for gene therapy, and to express recombinant proteins in cell lines and tissues that are otherwise difficult to transfect with high efficiency. The current known systems for packaging Adenovirus-based vectors consist of a host cell and a source of the Adenoviral late genes. The current known host cell lines, including the 293, QBI, and PERC 6 cells, express only early (non-structural) Adenovirus (Ad) genes, not the Ad late (structural) genes needed for packaging. The Ad late genes have previously been provided either by the Ad vectors themselves or by a helper Ad virus. Recently, "gutless" Adenoviral vectors—vectors that are devoid of all viral-protein-coding DNA sequences—have been developed. The gutless Adenoviral vectors contain only the ends of the viral genome (LITR and RITR), therapeutic gene sequences, and the normal packaging recognition signal ($\Psi$), which allows this genome to be selectively packaged and released from cells. However, to propogate the gutless adenoviral vector requires a helper adenovirus (the helper) that contains the adenoviral genes required for replication and virion assembly as well as LITR, RITR, and $\Psi$. While this helper-dependent system allows the introduction of up to about 32 kb of foreign DNA, the helper virus contaminates the preparations of gutless Adenoviral vectors. This contaminating replication competent helper virus poses serious problems for gene therapy, vaccine, and transplant applications both because of the replication competent virus and because of the host's immune response to the adenoviral genes in the helper virus. One approach to decrease helper contamination in this helper-dependent vector system, has been to introduce a conditional gene defect in the packaging recognition signal ($\Psi$) making it less likely that its DNA is packaged into a virion. Gutless Adenoviral vectors produced in such systems still have significant contamination with helper virus. Being able to produce gutless Adenoviral gene transfer vectors without helper virus contamination would offer further reduced toxicity and prolonged gene expression in animals.

It is believed that these Ad late genes in the vector or in the helper Ad virus: 1) contribute to the inflammatory response to the Adenovirus vector in gene therapy applications, 2) interfere with the immune response in vaccine applications, 3) induce immune non-responsiveness to Adenovirus in allogeneic transplant applications, and 4) result in protein contaminants in protein expression applications. Further, they occupy space in the Adenoviral vector that could beneficially be used for carrying other genetic information. Remarkable progress has been made with these vectors in the last decade, but some shortcomings continue to challenge investigators.

Adenovirus Vectors for Gene Therapy and Protein Expression

Gene delivery or gene therapy is a promising method for the treatment of acquired and inherited diseases. An ever-expanding array of genes for which abnormal expression is associated with life-threatening human diseases are being cloned and identified. The ability to express such cloned genes in humans will ultimately permit the prevention and/or cure of many important human diseases, diseases for which current therapies are either inadequate or non-existent. Unfortunately, however, gene therapy protocols described to date have been plagued by a variety of problems, including in particular the short period of gene expression from the vector and the inability to effectively readminister the same vector a second time, both of which are caused by the host immune response against antigens associated with the vector and its therapeutic payload. Tissues that have incorporated the viral and/or therapeutic genes are initially attacked by the host's cellular immune response, mediated by CD8+ cytotoxic T cells as well as CD4+ helper T cells, which dramatically limits the persistence of gene expression from the vectors. Moreover, the host's humoral immune response mediated by the CD4+ T cells further limits the effectiveness of current gene therapy protocols by inhibiting the successful readministration of the same vector.

For example, following an initial administration of an Adenoviral vector, serotype-specific antibodies are generated against epitopes of the major viral capsid proteins, namely the penton, hexon and fiber. Given that such capsid proteins are the means by which the Adenovirus attaches itself to a cell and subsequently infects the cell, such antibodies are then able to block or "neutralize" reinfection of a cell by the same serotype of Adenovirus. This necessitates using a different serotype of Adenovirus in order to administer one or more subsequent doses of exogenous therapeutic DNA in the context of gene therapy and vaccines. In addition, both therapeutic and viral gene products are expressed on the target cells making them susceptible to cellular immune responses. Thus, they are rejected and the beneficial effect of the gene therapy is negated and the target organ or tissue may be destroyed. As a result of these immune-related obstacles, progress in gene therapy protocols has been stymied.

A large research effort has been mounted to optimize virus-based gene transfer vectors. Yet, the initial promise of gene therapy has been undermined by the biology of the commonly used viral vectors. For example, retroviruses are intrinsically mutagenic and oncogenic as they integrate into the human genome, and currently available Adenoviral vectors induce vigorous humoral and cellular immune responses that negate their therapeutic potential. Although the mutagenic and oncogenic properties of retroviral vectors are intrinsic, the immunogenicity of Adenoviral vectors may be mitigated. These responses arise from Adenoviral gene products expressed from the Adenoviral vector itself or from associated helper virus.

Adenovirus Vectors for Immunosuppressive Therapy

Transplants of allogeneic cells and tissues are an increasingly frequent and important method of treating various disease and conditions. With the advent of embryonic and other stem cell based therapies, there will be a further increase in such transplants. One challenge faced by such transplants is rejection by the recipient's immune system. Such rejection is prevented by long-term treatment with general immune suppressants such as rapamycin and cyclosporine A. However, treatment with such general immune suppressants results in an inhibition of protective immunity, resulting in susceptibility to a host of bacterial, viral, and fungal infections with associated morbidity and mortality.

A number of methods have been proposed for inducing specific immune suppression directed at the allogeneic cells or tissues transplanted. One of these methods is based on the classical "veto effect" that employs donor-derived $CD8^+$ T cells to inhibit cellular immune responses. Yet, allogeneic grafts may only be partially protected by classical veto as $CD8^+$ T cells may fail to remove organ-specific allo-reactive T cells.

Inducing the veto effect can be accomplished by a number of methods that result in the presence of CD8 on the surface of the transplanted allogeneic cells, including treating the allogeneic transplant with a protein fusion of CD8 and an antibody specific for a protein present of the allogeneic cells or tissues to be transplanted. The CD8 can also be "engineered" to the surface of the cells by introducing a transcriptionally and translationally active copy of the CD8 gene to the cells or tissues to be transplanted.

Adenoviral vectors are particularly suited for transduction of the CD8 gene to allogeneic cells/tissues for transplantation because they infect a wide range of cell and tissues with high efficiency and because the transduced DNA is expressed transiently and not permanently integrated into the genome of the transduced cells.

The ability of the CD8 to induce long-term immune non-responsiveness raises a challenge for the use of Adenoviral vectors: the expression of Adenoviral genes in conjunction with the CD8 gene form cells in the allogeneic transplant may induce the transplant recipient to a state of long-term non-responsiveness to the Adenovirus used as the basis for the vector. Adenovirus is a human pathogen and though not normally a great risk, it is associated with significant morbidity in immunocompromised people such as AIDS patients incapable of mounting an immune response to it.

At least 53 different forms of human Adenovirus have been characterized. The discriminating factor among these viruses is the humoral immune (i.e. antibody) response to the capsid hexon protein (encoded by various alleles of the L3 gene). In fact, the majority of variation among the different hexon proteins occurs in three "hyper"-variable regions; the humoral immune response to Adenoviruses is centered on these hypervariable regions.

The use of Adenovirus to deliver CD8 to protect allogeneic transplants from rejection poses unique problems, not the same as posed by other uses of Adenoviral vectors for more standard gene therapy protocols. Specifically, in standard gene therapy, the injection of a large number of Adenovirus particles into the patient may activate the pre-existing immunity to the Adenoviral vector which can interfere with the transduction of the therapeutic gene, lead to inflammatory responses, and in extreme cases the immune response result in death of the patient. The source of Adenoviral antigens engaging the pre-existing immunity can come both from the gene therapy virions and from newly synthesized Adenoviral proteins produced by infected cells.

Two advances have sought to overcome these problems are the use of "gutless" (fully-deleted) Adenoviral vectors and the use of rare Adenoviral hexons. While the use of "gutless" Adenoviral vectors removes the L3 gene from the therapeutic vector, the propagation of these "gutless" viruses requires the presence of helper Adenovirus that still contains L3 genes. And these helper viruses are significant contaminants in the therapeutic preparations of the "gutless" Adenoviral vectors. The use of L3 genes from rare adenoserotypes may avoid the problem of pre-existing immunity in that fraction of patients who have not been previously exposed to the Adenoviral serotype. Still, as the Adenoviral hexon proteins are highly immunogenic, there is a high probability that repeated treatments with an Adenoviral gene delivery vector based on a rare serotype will eventually induce an immune reaction, including neutralizing antibodies. In summary, the problem with Adenoviral vectors for classical gene therapy protocols is the presence or development of an immune response to the Adenoviral proteins that interferes with transduction of the therapeutic gene and/or causes inflammatory or other immune responses.

In the use of Adenovirus to deliver the CD8 gene to allogeneic cells/tissues ex vivo before reimplantation, the problem of immune reaction to the Adenoviral genes is quite different: here one is concerned with the induction of long-term immune non-responsiveness to whichever Adenovirus serotype serves as the basis for the vector.

Adenoviruses as Vaccine Vectors

Adenoviruses have transitioned from tools for gene replacement therapy to bona fide vaccine delivery vehicles. They are attractive vaccine vectors as they induce both innate and adaptive immune responses in mammalian hosts. Currently, Adenovirus vectors are being tested as subunit vaccine systems for numerous infectious agents ranging from malaria to HIV-1. Additionally, they are being explored as vaccines against a multitude of tumor-associated antigens. Thus far, most efforts have focused on vectors derived from Adenovirus of the human serotype 5 (AdHu5) for eventual use as vaccines for humans, while bovine, porcine, and ovine Adenoviruses have been explored for veterinary use.

The dynamics of Adenoviral gene expression have made the production of true Adenoviral packaging cell lines difficult: expression of the Adenoviral early functional transcription region (E1A) gene induces expression of the Adenoviral late genes (structural, immunogenic genes), which in turn kills the cell. Accordingly, a host cell that constitutively expresses the Adenoviral early genes cannot carry the "wild-type" Adenoviral late cistron. Previous host cells for propagating Adenoviral vectors are not "packaging" cells. Specifically, the 293, QBI and PERC 6 cells express only early (non-structural) Adenoviral genes, not the Adenoviral late genes needed for packaging. The Adenoviral late genes have previously been provided either by the Adenoviral vector or by a helper Adenoviral virus. These Adenoviral late genes in the Adenoviral vector or in a helper Adenoviral virus contribute to the inflammatory response to the Adenoviral vector; interfere with the immune response to Adenoviral based vaccines; induce immune non-responsiveness to Adenovirus in allogeneic transplant applications, and contribute to contamination in Adenoviral based protein expression. Further, they occupy space that could beneficially be used for carrying other genetic information.

The described invention addresses this problem and provides systems and methods for the construction of fully-deleted helper-independent Adenoviral vectors and uses thereof.

SUMMARY

The embodiments disclosed herein relate to the construction of fully-deleted Adenovirus-based gene transfer vectors (GDVs) packaged without the use of helper Adenovirus, and more particularly to their use in gene therapy for gene and protein expression, vaccine development, and immunosuppressive therapy.

According to aspects illustrated herein, there is provided an Adenovirus packaging cell line permissive for replication of a fully-deleted Adenoviral vector independent of helper Adenovirus that includes an Adenovirus early region 1 (E1) coding sequence and an Adenovirus pIX coding sequence, both of which are stably integrated into the cell line. In a preferred embodiment, no additional viral coding sequences are present in the Adenovirus packaging cell line.

According to aspects illustrated herein, there is provided a system that includes (a) an Adenovirus packaging cell line; (b) a fully-deleted Adenoviral vector construct; and optionally (c) a packaging construct, wherein the fully-deleted Adenoviral vector construct and optionally the packaging construct can transfect the Adenovirus packaging cell line resulting in the encapsidation of a fully-deleted Adenoviral vector independent of helper Adenovirus. The packaging construct itself is incapable of being packaged, and the encapsidated fully-deleted Adenoviral vector is replication deficient.

According to aspects illustrated herein, there is disclosed a method for producing an Adenovirus packaging cell line permissive for replication of a fully-deleted Adenoviral vector independent of helper Adenovirus that includes introducing into a cell line permissive for Adenovirus replication an isolated nucleic acid molecule comprising an Adenovirus early region 1 (E1) coding sequence and an Adenovirus pIX coding sequence, wherein the Adenovirus early region 1 (E1) coding sequence and the Adenovirus pIX coding sequence are stably integrated into the cell line.

According to aspects illustrated herein, there is disclosed a method for propagating an adenoviral vector that includes (a) providing an Adenovirus packaging cell line; (b) transfecting a fully-deleted Adenoviral vector construct into the cell line; and optionally (c) transfecting a packaging construct into the cell line, wherein the fully-deleted Adenoviral vector construct and optionally the packaging construct can transfect the Adenovirus packaging cell line resulting in the encapsidation of a fully-deleted Adenoviral vector independent of helper Adenovirus.

In some embodiments, gene transfer vectors (GTVs) of the present disclosure are useful in a method of treating cancer. In some embodiments, gene transfer vectors (GTVs) of the present disclosure are useful in a method of treating skin disorders. In some embodiments, gene transfer vectors (GTVs) of the present disclosure are useful in a method of treating vascular disease. In some embodiments, gene transfer vectors (GTVs) of the present disclosure are useful in a method of treating cardiac disease. In some embodiments, gene transfer vectors (GTVs) of the present disclosure are useful in a method of treating an auto-immune disease. In some embodiments, gene transfer vectors (GTVs) of the present disclosure are useful in a method of treating a parasitic infection. In some embodiments, gene transfer vectors (GTVs) of the present disclosure are useful in a method of treating a viral infection. In some embodiments, gene transfer vectors (GTVs) of the present disclosure are useful in a method of treating a bacterial infection. In some embodiments, gene transfer vectors (GTVs) of the present disclosure are useful in a method of treating a yeast infection. In some embodiments, gene transfer vectors (GTVs) of the present disclosure are useful in a method of treating a neurological disease. In some embodiments, gene transfer vectors (GTVs) of the present disclosure are useful in a method of treating a hereditary disease.

In some embodiments, an encapsidated fully-deleted Adenoviral vector produced by a method of the present disclosure is used as a gene delivery vector for protein expression. In some embodiments, an encapsidated fully-deleted Adenoviral vector produced by a method of the present disclosure is used in developing and manufacturing vaccines. In some embodiments, an encapsidated fully-deleted Adenoviral vector produced by a method of the present disclosure is used as a gene delivery vector for immunosuppressive therapy. In an embodiment, a target cell is transduced with an encapsidated fully-deleted Adenoviral vector produced by a method of the present disclosure.

DETAILED DESCRIPTION

Figure 1:
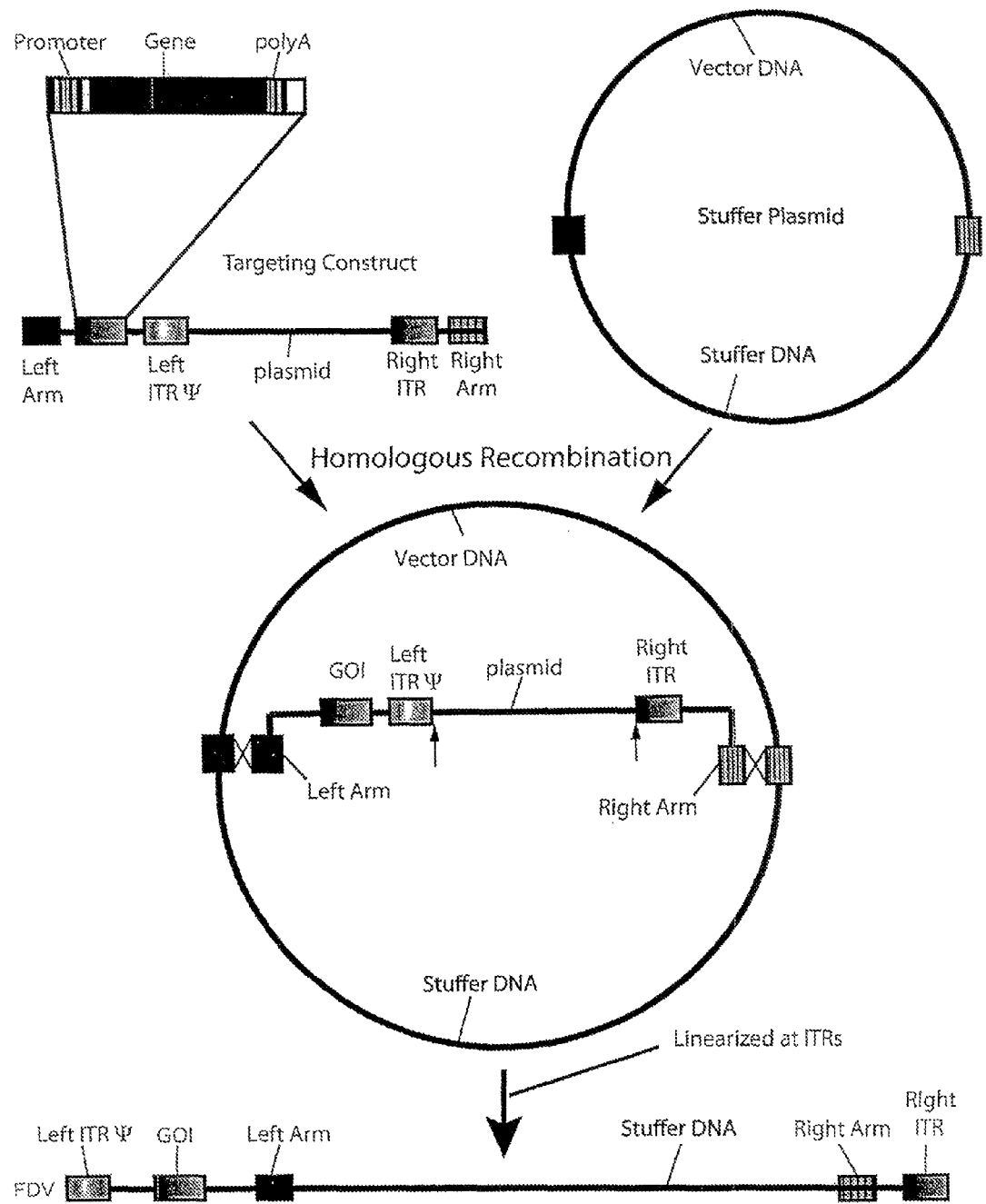
FIG. 1 is a diagrammatic representation showing an embodiment of a method for the creation of a fully-deleted Adenoviral vector construct (FDV) using homologous recombination with a plasmid comprising stuffer DNA.

The present disclosure provides, among other things, fully-deleted Adenoviral vector constructs (FDVs), packaging constructs (pPacks) and Adenovirus packaging cells (PCs) for propagating fully-deleted Adenovirus-based gene transfer vectors (GDVs) packaged without helper Adenovirus. The GDVs find use in gene therapy for gene and protein expression, vaccine development and immunosuppressive therapy. Any subtype, mixture of subtypes, or chimeric Adenovirus may be used as the source of DNA for generation of a FDV. In an embodiment, the source of DNA is from Human Serotype 5. Given that the Ad5 genome has been completely sequenced, the present disclosure will be described with respect to the Ad5 serotype.

To the inventors knowledge, all previous versions of Ad viral gene transfer vectors were contaminated with Adenoviral genes. In the case of first- and second-generation Ad vectors, the Ad vector itself carried the Ad genes, while in the case of "gutless" Ad vectors, the contaminating helper virus needed for production of Ad gutless vectors carry the Ad genes. Accordingly, when cells were infected with the Ad gene delivery vector they were also transduced with Ad genes. In the systems and methods disclosed herein, the Ad genes are provided by a host cell into which they are stably integrated and/or by a pPack nucleic acid transfected into the host cell. Accordingly, the GDVs of the present invention are uniquely not contaminated with Ad genes.

Unless defined otherwise, all technical and scientific terms used herein have the same meaning as commonly understood by one of ordinary skill in the art to which this disclosure belongs. Generally, the nomenclature used herein and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document. Units, prefixes, and symbols may be denoted in their SI accepted form. Unless otherwise indicated, nucleic acids are written left to right in 5' to 3' orientation; amino acid sequences are written left to right in amino to carboxyl orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms ($5^{th}$ edition, 1993). As employed throughout the disclosure, the following terms, unless otherwise indicated, shall be understood to have the following meanings and are more fully defined by reference to the specification as a whole:

The terms "Adenovirus" and "Adenoviral particle" as used herein include any and all viruses that may be categorized as an Adenovirus, including any Adenovirus that infects a human or an animal, including all groups, subgroups, and serotypes. Thus, as used herein, "Adenovirus" and "Adenovirus particle" refer to the virus itself or derivatives thereof and cover all serotypes and subtypes and both naturally occurring and recombinant forms. In one embodiment, such Adenoviruses infect human cells. Such Adenoviruses may be wildtype or may be modified in various ways known in the art or as disclosed herein. Such modifications include modifications to the Adenovirus genome that is packaged in the particle in order to make an infectious virus. Such modifications include deletions known in the art, such as deletions in one or more of the E1a, E1b, E2a, E2b, E3, or E4 coding regions.

An "Adenovirus packaging cell" is a cell that is able to package Adenoviral genomes or modified genomes to produce viral particles. It can provide a missing gene product or its equivalent. Thus, packaging cells can provide complementing functions for the genes deleted in an Adenoviral genome and are able to package the Adenoviral genomes into the Adenovirus particle. The production of such particles requires that the genome be replicated and that those proteins necessary for assembling an infectious virus are produced. The particles also can require certain proteins necessary for the maturation of the viral particle. Such proteins can be provided by a vector, a packaging construct or by the packaging cell. Exemplary host cells (HCs) that may be used to make a packaging cell line according to the present invention include, but are not limited to A549, HeLa, MRC5, W138, CHO cells, Vero cells, human embryonic retinal cells, or any eukaryotic cells, as long as the host cells are permissive for growth of Adenovirus. Some host cell lines include adipocytes, chondrocytes, epithelial, fibrobasts, glioblastoma, hepatocytes, keratinocytes, leukemia, lymphoblastoid, monocytes, macrophages, myoblasts, and neurons. Other cell types include, but are not limited to, cells derived from primary cell cultures, e.g., human primary prostate cells, human embryonic retinal cells, human stem cells. Eukaryotic dipolid and aneuploid cell lines are included within the scope of the invention. The packaging cell must be one that is capable of expressing the products of the FDV and/or pPack constructs at the appropriate level for those products in order to generate a high titer stock of recombinant GDVs.

By "antigen" is meant a molecule which contains one or more epitopes that will stimulate a host's immune system to make a cellular antigen-specific immune response, or a humoral antibody response. Thus, antigens include proteins, polypeptides, antigenic protein fragments, oligosaccharides, polysaccharides, and the like. Furthermore, the antigen can be derived from any known virus, bacterium, parasite, plants, protozoans, or fungus, and can be a whole organism. The term also includes tumor antigens. Similarly, an oligonucleotide or polynucleotide which expresses an antigen, such as in DNA immunization applications, is also included in the definition of antigen. Synthetic antigens are also included, for example, polyepitopes, flanking epitopes, and other recombinant or synthetically derived antigens (Bergmann et al. (1993) Eur. J. Immunol. 23:2777 2781; Bergmann et al. (1996) J. Immunol. 157:3242 3249; Suhrbier, A. (1997) Immunol. and Cell Biol. 75:402 408; Gardner et al. (1998) 12th World AIDS Conference, Geneva, Switzerland, Jun. 28-Jul. 3, 1998).

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus A transcription termination sequence may be located 3' to the coding sequence. Transcription and translation of coding sequences are typically regulated by "control elements," including, but not limited to, transcription promoters, transcription enhancer elements, Shine and Delagarno sequences, transcription termination signals, polyadenylation sequences (located 3' to the translation stop codon), sequences for optimization of initiation of translation (located 5' to the coding sequence), and translation termination sequences.

The term "construct" refers to at least one of a fully-deleted Adenoviral vector construct (FDV) of the present invention or a packaging construct (pPack) of the present invention.

The term "delete" or "deleted" as used herein refers to expunging, erasing, or removing.

The term "E1 region" as used herein refers to a group of genes present in the Adenovirus genome. These genes, such as, but not limited to, E1A and E1B, are expressed in the early phase of virus replication and activate the expression of the other viral genes. In an embodiment, an Adenoviral packaging cell line of the present disclosure includes all coding sequences that make up the E1 region. In an embodiment, an Adenoviral packaging cell line of the present disclosure includes some coding sequences that make up the E1 region (for example, E1A or E1B)

As used herein, the term "E1A" refers to all gene products of the Adenovirus E1A region, including expression products of the two major RNAs: 13S and 12S. These are translated into polypeptides of 289 and 243 amino acids, respectively. These two proteins differ by 46 amino acids, which are spliced from the 12S mRNA, as described in Chow et al. (1980) Cold Spring Harb Symp Quant Biol. 44 Pt 1:401 14; and Chow et al. (1979) J. Mol. Biol. 134(2):265 303, herein specifically incorporated by reference. For the purposes of the invention, the packaging cell line may express the 289 polypeptide, the 243 polypeptide, or both the 289 and the 243 polypeptide. The term E1A is also used herein with reference to partial and variant E1A coding sequences.

As used herein, the term "E1B" refers to all gene products of the Adenovirus E1B region, including the 3 major polypeptides, of 19 kd and 55 kd. The E1B 19 kd and 55 kd proteins are important in cell transformation. For the purposes of the invention, the packaging cell line may express the 19 Kd polypeptide, the 55 Kd polypeptide, or both the 19 and the 55 Kd polypeptide. The term E1B is also used herein with reference to partial and variant E1B coding sequences.

The term "E2" as used herein refers to a cistron with at least 3 ORFs all of which are involved in DNA replication, including a polymerase. The E2 late promoter of Adenovirus has been described, for example, by Swaminathan, S., and Thimmapaya, B. (1995) Curr. Top. Microbiol. Immunol., 199, 177-194. In the Adenoviral system, the E2 late promoter, together with the E2 early promoter, has the function of controlling the adenoviral E2 region and/or genes E2A and E2B. In this case, the synthesis of the E2 mRNA takes places initially starting out from the E2 early promoter. Approximately five to seven hours after the infection of a cell, a switch-over to the E2 later promoter takes place.

The term "E3 region" as used herein refers to a group of genes that are present in the Adenovirus genome and are expressed in the early phase of the virus replication cycle. These genes express proteins that interact with the host immune system. They are not necessary for virus replication in vitro, and therefore may be deleted in Adenovirus vectors.

The term "E4 region" as used herein refers to a group of genes that are present in the Adenovirus genome next to the right ITR, and are expressed in the early phase of the virus replication cycle. The E4 region includes at least 7 ORFs. The products of the E4 region promote viral gene expression and replication, interact with host cell components, and participate in lytic infection and oncogenesis.

The term "expression" refers to the transcription and/or translation of an endogenous gene, transgene or coding region in a cell.

The terms "fully-deleted Adenoviral vector", "FDV", "gutless", "gutted", "mini", "fully-deleted", "Δ", or "pseudo" vectors as used herein refers to a linear, double-stranded DNA molecule with inverted terminal repeats (ITRs) separated by approximately 28 to 37 kb, the viral packaging signal (Ψ), and at least one DNA insert (all or a fragment of at least one gene of interest (GOI)) which comprises a gene sequence encoding a protein of interest. The gene sequence can be regulatable. Regulation of gene expression can be accomplished by one of 1) alteration of gene structure: site-specific recombinases (e.g., Cre based on the Cre-loxP system) can activate gene expression by removing inserted sequences between the promoter and the gene; 2) changes in transcription: either by induction (covered) or by relief of inhibition; 3) changes in mRNA stability, by specific sequences incorporated in the mRNA or by siRNA; and 4) changes in translation, by sequences in the mRNA. No viral coding genes are comprised in the FDV. FDVs are also called "high-capacity" Adenoviruses because they can accommodate up to 36 kilobases of DNA. As vector capsids package efficiently only DNA of 75-105% of the whole Adenovirus genome, and as therapeutic expression cassettes usually do not add up to 36 kb, there is a need to use "stuffer" DNA in order to complete the genome size for encapsidation. Conventional FDVs are referred to as "helper-dependent" Adenoviruses because they need a helper Adenovirus that carries essential Ad coding regions.

As used herein, the term "gene expression construct" refers to a promoter, at least a fragment of a gene of interest, and a polyadenylation signal sequence. A FDV of the present disclosure comprises a gene expression construct.

A "gene of interest" or "GOI" can be one that exerts its effect at the level of RNA or protein. Examples of genes of interest include, but are not limited to, therapeutic genes, immunomodulatory genes, virus genes, bacterial genes, protein production genes, inhibitory RNAs or proteins, and regulatory proteins. For instance, a protein encoded by a therapeutic gene can be employed in the treatment of an inherited disease, e.g., the use of a cDNA encoding the cystic fibrosis transmembrane conductance regulator in the treatment of cystic fibrosis. Moreover, the therapeutic gene can exert its effect at the level of RNA, for instance, by encoding an antisense message or ribozyme, an siRNA as is known in the art, an alternative RNA splice acceptor or donor, a protein that affects splicing or 3' processing (e.g., polyadenylation), or a protein that affects the level of expression of another gene within the cell (i.e., where gene expression is broadly considered to include all steps from initiation of transcription through production of a processed protein), perhaps, among other things, by mediating an altered rate of mRNA accumulation, an alteration of mRNA transport, and/or a change in post-transcriptional regulation.

As used herein, the phrase "gene therapy" refers to the transfer of genetic material (e. g., DNA or RNA) of interest into a host to treat or prevent a genetic or acquired disease or condition. The genetic material of interest encodes a product (e. g., a protein polypeptide, peptide or functional RNA) whose production in vivo is desired. For example, the genetic material of interest can encode a hormone, receptor, enzyme or (poly) peptide of therapeutic value. Examples of genetic material of interest include DNA encoding: the cystic fibrosis transmembrane regulator (CFTR), Factor VIII, low density lipoprotein receptor, betagalactosidase, alpha-galactosidase, beta-glucocerebrosidase, insulin, parathyroid hormone, and alpha-1-antitrypsin.

By "gene delivery vector" or "GDV" is meant a composition including an encapsidated fully-deleted Adenovirus-based vector of the present disclosure packaged without helper Adenovirus.

The term "helper-independent" as used herein refers to the process for creating an encapsidated fully-deleted Adenovirus-based gene transfer vector of the present disclosure that does not need the presence of a helper virus for its replication. These Adenoviruses include "first-generation" and "second-generation" Adenovirus vectors. A first-generation Adenovirus vector refers to an Adenovirus in which exogenous DNA replaces the E1 region, or optionally the E3 region, or optionally both the E1 and E3 region. A second-generation Adenovirus vector refers to a first-generation Adenovirus vector, which, in addition to the E1 and E3 regions, contains additional deletions in the E2 region, the E4 region, or any other region of the Adenovirus genome, or a combination thereof.

The term "helper virus" as used herein refers to virus used when producing copies of a helper-dependent viral vector which does not have the ability to replicate on its own. The helper virus is used to co-infect cells alongside the gutless virus and provides the necessary enzymes for replication of the genome of the gutless virus and the structural proteins necessary for the assembly of the gutless virus capsid.

By "immune response" is preferably meant an acquired immune response, such as a cellular or humoral immune response.

In the context of the present specification, an "immunomodulatory molecule" is a polypeptide molecule that modulates, i.e. increases or decreases, a cellular and/or humoral host immune response directed to a target cell in an antigen-specific fashion, and preferably is one that decreases the host immune response. Generally, in accordance with the teachings of the present invention the immunomodulatory molecule(s) will be associated with the target cell surface membrane, e.g., inserted into the cell surface membrane or covalently or non-covalently bound thereto, after expression from the GDVs described herein. In some embodiments, the immunomodulatory molecule comprises all or a functional portion of a CD8 protein, and even more preferably all or a functional portion of the CD8α-chain. For human CD8 coding sequences, see Leahy, Faseb J. 9:17-25 (1995); Leahy et al., Cell 68:1145-62 (1992); Nakayama et al., Immunogenetics 30:393-7 (1989). By "functional portion" with respect to CD8 proteins and polypeptides is meant that portion of the CD8α-chain retaining veto activity as described herein, more particularly that portion retaining the HLA-binding activity of the CD8α-chain, and specifically the immunoglobulin-like domain in the extracellular region of the CD8α-chain. Exemplary variant CD8 polypeptides are described in Gao and Jakobsen, Immunology Today 21:630-636 (2000), herein incorporated by reference. In some embodiments, the full length CD8α-chain is used. However, in some embodiments the cytoplasmic domain is deleted. Preferably the transmembrane domain and extracellular domain are retained.

By "immunosuppressive therapy" is meant treatment with a gene transfer vector of the present invention for suppressing the immune response to antigen(s). Immunosuppressive therapy is therapy used to decrease the body's immune response, such as drugs given to prevent or treat: transplant rejection (for example, in allogeneic transplantation), an autoimmune disease, an allergy, and a multiple myeloma.

By "inhibiting" is meant the direct or indirect, partial or complete, inhibition and/or reduction of an innate or acquired immune response, whether cellular (e.g., leukocyte recruitment) or humoral, to vector-associated antigens and/or to target cell-specific antigens. Vector-associated antigens include, e.g., antigens derived from the nucleic acid carrier or envelope (e.g. viral coat proteins and the like) as well as antigens derived from vector genes (e.g. bacterial or viral nucleic acids and proteins) and/or any therapeutic transgenes (e.g. mammalian nucleic acids and/or proteins) included in the vector.

The term "inverted terminal repeat" as used herein refers to DNA sequences located at the left and right termini of the Adenovirus genome. These sequences are identical to each other, but placed in opposite directions. The length of the inverted terminal repeats of Adenoviruses vary from about 50 bp to about 170 bp, depending on the serotype of the virus. The inverted terminal repeats contain a number of different cis-acting elements required for viral growth, such as the core origin of viral DNA replication and enhancer elements for the activation of the E1 region.

"In vivo gene therapy" and "in vitro gene therapy" are intended to encompass all past, present and future variations and modifications of what is commonly known and referred to by those of ordinary skill in the art as "gene therapy", including ex vivo applications.

The term "introducing", as used herein refers to delivery of an expression vector for stable integration of E1A and/or E1B coding sequences in a host cell. A vector may be introduced into the cell by transfection, which typically means insertion of heterologous DNA into a cell by physical means (e.g., calcium phosphate transfection, electroporation, microinjection or lipofection); infection, which typically refers to introduction by way of an infectious agent, i.e. a virus; or transduction, which typically means stable infection of a cell with a virus or the transfer of genetic material from one microorganism to another by way of a viral agent (e.g., a bacteriophage). As set forth above, the vector may be a plasmid, virus or other vehicle.

The term "linear DNA" as used herein refers to non-circularized DNA molecules.

The term "naturally" as used herein refers to as found in nature; wild-type; innately or inherently.

The term "nucleic acid" refers to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

Nucleic acids are "operably linked" when placed into a functional relationship with another nucleic acid sequence. For example, a promoter or enhancer is operably linked to a coding sequence if it affects the transcription of the sequence. Generally, "operably linked" means that the DNA sequences being linked are contiguous. However, enhancers do not have to be contiguous. Linking is accomplished by ligation at convenient restriction sites. If such sites do not exist, the synthetic oligonucleotide adapters or linkers are used in accordance with conventional practice.

The term "packaging construct" or "pPack" refers to an engineered plasmid construct of circular, double-stranded DNA molecules, wherein the DNA molecules include at least a subset of Adenoviral late genes (e.g., L1, L2, L3, L4, L5, E2A, and E4) under control of a promoter. The pPack does not include the inverted terminal repeats (ITRs) and the packaging signal (Ψ). The pPack is "replication defective"—the viral genome does not comprise sufficient genetic information alone to enable independent replication to produce infectious viral particles within a cell. Any subtype, mixture of subtypes, or chimeric Adenovirus may be used as the source of DNA for generation of the FDV and the pPack. However, given that the Ad5 genome has been completely sequenced, the present disclosure will be described with respect to the Ad5 serotype.

The term "packaging signal" as used herein refers to a nucleotide sequence that is present in the virus genome and is necessary for the incorporation of the virus genome inside the virus capsid during virus assembly. The packaging signal of Adenovirus is naturally located at the left-end terminus, downstream from the left inverted terminal repeat. It may be denoted as "Ψ".

The term "pathogen" is used in a broad sense to refer to the source of any molecule that elicits an immune response. Thus, pathogens include, but are not limited to, virulent or attenuated viruses, bacteria, fungi, protozoa, parasites, cancer cells and the like. Typically, the immune response is elicited by one or more peptides produced by these pathogens. As described in detail below, genomic DNA encoding the antigenic peptides from these and other pathogens is used to generate an immune response that mimics the response to natural infection. It will also be apparent in view of the teachings herein, that the methods include the use of genomic DNA obtained from more than one pathogen.

A cell that is "permissive" supports replication of a virus.

The term "plasmid" as used herein refers to an extra-chromosomal DNA molecule separate from the chromosomal DNA which is capable of replicating independently of the chromosomal DNA. In many cases, it is circular and double-stranded.

The term "polylinker" is used for a short stretch of artificially synthesized DNA which carries a number of unique restriction sites allowing the easy insertion of any promoter or DNA segment. The term "heterologous" is used for any combination of DNA sequences that is not normally found intimately associated in nature.

The term "promoter" is intended to mean a regulatory region of DNA that facilitates the transcription of a particular gene. Promoters usually comprise a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. A "constitutive promoter" refers to a promoter that allows for continual transcription of its associated gene in many cell types. An "inducible-promoter system" refers to a system that uses a regulating agent (including small molecules such as tetracycline, peptide and steroid hormones, nerotransmitters, and environmental factors such as heat, and osmolarity) to induce or to silence a gene. Such systems are "analog" in the sense that their responses are graduated, being dependent on the concentration of the regulating agent. Also, such systems are reversible with the withdrawal of the regulating agent. Activity of these promoters is induced by the presence or absence of biotic or abiotic factors. Inducible promoters are a powerful tool in genetic engineering because the expression of genes operably linked to them can be turned on or off at certain stages of development of an organism or in a particular tissue.

The term "propagate" or "propagated" as used herein refers to reproduce, multiply, or to increase in number, amount or extent by any process.

The term "purification" as used herein refers to the process of purifying or to free from foreign, extraneous, or objectionable elements.

The term "regulatory sequence" (also called "regulatory region" or "regulatory element") as used herein refers to a promoter, enhancer or other segment of DNA where regulatory proteins such as transcription factors bind preferentially. They control gene expression and thus protein expression.

The term "recombinase" as used herein refers to an enzyme that catalyzes genetic recombination. A recombinase enzyme catalyzes the exchange of short pieces of DNA between two long DNA strands, particularly the exchange of homologous regions between the paired maternal and paternal chromosomes.

The term "restriction enzyme" (or "restriction endonuclease") refers to an enzyme that cuts double-stranded DNA.

The term "restriction sites" or "restriction recognition sites" refer to particular sequences of nucleotides that are recognized by restriction enzymes as sites to cut the DNA molecule. The sites are generally, but not necessarily, palindromic, (because restriction enzymes usually bind as homodimers) and a particular enzyme may cut between two nucleotides within its recognition site, or somewhere nearby.

The term "replication" or "replicating" as used herein refers to making an identical copy of an object such as, for example, but not limited to, a virus particle.

The term "replication deficient" as used herein refers to the characteristic of a virus that is unable to replicate in a natural environment. A replication deficient virus is a virus that has been deleted of one or more of the genes that are essential for its replication, such as, for example, but not limited to, the E1 genes. Replication deficient viruses can be propagated in a laboratory in cell lines that express the deleted genes.

By "specific immune inhibition" or "antigen-specific immune inhibition" is meant the inhibition of immune responses directed against antigens such as vector-associated antigens, as opposed to general immune inhibition which is not antigen-specific. Thus, by way of example, the absence of a host cellular and/or humoral immune response to vector-associated antigens, combined with evidence of in vivo immune competence to other foreign antigens, would demonstrate specific immune inhibition of vector-associated antigens.

By "stable immunological tolerance" is meant stable, long-term allograft survival and/or function for at least one year without the use of general immunosuppressive agents.

The term "stuffer" as used herein refers to a DNA sequence that is inserted into another DNA sequence in order to increase its size. For example, a stuffer fragment can be inserted inside the Adenovirus genome to increase its size to about 36 kb. Stuffer fragments usually do not code for any protein nor contain regulatory elements for gene expression, such as transcriptional enhancers or promoters.

The term "target" or "targeted" as used herein refers to a biological entity, such as, for example, but not limited to, a protein, cell, organ, or nucleic acid, whose activity can be modified by an external stimulus. Depending upon the nature of the stimulus, there may be no direct change in the target, or a conformational change in the target may be induced.

As used herein, a "target cell" can be present as a single entity, or can be part of a larger collection of cells. Such a "larger collection of cells" may comprise, for instance, a cell culture (either mixed or pure), a tissue (e.g., epithelial or other tissue), an organ (e.g., heart, lung, liver, gallbladder, urinary bladder, eye or other organ), an organ system (e.g., circulatory system, respiratory system, gastrointestinal system, urinary system, nervous system, integumentary system or other organ system), or an organism (e.g., a bird, mammal, particularly a human, or the like). Preferably, the organs/tissues/cells being targeted are of the circulatory system (e.g., including, but not limited to heart, blood vessels, and blood), respiratory system (e.g., nose, pharynx, larynx, trachea, bronchi, bronchioles, lungs, and the like), gastrointestinal system (e.g., including mouth, pharynx, esophagus, stomach, intestines, salivary glands, pancreas, liver, gallbladder, and others), urinary system (e.g., such as kidneys, ureters, urinary bladder, urethra, and the like), nervous system (e.g., including, but not limited to, brain and spinal cord, and special sense organs, such as the eye) and integumentary system (e.g., skin). Even more preferably, the cells are selected from the group consisting of heart, blood vessel, lung, liver, gallbladder, urinary bladder, eye cells and stem cells. In an embodiment, the target cells are hepatocytes, and a method is provided for veto vector mediated transplantation of allogeneic hepatocytes in a subject. In an embodiment, the target cells are keratinocytes, and a method is provided for veto vector mediated transplantation of allogeneic keratinocytes in a subject, for example, engineered skin. In an embodiment, the target cells are pancreatic islets. In an embodiment, the target cells are cardiomyocytes. In an embodiment, the target cells are kidney cells, and a method is provided for veto vector mediated transplantation of allogeneic kidneys in a subject. In an embodiment, the target cells are fibroblasts, and a method is provided for veto vector mediated transplantation of allogeneic fibroblasts in a subject, for example, engineered skin. In an embodiment, the target cells are neurons. In an embodiment, the target cells are glia cells.

In particular, a target cell with which a GDV is contacted differs from another cell in that the contacted target cell comprises a particular cell-surface binding site that can be targeted by the GDV. By "particular cell-surface binding site" is meant any site (i.e., molecule or combination of molecules) present on the surface of a cell with which the GDV can interact in order to attach to the cell and, thereby, enter the cell. A particular cell-surface binding site, therefore, encompasses a cell-surface receptor and, preferably, is a protein (including a modified protein), a carbohydrate, a glycoprotein, a proteoglycan, a lipid, a mucin molecule or mucoprotein, and the like. Examples of potential cell-surface binding sites include, but are not limited to: heparin and chondroitin sulfate moieties found on glycosaminoglycans; sialic acid moieties found on mucins, glycoproteins, and gangliosides; major histocompatability complex I (MHC I) glycoproteins; common carbohydrate molecules found in membrane glycoproteins, including mannose, N-acetyl-galactosamine, N-acetyl-glucosamine, fucose, and galactose; glycoproteins, such as ICAM-1, VCAM, E-selectin, P-selectin, L-selectin, and integrin molecules; and tumor-specific antigens present on cancerous cells, such as, for instance, MUC-1 tumor-specific epitopes. However, targeting a GDV to a cell is not limited to any specific mechanism of cellular interaction (i.e., interaction with a given cell-surface binding site).

The term "transfection" as used herein refers to the introduction into a cell DNA as DNA (for example, introduction of an isolated nucleic acid molecule or a construct of the present disclosure). An Adenoviral packaging cell line disclosed herein is transfectied with at least one of a FDV or a pPack of the present disclosure. The term "transduction" as used herein refers to the introduction into a cell DNA either as DNA or by means of a GDV of the present disclosure. A GDV of the present disclosure can be transduced into a target cell.

The term "vector" refers to a nucleic acid used in infection of a host cell and into which can be inserted a polynucleotide. Vectors are frequently replicons. Expression vectors permit transcription of a nucleic acid inserted therein. Some common vectors include, but are not limited to, plasmids, cosmids, viruses, phages, recombinant expression cassettes, and transposons. The term "vector" may also refer to an element which aids in the transfer of a gene from one location to another.

The term "viral DNA" as used herein refers to a sequence of DNA that is found in virus particles.

The term "viral genome" as used herein refers to the totality of the DNA that is found in virus particles, and that contains all the elements necessary for virus replication. The genome is replicated and transmitted to the virus progeny at each cycle of virus replication.

The term "virions" as used herein refers to a viral particle. Each virion consists of genetic material within a protective protein capsid.

The term "wild-type" as used herein refers to the typical form of an organism, strain, gene, protein, nucleic acid, or characteristic as it occurs in nature. Wild-type refers to the most common phenotype in the natural population. The terms "wild-type" and "naturally occurring" are used interchangeably.

Fully-Deleted Adenoviral Vectors (FDVs)

FDVs only carry the cis acting sequences (i.e. ITRs, Ψ) necessary for viral genome replication and encapsidation. Conventional systems and methods for packaging FDVs require their co-infection with a "helper" Ad virus, which can be a source of immunogenic Ad antigens. Methods have been proposed to remove the contaminating Ad helper virus from the therapeutic Ad vector preparations. One example is to flank (flox) the packaging site Ψ in the Ad-"helper" virus with lox sequences for the Cre recombinase. In theory, passage of the fully deleted Ad vector and the "floxed" Ad helper virus would decrease contamination by excising the Ψ (packaging) sequence from the Ad "helper" virus and thereby preventing the packaging of the "helper" virus. In practice, this approach has not been able to reduce "helper" virus contamination below 1-in-$10^3$.

FIG. 1 shows the creation of a fully-deleted Adenovirus vector construct (FDV) of the present disclosure using homologous recombination with a plasmid comprising stuffer DNA. First, a targetting construct is engineered to comprise a gene of interest (GOI) as an expression construct (including a promoter and a polyadenylation signal sequence), the LITR Ψ and RITR from Adenovirus, and two regions of homology with the stuffer plasmid DNA sequence (left arm and right arm). The targeting construct and the stuffer plasmid homologously recombine in bacterial cells to produce a circular plasmid DNA comprising the plasmid backbone from the targeting construct and the stuffer DNA between the two recombination sites. Upon digestion with a restriction endonuclease at the outer edges of the LITR and the RITR (arrows), the fully-deleted Adenovirus vector construct (FDV) is produced.

In an embodiment, the GOI is a therapeutic gene, immunomodulatory gene, a vaccine gene or combinations thereof. In an embodiment, a FDV of the present disclosure expresses an immunomodulatory gene. In an embodiment, the immunomodulatory gene is a gene encoding human CD8. In an embodiment, a FDV of the present disclosure expresses a therapeutic gene. In an embodiment, the therapeutic gene is an interleukin. In an embodiment, the therapeutic gene is factor VIII. In some embodiments of the present disclosure, a FDV comprises one or more transgenes encoding therapeutic molecules of interest along with a CD8 polypeptide described herein. In an embodiment, the stuffer DNA of a FDV of the present disclosure is genomic DNA from the human adenylosuccinate lyase (ADSL) gene, which however, does not encode a functional enzyme in the purine biosynthesis pathway and purine nucleotide cycle. The ADSL gene is expressed constitutively as a "housekeeping" gene in most tissues. The ADSL human genomic DNA is used in the reverse complement orientation as "stuffer" DNA without the 5' upstream sequence or first exon of the ADSL gene to prevent any transcripts from being made from this DNA. In some embodiments, a FDV of the present disclosure further includes at least some Adenoviral late gene sequences. In some embodiments, a FDV of the present disclosure further includes at least some Adenoviral late gene sequences and a transcriptional activator. In some embodiments, a FDV of the present disclosure further includes a transcriptional activator. In an embodiment, the transcriptional activator is a mutant TetR-VP16 fusion protein. In an embodiment, the transcriptional activator is any transcription factor not normally expressed in the host cell.

Figure 2:
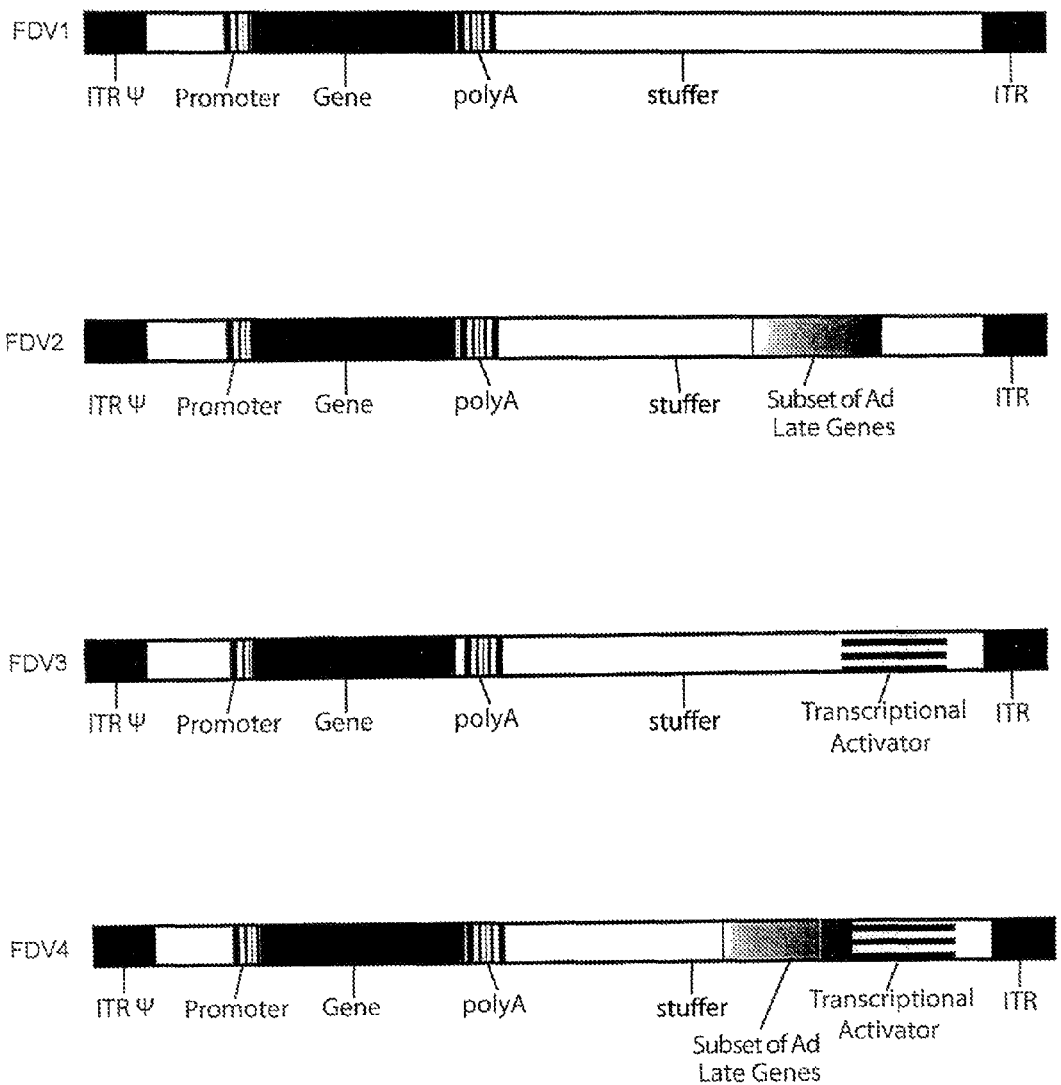
FIG. 2 is a set of schematic diagrams showing four embodiments of fully-deleted Adenoviral vector constructs (FDVs) of the present disclosure.

FIG. 2 is a set of schematic diagrams of four embodiments of FDVs of the present disclosure (i.e., FDV1, FDV2, FDV3 and FDV4), and Table 1 lists the sequences in each FDV embodiment. All embodiments of the FDVs comprise LITR, Ψ, and RITR from Adenovirus, at least one gene expression construct (with a promoter, at least a fragment of a gene of interest, and a polyadenylation signal sequence), and human genomic stuffer DNA. In some embodiments, a FDV of the present disclosure is described as an isolated nucleic acid molecule. In an embodiment, the promoter is the constitutive cytomegalovirus (CMV) major immediate early (IE) promoter. The FDV may also comprise a subset of Adenovirus late genes (for example, FDV2 & FDV4) and/or a transcriptional activator (for example, FDV3 & FDV4). In an embodiment, the subset of Adenovirus late genes is under the control of one or more promoters. In an embodiment, the Adenovirus late genes (and subset of Adenovirus late genes) is chosen from one of L1, L2, L3, L4, L5, E2A, and E4.

TABLE 1

FDVs

| | |
|---|---|
| FDV1 | Ad Backbone (LITRΨ, RITR), gene expression construct, Stuffer |
| FDV2 | Ad Backbone (LITRΨ, RITR), Subset of Adenovirus Late genes, gene expression construct, Stuffer |
| FDV3 | Ad Backbone (LITRΨ, RITR), Transcriptional Activator, gene expression construct, Stuffer |
| FDV4 | Ad Backbone (LITRΨ, RITR), Subset of Adenovirus Late genes, Transcriptional Activator, gene expression construct, Stuffer |

Packaging Constructs (pPack)

Figure 3:
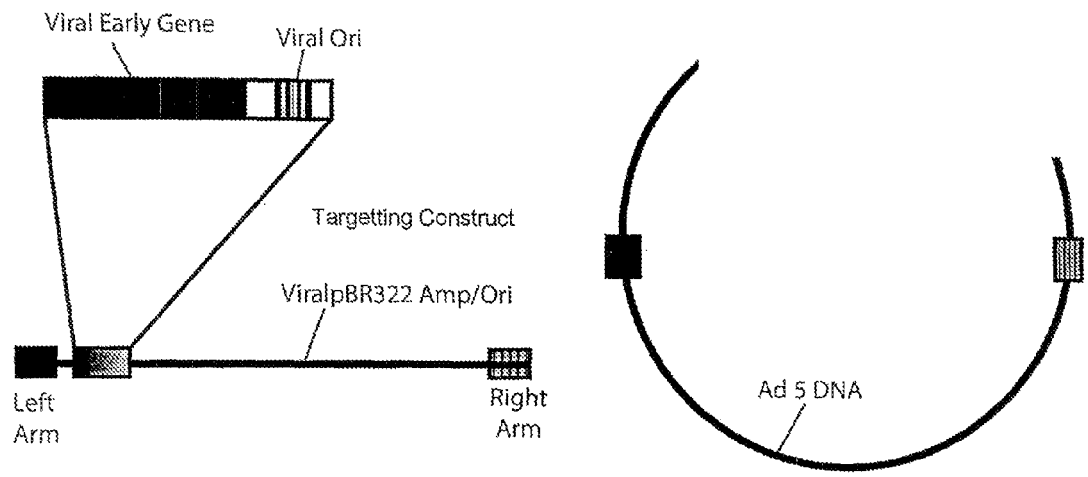
FIG. 3 is a diagrammatic representation showing an embodiment of a method for the creation of an Adenoviral packaging construct (pPack) using wild-type Adenovirus DNA.
Figure 3:
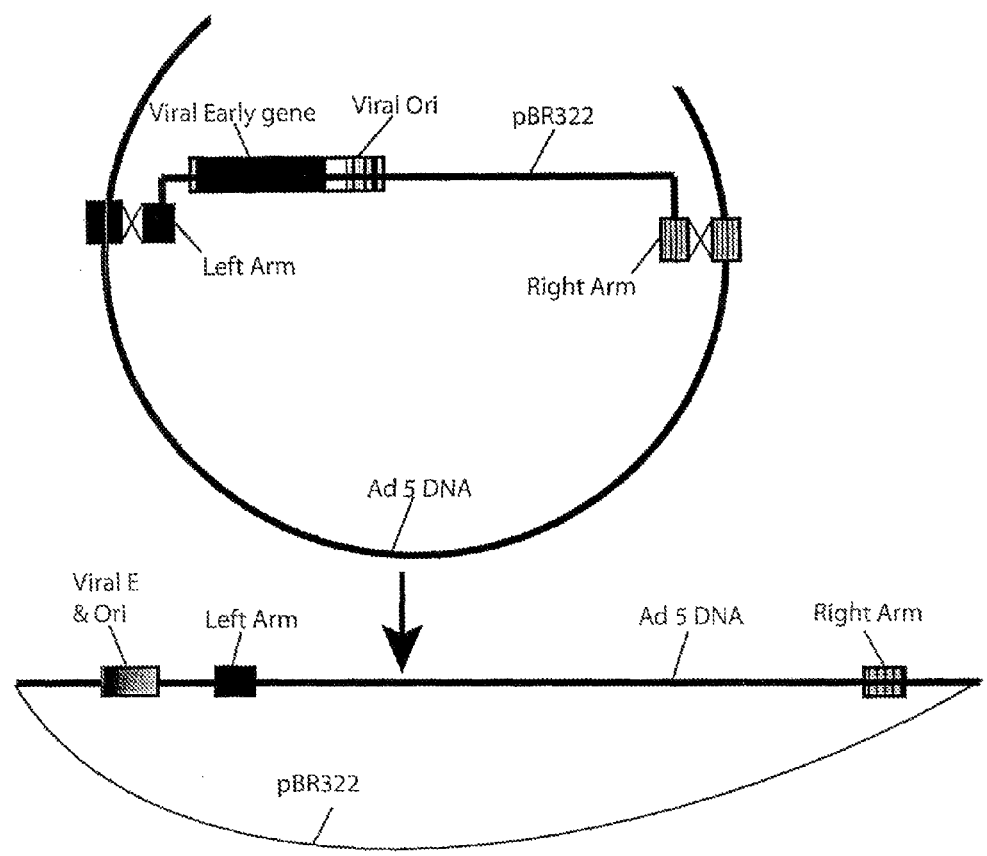
Figure 4:
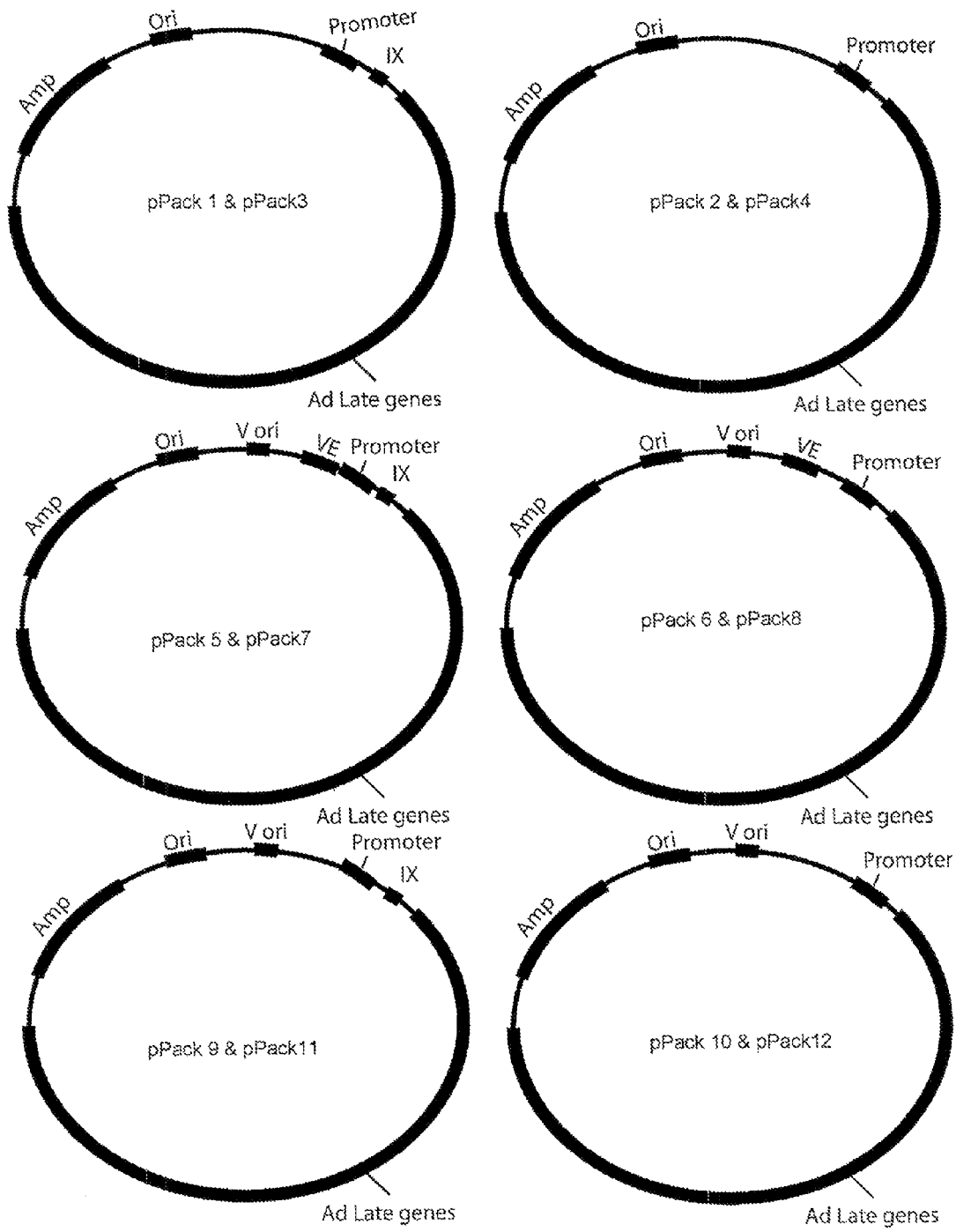
FIG. 4 is a set of schematic diagrams showing six embodiments of packaging constructs (pPacks) of the present disclosure.

FIG. 3 shows an embodiment of the creation of an Adenoviral packaging construct (pPack) using wild-type Adenovirus DNA (also described in Example 2). A targeting construct is engineered within a plasmid backbone comprising a non-Adenoviral viral early gene and origin of replication (ori), and two regions of homology to the Adenovirus DNA sequence located on either side of the Adenovirus late genes. In an embodiment, the viral origin of replication is SV40 and the viral early gene is SV40 T Ag. The targeting construct and the Ad DNA are co-transformed into bacteria (the bacterial ori-amp sequence of pBR322) in which they undergo homologous recombination, producing a circular plasmid comprising the Ad late genes and a non-adeno viral Early gene and origin of replication. FIG. 4 is a set of schematic diagrams of twelve embodiments of pPacks for use in a co-transfection system of the present disclosure (i.e., pPack1, pPack2, pPack3, pPack4, pPack5, pPack6, pPack7, pPack8, pPack9, pPack10, pPack11 and pPack12). The pPacks all comprise either all of the Adenoviral late genes or a subset thereof under control of at least one promoter. In an embodiment, the Adenovirus late genes (and subset of Adenovirus late genes) is chosen from one of L1, L2, L3, L4, L5, E2A, and E4. In some embodiments, a pPack of the present disclosure is described as an isolated nucleic acid molecule.

TABLE 2 pPack

| | |
|---|---|
| Ppack1 | Adenovirus Late genes + gene IX + the bacterial ori-amp sequence of pBR322 |
| Ppack2 | Adenovirus Late genes + the bacterial ori-amp sequence of pBR322 |

TABLE 2-continued pPack

| | |
|---|---|
| Ppack3 | Subset of Adenovirus Late genes + gene IX + the bacterial ori-amp sequence of pBR322 |
| Ppack4 | Subset of Adenovirus Late genes + the bacterial ori-amp sequence of pBR322 |
| Ppack5 | Adenovirus Late genes + gene IX + Viral Origin + Viral Early gene + the bacterial ori-amp sequence of pBR322 |
| Ppack6 | Adenovirus Late genes + Viral Origin + Viral Early gene + the bacterial ori-amp sequence of pBR322 |
| Ppack7 | Subset of Adenovirus Late genes + gene IX + Viral Origin + Viral Early gene + the bacterial ori-amp sequence of pBR322 |
| Ppack8 | Subset of Adenovirus Late genes + Viral Origin + Viral Early gene + the bacterial ori-amp sequence of pBR322 |
| Ppack9 | Adenovirus Late genes + gene IX + Viral Origin + the bacterial ori-amp sequence of pBR322 |
| Ppack10 | Adenovirus Late genes + Viral Origin + the bacterial ori-amp sequence of pBR322 |
| Ppack11 | Subset of Adenovirus Late genes + gene IX + Viral Origin + the bacterial ori-amp sequence of pBR322 |
| Ppack12 | Subset of Adenovirus Late genes + Viral Origin + the bacterial ori-amp sequence of pBR322 |

Adenoviral Packing Cell (PC)

A PC of the present disclosure is not designed to replicate wild type Adenovirus. In an embodiment, one isolated nucleic acid (NA) is stably integrated into a HC to create a PC expressing Adenoviral early region genes (see Table 3—PC1, PC2, PC3 and PC4). In an embodiment, two isolated nucleic acids (NAs) are stably integrated into a HC to create a PC expressing Adenoviral early region genes (see Table 3—PC5, PC6, PC7, PC8, PC9, PC10, PC11, PC12, PC13, PC14, PC15, PC16, PC17, PC18, PC19 and PC20). In some embodiments, viral early region genes of the PC can be a gene equivalent to an Adenoviral early region gene, for example viral genes that are functionally equivalent to an Adenoviral early region gene. Examples of viral early genes include, but are not limited to, simian 40 (SV40) large tumour antigen (Tag), human cytomegalovirus (HCMV) immediate-early (IE) region 2, and herpes simplex virus. In an embodiment, Adenoviral late genes can be cloned downstream of an inducible promoter. For example, the inducible promoter can be comprised of a plurality of sequential copies of the tet operator (TetO) sequence. In an embodiment, the inducible promoter comprises seven sequential copies of the TetO sequence. In an embodiment, Adenoviral late genes are regulated by a repressed promoter. In an embodiment, a single transfection system of the present disclosure utilize tetracycline-repressed promoters and repressors originally found on the Tn10 transposon in *E. coli*, in order to silence expression of the Ad genes when the specific transcriptional inducer is not present.

Table 3 lists coding sequences stably integrated into a host cell (HC) to create PCs of the present disclosure. A method for producing an Adenovirus packaging cell line permissive for replication of a fully-deleted Adenoviral vector independent of helper Adenovirus includes introducing into a cell line permissive for Adenovirus replication an isolated nucleic acid molecule comprising an Adenovirus early region 1 (E1) coding sequence and an Adenovirus pIX coding sequence, wherein the Adenovirus early region 1 (E1) coding sequence and the Adenovirus pIX coding sequence are stably integrated into the cell line.

TABLE 3

Figure 5:
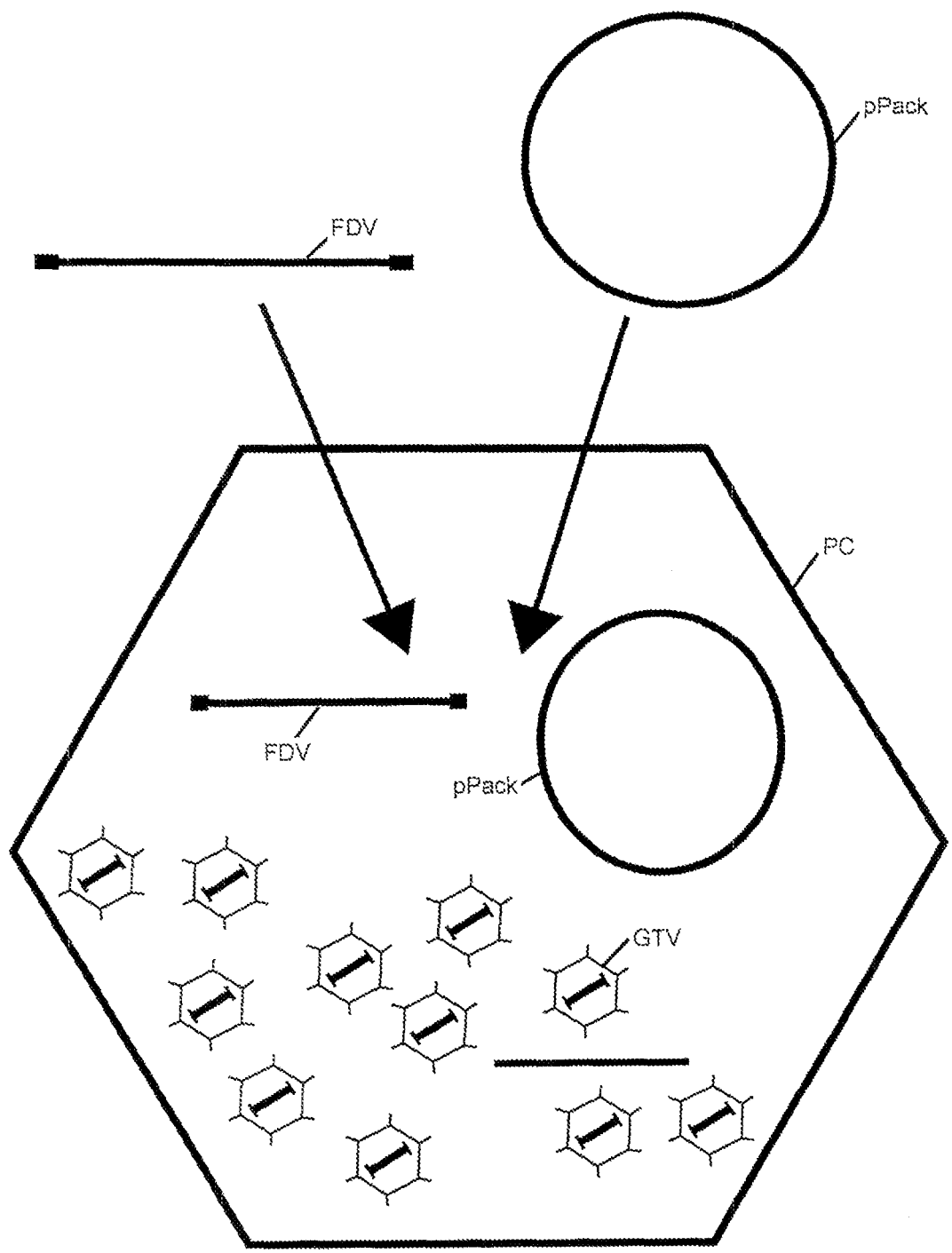
FIG. 5 is a diagrammatic representation showing an embodiment of a co-transfection system comprising a fully-deleted Adenoviral vector construct (FDV), a packing construct (pPack), and an Adenovirus packaging cell (PC) for producing encapsidated fully-deleted Adenovirus-based gene transfer vectors (GDVs) without helper Adenovirus.
Figure 6:
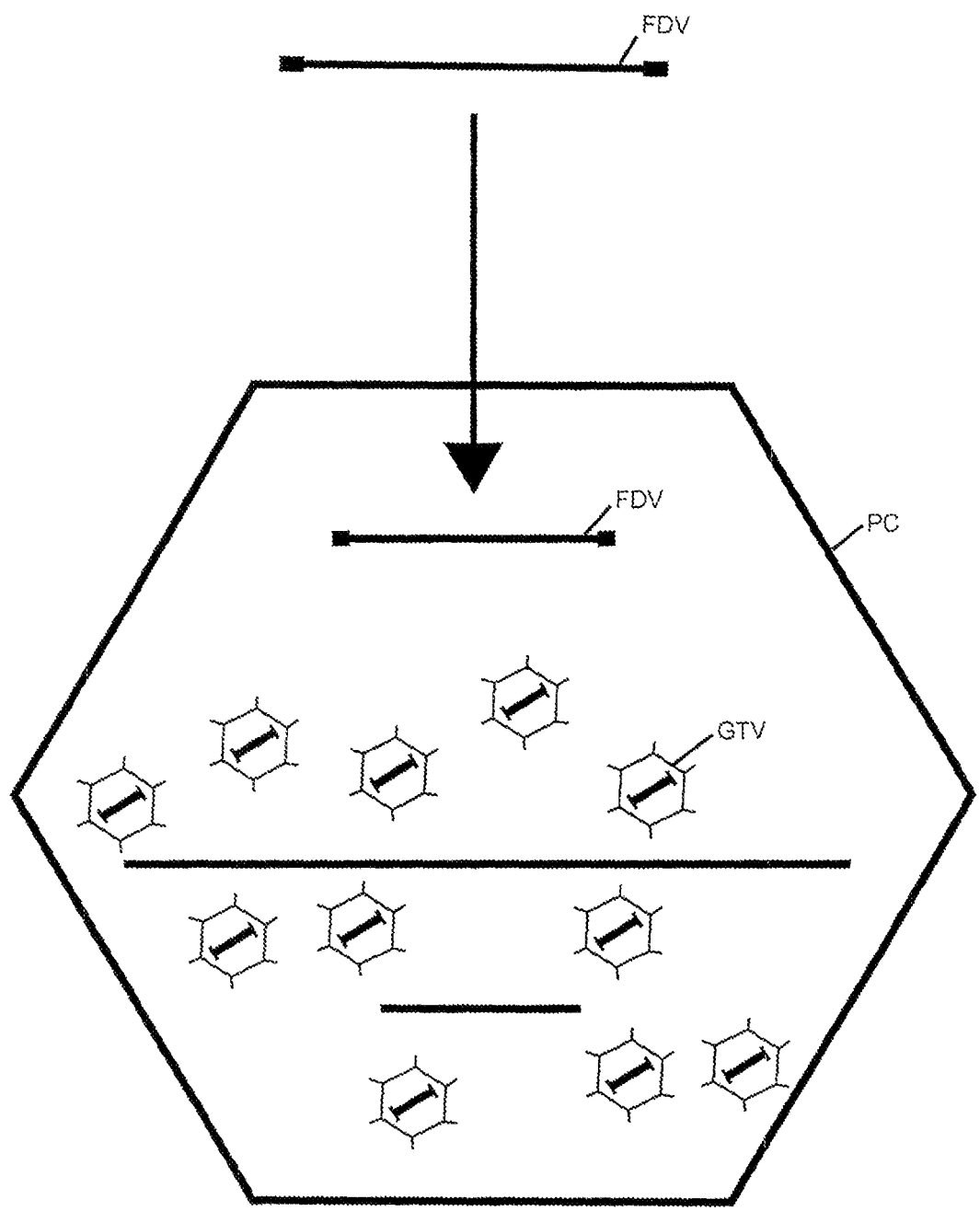
FIG. 6 is a diagrammatic representation showing an embodiment of a transfection system comprising a fully-deleted Adenoviral vector construct (FDV) and an Adenovirus packaging cell (PC) for producing encapsidated fully-deleted Adenovirus-based gene transfer vectors (GDVs) without helper Adenovirus.

| | PC | |
|---|---|---|
| | PC for Co-Transfection System - One Isolated NA - FIG. 5 | |
| PC1 | Adenovirus E1 coding sequence | |
| PC2 | Adenovirus E1 + protein IX coding sequence | |
| PC3 | Adenovirus E1, Viral Early gene coding sequence | |
| PC4 | Adenovirus E1 + protein IX coding sequence, Viral Early gene | |
| | PC for Single Transfection System where Late Genes Expressed under Inducible Promoter - Two Isolated NAs - FIG. 6 | |
| PC5 | Adenovirus E1 | Adenovirus Late genes + gene IX + Inducible promoter |
| PC6 | Adenovirus E1 + gene IX | Adenovirus Late genes + Inducible promoter |
| PC7 | Adenovirus E1 | Subset of Adenovirus Late genes + gene IX + Inducible promoter |
| PC8 | Adenovirus E1 + gene IX | Subset of Adenovirus Late genes + Inducible promoter |
| PC9 | Adenovirus E1 | Adenovirus Late genes + gene IX + Inducible promoter + Inducible viral Early gene + Viral origin of replication |
| PC10 | Adenovirus E1 + gene IX | Adenovirus Late genes + Inducible promoter + Inducible viral Early gene + Viral origin of replication |
| PC11 | Adenovirus E1 | Subset of Adenovirus Late genes + gene IX + Inducible promoter + Inducible viral Early gene + Viral origin of replication |
| PC12 | Adenovirus E1 + gene IX | Subset of Adenovirus Late genes + Inducible promoter + Inducible viral Early gene + Viral origin of replication |
| | PC for Single Transfection System where Late Genes Regulated by Repressed Promoter - Two Isolated NAs - FIG. 6 | |
| PC13 | Adenovirus E1, Repressor gene | Adenovirus Late genes + gene IX + promoter + tetO |
| PC14 | Adenovirus E1 + gene IX, Repressor gene | Adenovirus Late genes + promoter + tetO |
| PC15 | Adenovirus E1, Repressor gene | Subset of Adenovirus Late genes + gene IX + promoter + tetO |
| PC16 | Adenovirus E1 + gene IX, Repressor gene | Subset of Adenovirus Late genes + promoter + tetO |
| PC17 | Adenovirus E1, Repressor gene | Adenovirus Late genes + gene IX + promoter + tetO + Inducible Viral Early gene + Viral Ori |
| PC18 | Adenovirus E1 + gene IX, Repressor gene | Adenovirus Late genes + promoter + tetO + Inducible Viral Early gene + Viral Ori |
| PC19 | Adenovirus E1, Repressor gene | Subset of Adenovirus Late genes + gene IX + promoter + tetO + Inducible Viral Early gene + Viral Ori |
| PC20 | Adenovirus E1 + gene IX, Repressor gene | Subset of Adenovirus Late genes + promoter + tetO + Inducible Viral Early gene + Viral Ori |

In an embodiment, the repressor gene is tet Rep, however any repressor and its binding site ("operator") can be used to generalized.

At least one construct (e.g., pPack, FDV) is transfected into a host cell that lacks overlapping sequences with the nucleic acids of the host cell (and with each other if both a pPack and a FDV are co-transfected), the overlapping sequences otherwise enabling homologous recombination leading to replication competent wild type Adenovirus in the host cell into which the pPack and the FDV are to be transferred. In an embodiment, an isolated nucleic acid is introduced into a HC for stable integration of E1A and/or E1B coding sequences into the HC. In an embodiment, an isolated nucleic acid is introduced into a HC for stable integration of E1A and/or E1B and gene IX coding sequences into the HC. The presence of the gene IX coding sequence encodes for the second intermediate protein, pIX, which helps stabilize the viral capsid of GDVs propagated from the PC.

The regulation of the nucleic acid(s) expressed in the PC can be accomplished at the level of gene structure (e.g., activation by a site-specific recombinase), transcription (e.g., inducible or inhibitable promoter), mRNA stability, or translation. The regulation of the nucleic acid(s) expressed in the PC can be by the same or different systems. In an embodiment, the viral early gene(s) are silent until exposure to a transcriptional inducer. Expression of the viral early gene(s) can then induce expression of Adenoviral late genes. In an embodiment, the expression of at least one viral early gene can turn on the one or more Adenoviral late genes. In an embodiment, the at least one viral early gene product can be regulated by a constitutive promoter and the one or more Adenoviral late genes can be regulated directly. In an embodiment, the at least one viral early gene and the one or more Adenoviral late genes can be regulated by the same system. In an embodiment, the at least one viral early gene and the one or more Adenoviral late genes can be regulated by different systems.

In some embodiments, regulation of the at least one viral early genes and the one or more viral late genes is accomplished using transcriptional induction, however other methods of regulating genes are possible using the systems disclosed herein. For example, regulation of gene expression for the at least one viral early gene and the one or more viral late genes can be accomplished by one of 1) alteration of gene structure: site-specific recombinases can activate gene expression by removing inserted sequences between the promoter and the gene; 2) changes in transcription: either by induction (covered) or by relief of inhibition; 3) changes in mRNA stability, by specific sequences incorporated in the mRNA or by siRNA; 4) changes in translation, by sequences in the mRNA; or a combination thereof.

It should be understood that the Adenovirus late genes can be from any Adenovirus serotype and with any naturally occurring or artificially selected tropism. Adenoviral serotypes differ in their natural tropism and immunogenicity. The various serotypes of Adenovirus have been found to differ in at least their capsid proteins (e.g., penton-base and hexon proteins), proteins responsible for cell binding (e.g., fiber proteins), and proteins involved in Adenovirus replication. These differences in tropism and capsid proteins among serotypes have led to the many research efforts aimed at redirecting the Adenovirus tropism by modification of the fiber proteins and immune responses by modification of hexon and penton proteins. It has been found that the Adenovirus late genes products code for the penton-base, hexon proteins and the fiber proteins. In an embodiment, natural variations in the late genes that encode for the penton-base, hexon proteins and/or the fiber proteins, affect the serotype (immune response) and/or tropism. In an embodiment, engineered variations in the late genes that encode for the penton-base, hexon proteins and/or the fiber proteins, affect the serotype and/or tropism.

A change in serotype can mitigate immune reactions. The epitopes located on the hexon protein of the Adenovirus provide the basis for the classification of Adenoviruses into the 51 serotypes known to date (*Journal of Virology*, October 2005; 79(20): 12635-12642). In an embodiment, the Adenovirus late genes include naturally occurring hexon gene variants, thus affecting the Adenovirus serotype. In an embodiment, the Adenovirus late genes are chimeric, where the hexon gene of one Adenovirus serotype are replaced with the hexon gene of another Adenovirus serotype. Such chimeric Adenovirus vectors have been engineered, for example, by replacing the Ad5 hexon gene with the hexon gene of A3 to create an Ad5/H3 vector (*Journal of Virology*, December 2002; 76(24): 12775-12782).

In an embodiment, the Adenovirus late genes include modifications to the penton base and/or fiber protein, altering the tropism of the Adenovirus. For example, Ad5 vectors having capsid mutations or pseudotyped with the short fiber from serotype 41 (Ad41s) have been found to mediate very low liver transduction (*Molecular Therapy*, August 2004; 10(2): 344-354). Similarly, it has been shown that when chimeric fiber proteins in which the head domains of Ad5 and Ad3 are exchanged, the chimeric fiber containing the Ad5 fiber head domain blocked the binding of Ad5 fiber but not Ad3 fiber, and the chimeric fiber containing the Ad3 fiber head blocked the binding of labeled Ad3 fiber but not Ad5 fiber (*Journal of Virology*, May 1995; 69(5): 2850-2857). Also, when an Adenovirus vector containing chimeric fibers composed of the tail and shaft domains of Adenovirus serotype 5 and the knob domain of serotype 3 were generated, the receptor recognition profile of the virus containing the fiber chimera was altered (*Journal of Virology*, October 1996; 70(10): 6839-6846).

In an embodiment, the Adenovirus late genes include selected mutations to the penton base and/or fiber protein, altering the tropism of the Adenovirus. For example, Ad5 vectors having capsid mutations or pseudotyped with the short fiber from serotype 41 (Ad41s) have been found to mediate very low transduction to liver cells (*Molecular Therapy*, August 2004; 10(2): 344-354). A fiber mutant, F/K20, that has a linker and a stretch of 20 lysine residues added at the C terminus of the fiber, showed a remarkably enhanced efficiency in genetic transduction of human glioma cells (*Human Gene Therapy*, 1998; 9(17): 2503-251). Epithelial and endothelial cells expressing the primary Coxsackie virus B Adenovirus (Ad) receptor (CAR) and integrin coreceptors are natural targets of human Ad infections. The fiber knob of Adenoviral A, C, D, E and F Ad serotypes binds CAR by mimicking the CAR-homodimer interface, and the penton base containing arginine-glycine-aspartate (RGD) motifs binds with low affinity to $\alpha v$ integrins inducing cell activation. Researchers generated seven different genetically modified Ad vectors with RGD sequences inserted into the HI loop of fiber knob. All mutants bound and infected CAR and $\alpha v$ integrin-positive epithelial cells with equal efficiencies. However, the mutant Adenoviruses containing two additional cysteines, both N and C terminals of the RGD sequence (RGD-4C), were uniquely capable of transducing CAR-less hematopoietic and nonhematopoietic human tumor cell lines and primary melanoma cells (*Gene Therapy*, 2003; (10): 1643-1653).

In spite of its broad host range, Adenovirus type 5 (Ad5) transduces a number of clinically relevant tissues and cell types inefficiently, mostly because of low expression of the coxsackievirus-Adenovirus receptor (CAR). To improve gene transfer to such cells, researchers modified the Ad5 fiber knob to recognize novel receptors. The researchers expressed a functional Ad5 fiber knob domain on the capsid of phage and employed this display system to construct a large collection of ligands in the HI loop of the Ad5 knob. Panning this library on the CAR-negative mouse fibroblast cell line NIH 3T3 resulted in the identification of three clones with increased binding to these cells. Adenoviruses incorporating these ligands in the fiber gene transduced NIH 3T3 cells 2 or 3 orders of magnitude better than the parent vector. The same nonnative tropism was revealed in other cell types, independently of CAR expression. These Ad5 derivatives proved capable of transducing mouse and human primary immature dendritic cells with up to 100-fold increased efficiency. (*Journal of Virology*, October 2003; 77(20): 11094-11104).

In an embodiment, the Adenovirus late genes include peptide or molecular adaptors that target Adenoviral late genes to selective tissue "addresses", altering the tropism of the Adenovirus. For example, researchers linked the Fab fragments of monoclonal antibodies that bind to Adenovirus type 5 (Ad5) to a synthetic lung-homing peptide (GFE-1 peptide) and tested the ability of the resulting bispecific conjugate to retarget Ad5. Cells that express the receptor for the GFE-1 peptide and are resistant to Ad5 infection were sensitized to recombinant Ad5 vectors in the presence of the Fab-GFE adaptor (*Human Gene Therapy*, Sep. 20, 2000: 11(14): 1971-1981). Other researchers have designed ligands corresponding to prototypes of the most represented families of phagotopes recovered from intracellular phages, and individually inserted these ligands into Ad5-green fluorescent protein (GFP) (AdGFP) vectors at the extremities of short fiber shafts (seven repeats [R7]) terminated by scissile knobs. Results validated the concept of detargeting and retargeting Ad vectors via a deknobbing system and redirecting Ad vectors to an alternative endocytic pathway via a peptide ligand inserted in the fiber shaft domain (*Journal of Virology*, July 2004; 78(13): 7227-7247). Still others have tested the efficiency of human Adenovirus serotype 5 (Ad5) transgene delivery on several human and animal cell lines in vitro, by using a bimodular 35-mer oligopeptide carrying two peptide domains with different ligand specificities. One domain mimicked the fiber knob-binding region of the alpha $_2$ domain of human MHC1 molecules (MH20), and the other corresponded to the gastrin-releasing peptide (GRP). Two synthetic peptides with different configurations were analyzed in Ad-mediated gene transfer assays using Ad5Luc3 vector carrying the luciferase reporter gene. One peptide (GRP-MH20) had the GRP domain on the N-terminal side of MH20, while the other (MH20-GRP), the C-terminally amidified GRP, was on the C-terminal side of MH20. The GRP-MH20 peptide, but not MH20-GRP, was capable of enhancing luciferase gene delivery to Ad-susceptible cells in a GRP receptor-dependent manner More importantly, GRP-MH20 could also confer susceptibility to Ad infection to normal or cancer cells that lack fiber receptors for the virus. The data suggested that GRP receptors could function efficiently as alternative attachment receptors for Ad5, but that Ad5 bound to GRP receptors still depended, at least partially, on the penton base-mediated endocytotic pathway for subsequent cell entry (*Human Gene Therapy*, Nov. 10, 1999; 10(16): 2577-2586) and (*Virus Research*, March 2001; 73(2): 145-152).

Regulation of Gene Expression

An inducible system is off unless there is the presence of some molecule (called an inducer) that allows for gene expression. The molecule is said to "induce expression". The manner in which this happens is dependent on the control mechanisms as well as differences between prokaryotic and eukaryotic cells. A repressible system is on except in the presence of some molecule (called a corepressor) that suppresses gene expression. The molecule is said to "repress expression". The manner in which this happens is dependent on the control mechanisms as well as differences between prokaryotic and eukaryotic cells.

Gene regulation systems/control systems for gene expression useful in practing the present invention include, but are not limited to, the Tet System, the ecdysone receptor-based RheoSwitch mammalian inducible expression system (Ecdysteroid/muristerone/retinoid X receptor), FK1012/

FK506-induced system, the Rapamycin/FKBP12/FRAP system, RU486 (mifepristone)/GLVP/PR-LBDΔ system, Cytochrome P-450, Gal4, Streptogramin/macrolide induced system, Acylated homoserine lactone (AHL) induced system and UTR aptamers. In an embodiment, the present invention uses the Tet System with the genes encoding for VP16-TetR fusion protein as Transcriptional Activator, TetO as promoter, and at least one of tetracycline (tc) or doxycycline (dox) as the inducer.

Late Genes Expressed under Inducible Promoter

A major area of interest concerns the problem that most gene-based modification approaches are functionally equivalent to digital switches: the genes exist either in a wild-type or in a modified state, with little possibility of a partial modification or of reversibility. To address this, many studies have investigated inducible-promoter systems. These systems use a regulating agent (including small molecules such as tetracycline, peptide and steroid hormones, nerotransmitters, and environmental factors such as heat, and osmolarity) to induce or to silence a gene. Such systems are analog in the sense that the response is graduated, being dependent on the concentration of the regulating agent. Also, such systems are reversible with the withdrawal of the regulating agent. While a number of approaches have been investigated, including cold-inducible gene regulation systems, and single regulated promoters (such as those regulated by heavy metals, heat shock, or steroids), finer regulatory control has been achieved by binary systems composed of an effector molecule (the regulator) and a target transgene. A prototypic system is the "tetracycline-responsive system" or "Tet-OFF system" originally developed by Gossen and Bujard (*Proc. Natl. Acad. Sci. USA* 1992; 89: 5547-5551). The Tet-OFF system uses an effector protein composed of a fusion between the *Escherichia coli* tetracycline-repressor protein (TetR) and the Herpes simplex VP16 trans activation domain (VP16-TetR fusion protein). In the absence of tetracycline (tc) or doxycycline (dox), the fusion protein binds the 19-bp operator sequence, TetO. In the presence of tc or dox, the repressor dissociates from TetO and activation is lost.

Late Genes Regulated by Repressed Promoter

Another system referred to as the "reverse tetracycline" or the "Tet-ON" system, works by activating transcription when tc, dox or anhydrotetracycline is present and was developed by Gossen et al. (*Science*, 1995; 268: 1766-1769). The Tet-On system uses a mutated TetR such that, for example, binding of dox or tc induces DNA binding rather than abrogating it, rTetR. VP16-rTetR fusion is then an activated only in the presence of tc, dox or anhydro-tc. The packaging systems disclosed herein use the "Tet-ON" system.

FIG. 5 is a diagrammatic representation showing an embodiment of a co-transfection system comprising a fully-deleted Adenoviral vector construct (FDV), a packing construct (pPack), and an Adenovirus packaging cell (PC) for producing encapsidated encapsidated fully-deleted Adenovirus-based gene transfer vectors (GDVs) without helper Adenovirus. FIG. 6 is a diagrammatic representation showing an embodiment of a transfection system comprising a fully-deleted Adenoviral vector construct (FDV) and an Adenovirus packaging cell (PC) for producing encapsidated fully-deleted Adenovirus-based gene transfer vectors (GDVs) without helper Adenovirus. Table 4 lists various embodiments of a system (including a PC and at least one construct (a FDV or a pPack) to propagate GDVs of the present disclosure. At least twenty-eight (28) embodiments of systems for propagating GDVs of the present invention are contemplated, as summarized in Table 4 below. A method for propagating an adenoviral vector includes (a) providing an Adenovirus packaging cell line; (b) transfecting a fully-deleted Adenoviral vector construct into the cell line; and optionally (c) transfecting a packaging construct into the cell line, wherein the fully-deleted Adenoviral vector construct and optionally the packaging construct can transfect the Adenovirus packaging cell line resulting in the encapsidation of a fully-deleted Adenoviral vector independent of helper Adenovirus.

TABLE 4

Embodiments of Systems for Propagating GDVs
A system of the present invention includes
a PC, a FDV, and optionally a pPack.

| If the PC is | then the FDV is | and optionally the pPack is: |
| --- | --- | --- |
| PC1, | FDV1, | pPack1. |
| PC2, | FDV1, | pPack2. |
| PC1, | FDV2, | pPack3. |
| PC2, | FDV2, | pPack4. |
| PC1, | FDV1, | pPack5. |
| PC2, | FDV1, | pPack6. |
| PC1, | FDV2, | pPack7. |
| PC2, | FDV2, | pPack8. |
| PC3, | FDV1, | pPack9. |
| PC4, | FDV1, | pPack10. |
| PC3, | FDV2, | pPack11. |
| PC4, | FDV2, | pPack12. |
| PC5, | FDV3, | None. |
| PC6, | FDV3, | None. |
| PC7, | FDV4, | None. |
| PC8, | FDV4, | None. |
| PC9, | FDV3, | None. |
| PC10, | FDV3, | None. |
| PC11, | FDV4, | None. |
| PC12, | FDV4, | None. |
| PC13, | FDV1, | None. |
| PC14, | FDV1, | None. |
| PC15, | FDV1, | None. |
| PC16, | FDV1, | None. |
| PC17, | FDV3, | None. |
| PC18, | FDV3, | None. |
| PC19, | FDV3, | None. |
| PC20, | FDV3, | None. |

A GDV propagated by a system of the present disclosure includes both Adenoviral inverted terminal repeats (LITR and RITR) separated by approximately 28 to 37 kb, the viral packaging signal (Ψ), and at least one DNA insert (all or a fragment of at least one gene of interest (GOI)) which comprises a gene sequence encoding a protein of interest. No viral structural genes are contained in the GDV. In an embodiment, a GOI can be a therapeutic gene, immunomodulatory gene, a vaccine gene or a combination thereof. In an embodiment, a GDV of the present disclosure expresses an immunomodulatory gene. In an embodiment, the immunomodulatory gene is a gene encoding human CD8. In an embodiment, a GDV of the present disclosure expresses a therapeutic gene. In an embodiment, the therapeutic gene is an interleukin. In an embodiment, the therapeutic gene is factor VIII. In some embodiments of the present disclosure, a GDV comprises one or more transgenes encoding therapeutic molecules of interest along with a CD8 polypeptide described herein.

Administration of GDVs

One skilled in the art will appreciate that suitable methods of administering a GDV of the present disclosure to an animal for therapeutic purposes, e.g., gene therapy, immunosuppressive therapy, vaccination, and the like (see, for example, Rosenfeld et al., Science, 252, 431 434 (1991), Jaffe et al., Clin. Res., 39(2), 302A (1991), Rosenfeld et al., Clin. Res., 39(2), 311A (1991), Berkner, BioTechniques, 6, 616 629 (1988)), are available, and, although more than one route can be used to administer the GDV, a particular route can provide a more immediate and more effective reaction than another route. Pharmaceutically acceptable excipients are also well-known to those who are skilled in the art, and are readily available. The choice of excipient will be determined in part by the particular method used to administer the GDV. Accordingly, there is a wide variety of suitable formulations of the GDVs of the present invention. The following formulations and methods are merely exemplary and are in no way limiting. However, oral, injectable and aerosol formulations are preferred.

Formulations suitable for oral administration can consist of (a) liquid solutions; (b) capsules, sachets or tablets; (c) suspensions in an appropriate liquid; and (d) suitable emulsions. In an embodiment, the GDVs of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. The GDVs of the present invention may also be formulated as pharmaceuticals for non-pressured preparations such as in a nebulizer or an atomizer. Formulations suitable for parenteral administration include aqueous and non-aqueous, isotonic sterile injection solutions, which can comprise anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The dose administered to an animal, particularly a human, in the context of the present invention will vary with the gene or other sequence of interest, the composition employed, the method of administration, and the particular site and organism being treated. The dose should be sufficient to effect a desirable response, e.g., therapeutic or immune response, within a desirable time frame.

Hence, one or more of the following routes may administer the GDVs of the present disclosure: oral administration, injection (such as direct injection), topical, inhalation, parenteral administration, mucosal administration, intramuscular administration, intravenous administration, subcutaneous administration, intraocular administration or transdermal administration. In an embodiment, encapsidated FDVs of the present disclosure are administered via injection. In an embodiment, GDVs of the present disclosure are administered topically. In an embodiment, GDVs of the present disclosure are administered by inhalation. In an embodiment, GDVs of the present disclosure are administered by one or more of: parenteral, mucosal, intramuscular, intravenous, subcutaneous, intraocular or transdermal administration means, and are formulated for such administration.

Typically, a physician will determine the actual dosage of GDVs that will be most suitable for an individual subject and it will vary with the age, weight and response of the particular patient and severity of the condition. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The dose administered to an animal, particularly a human, in the context of the present invention will vary with the therapeutic transgene of interest and/or the nature of the immunomodulatory molecule, the composition employed, the method of administration, and the particular site and organism being treated. However, preferably, a dose corresponding to an effective amount of a GDV is employed. An "effective amount" is one that is sufficient to produce the desired effect in a host, which can be monitored using several end-points known to those skilled in the art. For instance, one desired effect is nucleic acid transfer to a host cell. Such transfer can be monitored by a variety of means, including, but not limited to, a therapeutic effect (e.g., alleviation of some symptom associated with the disease, condition, disorder or syndrome being treated), or by evidence of the transferred gene or coding sequence or its expression within the host (e.g., using the polymerase chain reaction, Northern or Southern hybridizations, or transcription assays to detect the nucleic acid in host cells, or using immunoblot analysis, antibody-mediated detection, or particularized assays to detect protein or polypeptide encoded by the transferred nucleic acid, or impacted in level or function due to such transfer). These methods described are by no means all-inclusive, and further methods to suit the specific application will be apparent to the ordinary skilled artisan. In this regard, it should be noted that the response of a host to the introduction of a GDV can vary depending on the dose of virus administered, the site of delivery, and the genetic makeup of the GDV as well as the transgene and the means of inhibiting an immune response.

Generally, to ensure effective transfer of the GDVs of the present invention, it is preferable that about 1 to about 5,000 copies of the GDV according to the invention be employed per cell to be contacted, based on an approximate number of cells to be contacted in view of the given route of administration, and it is even more preferable that about 3 to about 300 pfu enter each cell. However, this is merely a general guideline, which by no means precludes use of a higher or lower amount, as might be warranted in a particular application, either in vitro or in vivo. Similarly, the amount of a means of inhibiting an immune response, if in the form of a composition comprising a protein, should be sufficient to inhibit an immune response to the recombinant GDV comprising the transgene. For example, the actual dose and schedule can vary depending on whether the composition is administered in combination with other pharmaceutical compositions, or depending on interindividual differences in pharmacokinetics, drug disposition, and metabolism. Similarly, amounts can vary in in vitro applications, depending on the particular cell type targeted or the means by which the GDV is transferred. One skilled in the art easily can make any necessary adjustments in accordance with the necessities of the particular situation.

Immunosuppressive Therapy for Allogeneic Transplantation

A major unmet need in transplant immunobiology is the development of more specific immune inhibition strategies directed exclusively to the alloantigen response. Ideally, such strategies would inhibit allorejection without the need for continuous general pharmacologic immunosuppression and its attendant complications and costs. Achieving specific immunological tolerance to such alloantigens can improve transplant longevity and quality of life for the recipient, and at the same time considerably improve the cost effectiveness of transplant therapy. The present invention achieves these heretofore elusive goals.

The veto effect mediated by targeted expression of CD8α can effectively and specifically suppress responding CD4+ T cells (MHC class II-restricted) as well as CD8+ T cells (MHC class I-restricted), therefore both the cellular and humoral components of the immune response directed against alloantigens can be inhibited. Adenoviral vectors are particularly suited for transduction of the CD8 gene to allogeneic cells/tissues for transplantation because they infect a wide range of cell and tissues with high efficiency and because the transduced DNA is expressed transiently and not permanently integrated into the genome of the transduced cells. For CD8 mediated veto immune protection of allogeneic transplants based on Adenoviral vector transduction of CD8 to the allogeneic transplant, it is desirable that the Adenoviral vector carry no Adenoviral genes, as the consequence would be long-term immune non-responsiveness to the base Adenovirus.

In an embodiment, the GDVs of the present disclosure are engineered to transform cells and tissues into specifically immune suppressive moieties. In an embodiment, the cells are human keratinocytes and a skin transplant can be engineered to treat, for example, a burn victim or an individual with a diabetic ulcer. In an embodiment, the cells are nonhuman primate hepatocytes and a hepatocyte transplant can be engineered to treat, for example, end-stage liver disease or a gene defect. In an embodiment, the cells are kidney cells, for example from porcine or a nonhuman primate, and a kidney transplant can be engineered to treat, for example, end-stage kidney disease. A GDV vetoes rejection by inducing suicide (apoptosis) specifically of lymphocytes with the ability to reject transplants. In an embodiment, the GDVs of the present disclosure find use in immunosuppressive therapy for allogeneic transplants, wherein the transplant is selected from one of pancreatic islets, hepatocytes or keratinocytes.

In an embodiment, methods and compositions are provided for specifically inhibiting an alloantigen response to donor and/or host antigens, depending on the nature of the allograft, in order to prolong the survival of allogeneic grafts and protect the health of the transplant recipient. Thus, using the compositions and methods described herein one may selectively inhibit allorejection activity directed to either donor or host antigens without the need for chronic administration of general immunosuppressive agents, effectively resulting in specific immunological tolerance to donor tissue, organs and/or cells.

In one aspect, methods for specifically inhibiting immune responses to alloantigens are provided, comprising contacting a target cell expressing at least one such alloantigen with a GDV encoding all or a functional portion of a CD8 polypeptide, preferably a human CD8 polypeptide, still more preferably the human CD8 α-chain, whereby the CD8 polypeptide is expressed by the target cell and whereby the alloimmune response directed against the alloantigen is specifically inhibited. In one embodiment, the alloantigen comprises a donor alloantigen and the target cell comprises an allograft cell. In an alternative embodiment, the alloantigen comprises a recipient alloantigen and the target cell comprises a recipient cell. In a further embodiment, the alloimmune response includes both a humoral component and a cellular component. In a preferred embodiment, the alloimmune response is effectively inhibited without the need for general immunosuppressive agents. By "nucleic acid molecules encoding CD8", and grammatical equivalents thereof is meant the nucleotide sequence of human CD8 as well as nucleotide sequences having at least about 80% sequence identity, usually at least about 85% sequence identity, preferably at least about 90% sequence identity, more preferably at least about 95% sequence identity and most preferably at least about 98% sequence identity.

In another aspect, methods for specifically inhibiting immune responses to donor alloantigen are provided, comprising conditioning donor allograft cells in vivo or ex vivo to express all or a functional portion of a CD8 polypeptide, preferably a human CD8 polypeptide, still more preferably the human CD8 α-chain. In one embodiment, the conditioning step comprises contacting the allograft cells in vivo or ex vivo with a GDV encoding all or a functional portion of a CD8 polypeptide, whereby the CD8 polypeptide is expressed by allograft cells and whereby the recipient immune response directed against donor alloantigen is specifically inhibited. Preferably, both the cellular and humoral components of the recipient alloimmune response are effectively and specifically inhibited without the need for general immunosuppressive agents.

In another aspect, methods for specifically inhibiting immune responses to recipient alloantigen are provided, comprising in vivo conditioning of recipient cells to express all or a functional portion of a CD8 polypeptide, preferably a human CD8 polypeptide, still more preferably the human CD8α-chain. Preferred recipient cells for the subject conditioning step include those found in the recipient tissues and organs most at risk of a GVHD immune response such as, e.g., liver, skin and intestinal tract. In one embodiment, the conditioning step comprises contacting such recipient cells in vivo with a GDV encoding all or a functional portion of a CD8 polypeptide, whereby the CD8 polypeptide is expressed by the cells and whereby the donor immune response directed against recipient alloantigen is specifically inhibited. Preferably, the donor alloimmune response is effectively and specifically inhibited without the need for general immunosuppressive agents.

Also provided are methods for prolonging the survival of an allograft in a recipient, comprising conditioning the allograft cells in vivo or ex vivo to express all or a functional portion of a CD8 polypeptide, preferably a human CD8 polypeptide, still more preferably the human CD8α-chain. In one embodiment, the conditioning step comprises contacting the allograft cells in vivo or ex vivo with a GDV encoding all or a functional portion of a CD8 polypeptide, wherein the CD8 polypeptide is expressed by allograft cells and whereby the survival time of the allograft in the recipient is extended. Preferably, the conditioning step is performed prior to or contemporaneously with transplantation of the allograft. Still more preferably, the conditioning step is performed ex vivo prior to transplantation of the allograft, or in vivo in the donor prior to or contemporaneous with harvesting of the allograft. Most preferably, use of the subject methods is effective to induce stable immunological tolerance to the allograft, such that chronic administration of general immunosuppressive agents will not be required.

Also provided are methods for suppressing GVHD in a recipient, comprising in vivo conditioning of recipient cells at risk of a GVHD immune response to express all or a functional portion of a CD8 polypeptide, preferably the human CD8α-chain. In one embodiment, the conditioning step comprises contacting recipient cells in vivo with a GDV encoding all or a functional portion of a CD8 polypeptide, whereby the CD8 polypeptide is expressed by the cells and whereby the GVHD immune response raised against the recipient cells by transplanted donor T cells is suppressed. Preferably, the conditioning step is performed contemporaneously with or subsequent to transplantation of the allograft. Still more preferably, the conditioning step is performed in vivo in the recipient after transplantation of the allograft. Most preferably, use of the subject methods is effective to induce stable immunological tolerance of transplanted donor T cells to recipient alloantigen, such that chronic administration of general immunosuppressive agents is not needed.

Preferred CD8 polypeptides for use in the subject methods and compositions will generally comprise the CD8α-chain, more preferably the extracellular domain of the CD8α-chain, and still more preferably the Ig-like domain of the CD8α-chain. In alternative preferred embodiments, the CD8 polypeptides may comprise or consist essentially of the extracellular domain of the CD8α-chain and a transmembrane domain, or more preferably the Ig-like domain of the CD8α-chain and a transmembrane domain. In a particularly preferred embodiment, the transmembrane domain is the transmembrane domain of the CD8α-chain. Given the nature of the subject expression methods, as well as the apparent inadequacies of the prior art soluble forms of CD8α-chain described above, the presence of the CD8α-chain transmembrane domain or a suitable alternative transmembrane region is deemed essential.

In a further aspect, the present invention provides improved transplant allografts capable of specifically and effectively inhibiting a recipient immune response raised against them. In one embodiment, the improved transplant allograft comprises allograft cells modified to express a CD8 polypeptide, preferably a human CD8 polypeptide, still more preferably the human CD8α-chain. As discussed herein, the CD8 polypeptide may comprise or alternatively consist essentially of the extracellular domain of the CD8α-chain and a transmembrane domain, or the Ig-like domain of the CD8α-chain and a transmembrane domain. The transmembrane domain may be that of the CD8α-chain or may be another advantageously-selected transmembrane domain. Modification of allograft cells may be achieved with a liposome-mediated nucleic acid transfer vehicle, a viral-mediated nucleic acid transfer vehicle, and the like, as disclosed herein.

In a still further aspect, an improved organ preservation solution is provided, comprising a GDV encoding a CD8 polypeptide. Thus, in a preferred embodiment, the invention provides an improved organ preservation solution comprising a GDV comprising a nucleic acid encoding for a CD8 polypeptide, preferably a human CD8 polypeptide, and most preferably the human CD8α-chain. In another preferred embodiment, the improved organ preservation solution comprises a GDV comprising a nucleic acid encoding for the extracellular domain of a CD8α-chain and a transmembrane domain, or alternatively the Ig-like domain of the CD8α-chain and a transmembrane domain. In a particularly preferred embodiment, the transmembrane domain is the CD8α-chain transmembrane domain. In further embodiments, the GDV may further comprise a nucleic acid encoding for an anti-inflammatory molecule such as, e.g., heme oxygenase.

In a broader aspect, methods are provided for specifically inhibiting a host immune response to a target cell-specific antigen, comprising conditioning the target cell in vivo or ex vivo to express all or a functional portion of a CD8 polypeptide, more preferably the human CD8 polypeptide, still more preferably the human CD8α-chain, wherein the CD8 polypeptide is expressed by the target cell and whereby an immune response directed against such antigen is specifically inhibited. In one embodiment, the target cell-specific antigen is an alloantigen. In another embodiment, the target cell-specific antigen is an autoantigen. In a preferred embodiment, the conditioning step comprises contacting the target cell in vivo or ex vivo with a GDV encoding the CD8 polypeptide.

In a still further aspect, methods for preventing the development of and for treating autoimmune diseases are provided, comprising administering to a patient in need thereof a therapeutic composition comprising a GDV encoding all or a functional portion of a CD8 polypeptide, preferably a human CD8 polypeptide, still more preferably the CD8α-chain, wherein expression of the CD8 polypeptide by a contacted target cell specifically inhibits an autoreactive immune response directed against the target-cell specific autoantigens.

In order to effect expression of the immunomodulatory molecule (e.g. CD8α-chain) and/or additional therapeutic proteins, the GDVs must be delivered into a cell. This delivery may be accomplished in vitro, as in laboratory procedures for transforming cells lines, or in vivo or ex vivo, as in the treatment of certain disease states. Once the GDV has been delivered into the cell the nucleic acid encoding the desired oligonucleotide or polynucleotide sequences may be positioned and expressed at different sites. In certain embodiments, the nucleic acid encoding the construct may be stably integrated into the genome of the cell. This integration may be in the specific location and orientation via homologous recombination (gene replacement) or it may be integrated in a random, non-specific location (gene augmentation). In further and preferred embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle.

Although the above examples describe a GDV encoding an immunomodulatory gene encoding all or a functional portion of a CD8 polypeptide, it should be understood that additional immunomodulatory genes encoding immunomodulatory molecules are contemplated, including, but not limited to, IL-10, TGF-beta, IL-2, IL-12, IL-15, IL-18, IL-4 and GM-CSF.

Gene Therapy for Gene and Protein Expression

Gene therapy generally involves the introduction into cells of therapeutic genes, also known as transgenes, whose expression results in amelioration or treatment of genetic disorders. The therapeutic genes involved may be those that encode proteins, structural or enzymatic RNAs, inhibitory products such as antisense RNA or DNA, or any other gene product. Expression is the generation of such a gene product or the resultant effects of the generation of such a gene product. Thus, enhanced expression includes the greater production of any therapeutic gene or the augmentation of that product's role in determining the condition of the cell, tissue, organ or organism.

In general, the instant invention relates to GDVs for transferring selected genetic material of interest (e.g., DNA or RNA) to cells in vivo. The invention also relates to methods of gene therapy using the disclosed GDVs and genetically engineered cells produced by the method. Diseases that may be treated by the present invention include, but are not limited to, Hemophilia A (with Factor VIII), Parkinson's Disease, Congestive Heart Failure and Cystic Fibrosis. In an embodiment, a GDV of the present disclosure carrying at least a fragment of a gene of interest can infect the myocardium in vivo following intracardiac injection. In an embodiment, a GDV of the present disclosure carrying at least a fragment of the CFTR gene can be introduced in situ into the lungs of a Cystic Fibrosis patient by aerosol inhalation. In an embodiment, a GDV of the present disclosure carrying at least a fragment of a gene coding for Factor VIII can be introduced in situ into a muscle in the arm of a patient with Hemophilia A. In an embodiment, a GDV of the present disclosure carrying at least a fragment of the ADA gene can be transduced into a subpopulation of bone marrow cells ex vivo, and then the transduced bone marrow cells can be transplanted into a patient suffering from Adenosine deaminase (ADA) deficiency.

The particular therapeutic gene encoded by a GDV of the present disclosure is not limiting and includes those useful for various therapeutic and research purposes, as well as reporter genes and reporter gene systems and constructs useful in tracking the expression of transgenes and the effectiveness of Adenoviral and Adenoviral vector transduction. Thus, by way of example, the following are classes of possible genes whose expression may be enhanced by using a GDV of the present disclosure: developmental genes (e.g. adhesion molecules, cyclin kinase inhibitors, Wnt family members, Pax family members, Winged helix family members, Hox family members, cytokines/lymphokines and their receptors, growth or differentiation factors and their receptors, neurotransmitters and their receptors), oncogenes (e.g. ABL1, BLC1, BCL6, CBFA1, CBL, CSFIR, ERBA, ERBB, EBRB2, ETS1, ETS1, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3 and YES), tumor suppresser genes (e.g. APC, BRCA1, BRCA2, MADH4, MCC, NF1, NF2, RB1, TP53 and WT1), enzymes (e.g. ACP desaturases and hycroxylases, ADP-glucose pyrophorylases, ATPases, alcohol dehycrogenases, amylases, amyloglucosidases, catalases, cellulases, cyclooxygenases, decarboxylases, dextrinases, esterases, DNA and RNA polymerases, hyaluron synthases, galactosidases, glucanases, glucose oxidases, GTPases, helicases, hemicellulases, hyaluronidases, integrases, invertases, isomersases, kinases, lactases, lipases, lipoxygenases, lyases, lysozymes, pectinesterases, peroxidases, phosphatases, phospholipases, phophorylases, polygalacturonases, proteinases and peptideases, pullanases, recombinases, reverse transcriptases, topoisomerases, xylanases), reporter genes (e.g. Green fluorescent protein and its many color variants, luciferase, CAT reporter systems, Beta-galactosidase, etc.), blood derivatives, hormones, lymphokines (including interleukins), interferons, TNF, growth factors, neurotransmitters or their precursors or synthetic enzymes, trophic factors (such as BDNF, CNTF, NGF, IGF, GMF, aFGF, bFGF, NT3, NT5, and the like), apolipoproteins (such as ApoAI, ApoAIV, ApoE, and the like), dystrophin or a minidystrophic, tumor suppressor genes (such as p53, Rb, Rap1A, DCC, k-rev, and the like), genes coding for factors involved in coagulation (such as factors VII, VI, IX, and the like), suicide genes (such as thymidine kinase), cytosine deaminase, or all or part of a natural or artificial immunoglobulin (Fab, ScFv, and the like). Other examples of therapeutic genes include fus, interferon α, interferon β, interferon γ, and ADP (Adenoviral death protein).

The therapeutic gene can also be an antisense gene or sequence whose expression in the target cell enables the expression of cellular genes or the transcription of cellular mRNA to be controlled. Such sequence can, for example, be transcribed in the target cell into RNAs complementary to cellular mRNAs. The therapeutic gene can also be a gene coding for an antigenic peptide capable of generating an immune response in man. In this particular embodiment, the disclosure makes it possible to produce vaccines enabling humans to be immunized, in particular against microorganisms, viruses and cancer.

Various enzyme genes are also considered therapeutic genes. Particularly appropriate genes for expression include those genes that are thought to be expressed at less than normal level in the target cells of the subject mammal Examples of particularly useful gene products include, but are not limited to, carbamoyl synthetase I, ornithine transcarbamylase, arginosuccinate synthetase, arginosuccinate lyase, and arginase. Other desirable gene products include fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione.beta.-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, β-glucosidase, pyruvate carboxylase, hepatic phosphorylase, phosphorylase kinase, glycine decarboxylase (also referred to as P-protein), H-protein, T-protein, Menkes disease copper-transporting ATPase, and Wilson's disease copper-transporting ATPase. Other examples of gene products include, but are not limited to, cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase and human thymidine kinase. Hormones are another group of genes that may be used in the Adenoviral-derived vectors described herein. Included are growth hormone, prolactin, placental lactogen, luteinizing hormone, follicle-stimulating hormone, chorionic gonadotropin, thyroid-stimulating hormone, leptin, adrenocorticotropin (ACTH), angiotensin I and II, β-endorphin, β-melanocyte stimulating hormone (β-MSH), cholecystokinin, endothelin I, galanin, gastric inhibitory peptide (GIP), glucagon, insulin, lipotropins, neurophysins, somatostatin, calcitonin, calcitonin gene related peptide (CGRP), β-calcitonin gene related peptide, hypercalcemia of malignancy factor (1-40), parathyroid hormone-related protein (107-139) (PTH-rP), parathyroid hormone-related protein (107-111) (PTH-rP), glucagon-like peptide (GLP-1), pancreastatin, pancreatic peptide, peptide YY, PHM, secretin, vasoactive intestinal peptide (VIP), oxytocin, vasopressin (AVP), vasotocin, enkephalinamide, metorphinamide, alpha melanocyte stimulating hormone (alpha-MSH), atrial natriuretic factor (5-28) (ANF), amylin, amyloid P component (SAP-1), corticotropin releasing hormone (CRH), growth hormone releasing factor (GHRH), luteinizing hormone-releasing hormone (LHRH), neuropeptide Y, substance K (neurokinin A), substance P and thyrotropin releasing hormone (TRH). Other classes of genes that are contemplated to be inserted into the GDVs of the present disclosure include, but are not limited to, interleukins and cytokines, including interleukin 1 (IL-1), IL-2, IL-3, IL4, IL-5, IL-6, IL-7, IL-8, IL-9, IL-10, IL-11 IL-12, GM-CSF and G-CSF.

Diseases that may be treated by the present invention include, but are not limited to, prevalent genetic diseases such as Phenylketonuria (phenylalanine-L-monooxygenase), adenosine deaminase deficiency, cystic fibrosis (cystic fibrosis conductance regulator), Parkinson's disease, ornithine caramyltransferase deficiency (OTC), hemophilias (Factor IX-deficiency, Factor VIII-deficiency), Tay-Sachs (N-acetyl-hexosamimidase A), cystic fibrosis, which would involve the replacement of the cystic fibrosis conductance regulator gene, and other lipid storage diseases. In addition, the gene encoding erythropoietin (EPO) can used. A FDHIV of the present disclosure is free of Adenoviral early region and late genes.

A GDV of the present disclosure can be used for treatment of hyperproliferative disorders such as rheumatoid arthritis or restenosis by transfer of genes encoding angiogenesis inhibitors or cell cycle inhibitors. Transfer of prodrug activators such as the HSV-TK gene can be also be used in the treatment of hyperproliferative disorders, including cancer. In an embodiment, a GDV of the present disclosure includes a therapeutic gene sequence and a CD8 gene sequence, wherein the CD8 gene sequence is capable of preventing an immune response to the therapeutic gene sequence, as described below. Such applications include, but are not limited to, Factor VIII deficiency (Hemophilia A) where the patients do not produce any protein from the deficient gene (null alleles). In these patients, an immune response may be mounted against the product of the therapeutic gene, just as an immune response frequently occurs in Hemophilia A patients treated by injection of Factor VIII protein.

Adenovirus vectors have been used to produce recombinant proteins useful in treating diseases. However, contamination of the therapeutic recombinant proteins with Adenoviral proteins and/or Adenovirus is a continual problem. Accordingly, there is a need for systems that support growth of Adenoviral-derived vectors with reduced complement of Ad genes and/or absence of contamination with replication competent, or helper, Adenovirus. Co-ordinate expression of polypeptides for multimeric proteins can be coordinated by co-expression from an Adenoviral vector. For example the expression of equimolar amounts of immunoglobulin heavy and light chains is facilitated by co-ordinate expression from a common Adenoviral vector.

According to aspects illustrated herein, in an embodiment a protein expression protocol includes administering a GDV of the present disclosure.

Vaccine Development

In an embodiment, the invention relates to biotechnology and the development and manufacture of vaccines. The invention is particularly useful for the production of vaccines to aid in protection against viral and bacterial pathogens for vertebrates, in particular mammalians and especially humans. Vaccines of the present invention can be prophylactic (e.g. to prevent or ameliorate the effects of a future infection by any natural or "wild" pathogen), or therapeutic (e.g. vaccines against cancer).

Vaccination is the most important route of dealing with viral infections. Although a number of antiviral agents are available, typically these agents have limited efficacy. Administering antibodies against a virus may be a good way of dealing with viral infections once an individual is infected (passive immunization) and typically human or humanized antibodies do seem promising for dealing with a number of viral infections. But the most efficacious and safe way of dealing with virus infection is, and probably will be, prophylaxis through active immunizations. Active immunization is generally referred to as vaccination and vaccines comprising at least one antigenic determinant of a virus, preferably a number of different antigenic determinants of at least one virus, e.g., by incorporating in the vaccine at least one viral polypeptide or protein derived from a virus (subunit vaccines). Typically, the formats mentioned so far include adjuvants in order to enhance an immune response. This also is possible for vaccines based on whole virus, e.g., in an inactivated format. A further possibility is the use of live, but attenuated forms of the pathogenic virus. A further possibility is the use of wild-type virus, e.g., in cases where adult individuals are not in danger from infection, but infants are and may be protected through maternal antibodies and the like.

Production of vaccines is not always an easy procedure. In some cases the production of viral material is on eggs, which leads to difficulty in purifying material and extensive safety measures against contamination, etc. Also production on bacteria and or yeasts, which sometimes, but not always, is an alternative for eggs, requires many purification and safety steps. Production on mammalian cells would be an alternative, but mammalian cells used so far all require, for instance, the presence of serum and/or adherence to a solid support for growth. In the first case, again, purification and safety and e.g., the requirement of protease to support the replication of some viruses become an issue. In the second case, high yields and ease of production become a further issue.

Vaccines are still lacking for many viral diseases of great public health importance. Killed viral vaccines can be dangerous and expensive to produce, and are frequently not immunogenic. The inclusion of viral protein encoding sequences in an Adenoviral vector may circumvent these problems, however, there are challenges to creating such an Adenovirus vector. For example, there is little space in Adenovirus vectors, and the immune response to the Adenovirus vector interferes with the immune response to the vaccine protein.

An object of the present invention is therefore to provide GDVs, which are capable of a long-term maintenance in a large and increasing number of different cells of the host's body and thereby capable of providing a stable expression of the desired antigen(s). Another object of the invention is to provide GDVs, which are maintained for a long period of time in the cells that originally received the vector and transferred it to the daughter cells after mitotic cell division. Yet another object of the invention is to provide GDVs, which express in addition to the gene or genes of interest preferably only a gene necessary for a long-term maintenance in the recipient cells and thus are devoid of components that are toxic or cause symptoms of the disease to the recipient. A further object of the invention is to provide GDVs, which mimic attenuated live viral vaccines, especially in their function of multiplying in the body, without inducing any considerable signs of disease and without expressing undesired proteins, which may induce adverse reactions in a host injected with the DNA vaccine. The vaccines of the present invention comprise a GDV of the present invention or a mixture of said vectors in a suitable pharmaceutical carrier. The vaccines of the invention are formulated using standard methods of vaccine formulation to produce vaccines to be administered by any conventional route of administration, i.e. intramuscularily, intradermally and like. In specific embodiments, a GDV of the invention is used to treat and/or prevent an infectious disease and/or a condition caused by an infectious agent. Such diseases and conditions include, but are not limited to, infectious diseases caused by bacteria, viruses, fungi, protozoa, helminths, and the like.

A GDV of the present disclosure can be used for vaccine development to protect an individual against a disease by inducing immunity. One advantage of using a GDV of the present disclosure for vaccine development is that the recipient's immune response is not deflected by Ad genes. In an embodiment, a GDV of the present disclosure encodes one or more proteins and/or RNAs (angitens) from viruses of importance for human health or agriculture. In an embodiment, the vaccine is used to protect an individual against a disease by inducing immunity. In an embodiment, multiple genes of interest my be included for mulitivalent vaccines, from the same or different pathogens. In certain embodiments, the GDV further comprises one or more expression cassettes of a DNA sequence of interest. In certain embodiments, the DNA sequence of interest is that of an infectious pathogen. In certain embodiments, the infectious pathogen is a virus. In certain specific embodiments, the virus is selected from the group consisting of Human Immunodeficiency Virus (HIV), Herpex Simplex Virus (HSV), Hepatitis C Virus, Influenzae Virus, Rotavirus, Papilloma Virus, Lentivirus, Enterovirus or combinations thereof. In certain embodiments, the DNA sequence of interest is that of a bacterium. In certain embodiments, the bacterium is selected from the group consisting of *Chlamydia trachomatis, Mycobacterium tuberculosis*, and *Mycoplasma pneumonia*. In certain embodiments, the DNA sequence of interest is that of a fungal pathogen. In certain embodiments, the DNA sequence of interest is of HIV origin. In an embodiment, the vaccine is used to protect an individual against influenza virus. In an embodiment, the influenza virus is swine flu. In an embodiment, the influenza virus is avian flu. In an embodiment, the one or more proteins and/or RNAs of a GDV of the present disclosure are selected from one of hemagglutinin (HA), neuraminidase (NA), nucleocapsid (NP), $M_1$ (matrix protein), $M_2$ (ion channel), $NS_1$, $NS_2$ (NEP), lipid bilayer, PB1, PB2 or PA.

Representative viral and bacterial candidates for vaccines of the present disclosure are listed below. Genes for these vaccines are illustrated in italic.

Genetic Adjuvants interleukin-2 [IL-2], IL-12, IL-15, and IL-18) and Th2-type (IL-4 and IL-10)

GM-CSF

Viruses—Orthomyxoviruses

Influenza A: hemagglutinin (HA) and neuraminidase (NA), nucleoprotein (NP), $M_1$, $M_2$, NS1, NS2 (NEP), PA, PB1, PB1-F2 and PB2)

Influenza B

Influenza C

Viruses—Herpes Virus

Herpes simplex 1 (oral herpes)

Herpes simplex 2 (genital herpes)—84 polypeptides; 11 viral glycoproteins (designated gB, gC, gD, gE, gG, gH, gI, gJ, gK, gL, and gM) are known, and another is (gN) predicted; glycoproteins B and D.

Epstein Barr (mononucleosis, Burkitt's lymphoma, nasopharyngeal carcinoma)—Epstein-Barr nuclear antigen [EBNA] 1, 2, 3A, 3B, 3C, LP, and LMP; gp350/220 aka gp340

Cytomegalovirus—Glycoprotein B, IE1, pp89, gB and pp65 are the minimum requirements in a vaccine to induce neutralising antibodies and cytotoxic T-lymphocyte (CTL) responses. Immunisation with additional proteins, e.g., gH, gN for neutralising antibodies and 1E1exon 4 and pp150 for CTL responses, would strengthen protective immune responses.

Varicella zoster virus (chicken pox and shingles)—recombinant proteins from gE, gl and gB genes Kaposi's sarcoma-associated herpesvirus 8 (Kaposi's sarcoma)

Herpes 6 (A and B)

Herpes 7

Herpes B: glycoprotein B (gB);

Viruses—Papilloma virus: For all HPV L1 capsid protein, E1, E2, E6, and E7 genes HPV (Cervical carcinoma High-risk: 16, 18, 31, 33, 35, 39, 45, 51, 52, 56, 58, 59;

Probably high-risk: 26, 53, 66, 68, 73, 82)

HPV (common warts: 2, 7)

HPV (Plantar warts: 1, 2, 4, 63)

HPV (Flat warts: 3, 10)

HPV (Anogenital warts: 6, 11, 42, 43, 44, 55)

Viruses—Reoviridae

Rotavirus A (gastroenteritis)—VP2 and VP6 proteins

Viruses—Coronaviruses

Severe acute respiratory syndrome coronavirus (Severe Acute Respiratory Syndrome)—SARS-CoV is an enveloped plus-stranded RNA virus with a ~30 kb genome encoding replicase (Rep) and the structural proteins spike (S), envelope (E), membrane (M), and nucleocapsid (N) spike or nucleocapsid proteins, S and N genes respectively Human coronavirus 229E—spike and envelope genes Human Coronavirus NL63

Viruses—Astrovirus (gastroenteritis)—the astrovirus 87-kDa structural polyprotein Viruses—Norovirus (gastroenteritis)—Viral capsid genes, VP1 and VP2

Viruses—Flaviviridae

Dengue fever—premembrane (prM) and envelope (E) genes

Japanese encephalitis—prM, E and NS1 genes; prM, and envelope (E) coding regions of JE virus.

Kyasanur Forest disease

Murray Valley encephalitis

St. Louis encephalitis

Tick-borne encephalitis

West Nile encephalitis

Yellow fever

Hepatitis C—Hepatitis C Virus Glycoprotein E2; glycoproteins E1 and E2 of hepatitis C;

The core gene of HCV

Viruses—Picornaviridae—Enterovirus

Human enterovirus A (21 types including some coxsackie A viruses)

Human enterovirus B (57 types including enteroviruses, coxsackie B viruses)

Human enterovirus C (14 types including some coxsackie A viruses)

Human enterovirus D (three types: EV-68, EV-70, EV-94)—VP 1 gene;

Viruses—Picornaviridae—Rhinovirus

Human rhinovirus A (74 serotypes)

Human rhinovirus B (25 serotypes)

Human rhinovirus C (7 serotypes)—rhinovirus-derived VP1; the surface protein which is critically involved in infection of respiratory cells Viruses—Picornaviridae—Hepatovirus Hepatitis A Viruses—Togaviridae—Alphavirus Sindbis virus Eastern equine encephalitis virus Western equine encephalitis virus Venezuelan equine encephalitis virus Ross River virus O'nyong'nyong virus Viruses—Togaviridae—Rubivirus
Rubella virus
Viruses—Togaviridae—Hepevirus
Hepatitis E virus—the ORF2 protein; recombinant HEV capsid protein; the vaccine peptide has a 26 amino acids extension from the N terminal of another peptide, E2, of the HEV capsid protein
Viruses—Togaviridae—Bornaviridae
Borna disease virus—BDV nucleoprotein (BDV-N)
Viruses—Togaviridae—Filoviridae
Ebolavirus
Marburgvirus
Viruses—Togaviridae—Paramyxoviruses
Measles
Sendai virus
Human parainfluenza viruses 1 and 3,
Mumps virus
Human parainfluenza viruses 2 and 4
Human respiratory syncytial virus
Newcastle disease virus
Viruses—Togaviridae—Retrovirus
HIV—gag: p18, p24, p55; pol: p31, p51, p66; env: p41, p120, p160
hepatitis B virus
HTLV I, II
Viruses—Togaviridae—Rhabdoviruses
Rabies
Viruses—Togaviridae—Arenaviruses
Hanta virus
Korean hemorrhagic fever
Lymphocytic choriomeningitis virus
Junin
Machupo
Lassa
Sabia
Guanarito
California encephalitis
Congo-Crimean hemorrhagic fever
Rift valley fever
Viruses—Parvoviruses
Human parvovirus (B19)
Bacteria
*Bartonella*
*Brucella* including *B. abortus, B. canis, B. suis*
*Burkholderia (Pseudomonas) mallei, B. pseudomallei*
*Coxiella burnetii*
*Francisella tularensis*
*Mycobacterium bovis* (except BCG strain, see Appendix B-II-A, Risk Group 2 (RG2)—Bacterial Agents Including Chlamydia), *M. tuberculosis*
*Pasteurella multocida* type B—"buffalo" and other virulent strains
*Rickettsia akari, R. australis, R. canada, R. conorii, R. prowazekii, R. rickettsii, R. siberica, R. tsutsugamushi, R. typhi (R. mooseri)*
*Yersinia pestis*

A method of regulating an immune response in an individual includes administering a GDV of the present disclosure to the individual, wherein the gene transfer vector encodes at least one therapeutic gene (gene of interest, "GOI").

The present invention is described in the following Examples, which are set forth to aid in the understanding of the invention, and should not be construed to limit in any way the scope of the invention as defined in the claims which follow thereafter. The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Example 1

Figure 7:
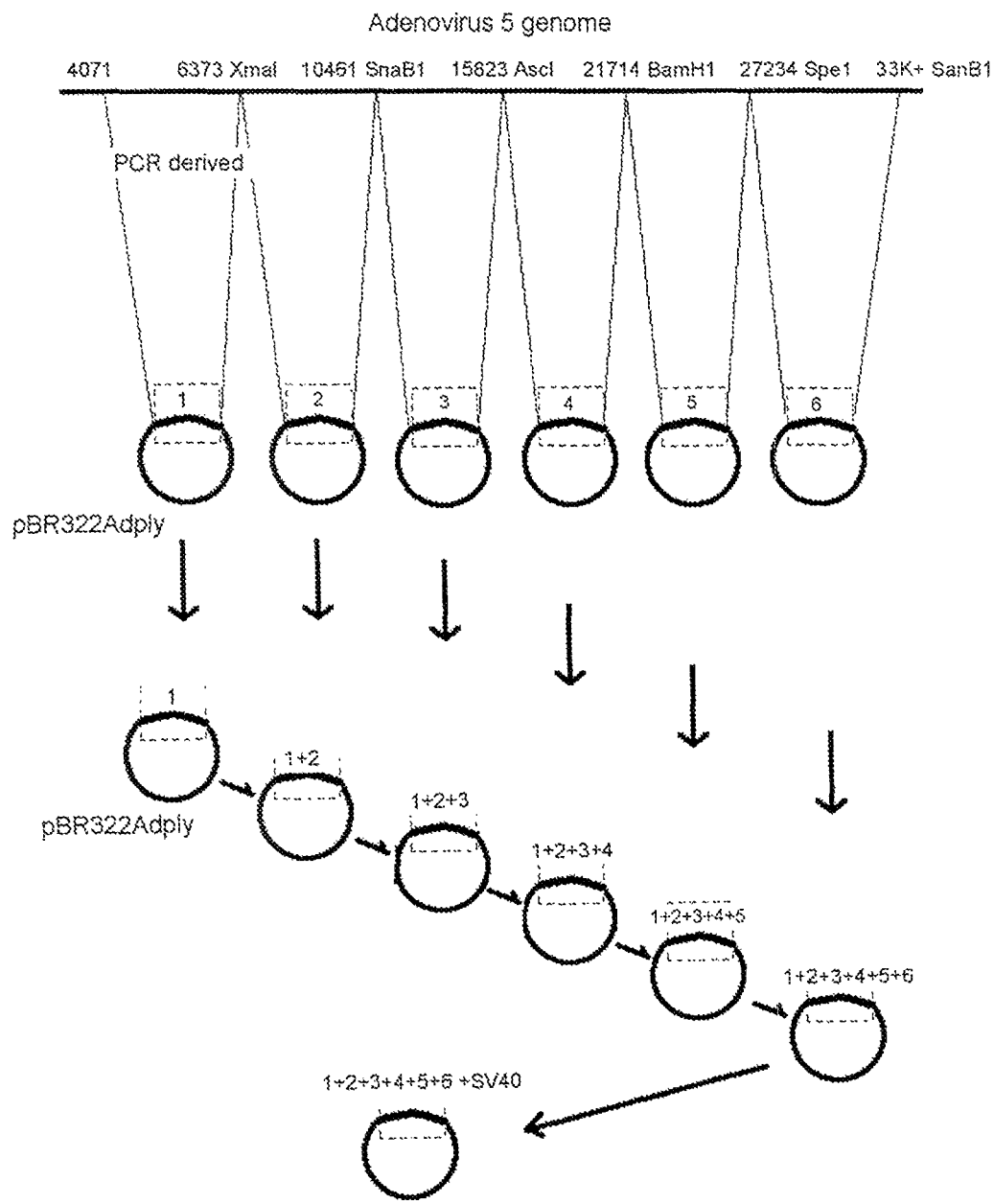
FIG. 7 is a diagrammatic representation showing an embodiment of a method for the creation of a packing construct (pPack) expressing Adenoviral late genes. In this example, the Adenoviral late genes are excised in portions of about 5 kb and cloned separately into plasmid vectors. The pieces of Ad DNA are then pieced back together sequentially into one plasmid. Finally, the SV40 (or any non-adeno) viral early gene and origin of replication are added to the plasmid comprising the re-constructed Adenovirus late region.

Construction of a Packaging Nucleic Acid Construct (pPack) (FIG. 7)

As illustrated in FIG. 7, Adenoviral late genes were introduced into a pBR322 vector by the sequential cloning of specific fragments of Ad5 DNA. A polylinker was introduced into pBR322 by ligating pBR322 cut with the restriction enzymes Hind III and Sal 1 and a polylinker composed of the complementary nucleic acids:

```
                                                (SEQ ID NO: 1)
AGCTAACTATCCCATTAATTAACCGTCCATTTTCGAAAATGCTACC

CGGGAATACGTTACGTATGAATCTGGCGCGCCTAACGTAGGATCCA

ATGCTAACTAGTATAAGATATTTAAATAAGCCCA
and
                                                (SEQ ID NO: 2)
TCGATGGGCTTATTTAAATATCTTATACTAGTTAGCATTGGATCCT

ACGTTAGGCGCGCCAGATTCATACGTAACGTATTCCCGGGTAGCAT

TTTCGAAAATGGACGGTTAATTAATGGGATAGTT.
```

The ligation was then transformed into chemically competent *E. coli* DH5alpha (InVitrogen) and ampicillin resistant colonies were selected. The polylinker contained sites for the following restriction enzyme cleavage sites (in order): Bst B1, Xma, Sna B1, Asc 1, Bam H1, Spe 1, and Swa 1. The following Ad5 DNA fragments were cloned into this vector in order: Bst B1 (4071)-Xma (6737); Xma (6737)-Sna B1 (10,461); Sna B1 (10,461)-Asc I (15,823); Asc I (15,823)-Bam H1 (21,714); Bam H1 (21,714)-Spe1 (27,234); Spe1 (27, 234)-Sna B1. The last fragment was cloned into the polylinker between the Spe 1 and Swa 1 sites.

Example 2

Construction of a Packaging Nucleic Acid Construct (pPack) (FIG. 3)

As illustrated in FIG. 3, a recombination plasmid carrying the SV40 origin of replication and early region as well as left and right arms of the Ad genome was constructed. pBR322 was cleaved with restriction enzymes Eco R1 and Bam H1 and ligated with a polylinker composed of the complementary oligonucleotides: 5' G ATC CCT ACG GTA CCT ACG TCT AGA CAG TG 3' (SEQ ID NO: 3) and 5' AAT TCA CTG TCT AGA CGT AGG TAC CGT AGG 3' (SEQ ID NO: 4). The ligation was transformed into chemically competent DH5alpha *E. coli* (InVitrogen) and colonies resistant to ampicillin were selected. In addition to restoring the Eco R1 and Bam H1 sites, this polylinker introduced unique sites for the restriction enzymes Kpn I and Xba I, such that the order of sites was: Bam H1, Kpn 1, Xba 1, and Eco R1. Three fragments were then cloned into this vector at sites in the polylinker.

The SV40 origin of replication and Early region was cloned as a Bam H1/Kpn fragment (nt 2533 to nt 5243/0, continuing to nt 298) at the Kpn and Bam H1 sites in the polylinker. A fragment of the left arm of Ad5 genome from nt 4501 to nt 5466, was amplified by PCR from Ad5 DNA using the primers: 5' GGT ACC TGT ATC CGG TGC ACT TGG GAA ATT TG 3' (SEQ ID NO: 5) and 5' TCT AGA ACA CCA TGG TCA AAT GCT ACC TGG G 3' (SEQ ID NO: 6). The resulting DNA fragment was cleaved with restriction enzymes Kpn 1 and Xba 1 and ligated between the Kpn and Xba 1 sites in the polylinker. A fragment of the right arm, from nt 34,677 to nt 35836, just before the right ITR sequence was amplified by PCR, cleaved with the restriction enzymes Eco R1 and Xba 1 and ligated into the polylinker at the Xba 1 and Eco R1 sites.

This plasmid was recombined with the Ad 5 genomic DNA in E. coli. The plasmid was digested with the restriction enzyme Xba to produce a linear molecule with the regions of Ad5 left and right arms at the two ends of the linearized plasmid. The linear plasmid and wild-type Ad5 genomic DNA were co-electroprated into rec A+ E. coli and ampicillin resistant colonies selected. Recombination between the sequences at the ends of the linearized plasmids and the Ad5 genomic DNA resulted in a circular plasmid containing an ampicillin resistance gene, a bacterial origin of replication, the SV40 origin of replication and Early region, and the Ad late genes but without the IX and E1 genes, the Ad packaging site, or either of the Ad ITRs.

Example 3

Construction of a Fully-Deleted Adenoviral Vector (FDV) Carrying the H1N1 Influenza Hemagglutinin Gene (FIG. 1)

The "stuffer" basis for this FDV was a bacterial artificial chromosome (BAC) vector carrying the human ATIC gene encoding 5-aminoimidazole-4-carboxamide ribonucleotide formyltransferase/IMP cyclohydrolase. A targeting plasmid construct for transforming this human BAC ATIC clone into a FDV was composed of: the left Ad ITR and Ψ; the right Ad ITR; the gene of interest, in this case the H1N1 influenza neuraminidase in an expression cassette with a cytomegalovirus promoter at the five prime end and a polyadenylation sequence at the three prime end; two regions from the human ATIC gene to mediate homologous recombination with the human ATIC BAC; and a plasmid vector with a bacterial origin of replication and an antibiotic resistance gene.

The arrangement of these elements is schematically shown in FIG. 1. The Ad left ITR and Ψ sequence are amplified by PCR from Ad 5 genomic DNA with two primers:

```
                                        (SEQ ID NO: 7)
AATACCCGGGAATATGAGCTCATCATGTTTAAACAATCATCATCAA

TAATATACCTATTTTG
and (SEQ ID NO: 8)
ACATATCTAGAAACAGTCTCCACGTAAACGGTCAAAG.
```

The right ITR was amplified by PCR from Ad 5 genomic DNA using two primers:
TAACATGCATAATATGCCCGGGCATAGCGGCAGC-CTAACAGTCAGCCTTACC (SEQ ID NO: 9) and
AATGGGCCCATATAGTTTAAACATACATCAT-CAATAATATACCTATTTTG (SEQ ID NO: 10). The vector was pBR322.

The two regions of human ATIC DNA, from exons 3 and 16, were amplified by PCR using two pairs of primers:

```
exon 3
                                        ((SEQ ID NO: 11)
ATAAGCTTGAACATACACAACAGTTAGG
and (SEQ ID NO: 12)
ATAAGCTTTCTGGCAGCAACTTCATAAC)
and exon 16
                                        ((SEQ ID NO: 13)
TTATCGATGATGAAGATTTGATAAAGTGG
and (SEQ ID NO: 14)
TTGGCGCGCCGTTATCCTCAAAGTTTCAGGC).
```

The neuraminidase gene was amplified by PCR from cDNA isolated from cells infected by the influenza (A/California/07/2009(H1N1)). The PCR primers were:

```
                                        (SEQ ID NO: 15)
CTGTCGACAAATGAATCCAAACCAAAAGAT
and (SEQ ID NO: 16)
TCGAAGCTTAGTTACTTGTCAATGGTAAATG.
```

The targeting vector composed of these sequences was linearized by cleavage with a restriction endonuclease that cuts the plasmid uniquely between the ATIC regions. This linearized plasmid and the human ATIC BAC were co-electroporated into recombination proficient E. coli, and ampicillin resistant colonies were selected. The plasmid resulting from homologous recombination between these two molecules was the FDV. For subsequent use, this FDV carrying the H1N1 neuraminidase gene was liberated by cleaving with a restriction endonuclease that cleaves at the outer edges of the left and right ITRs.

Example 4

Figure 8:
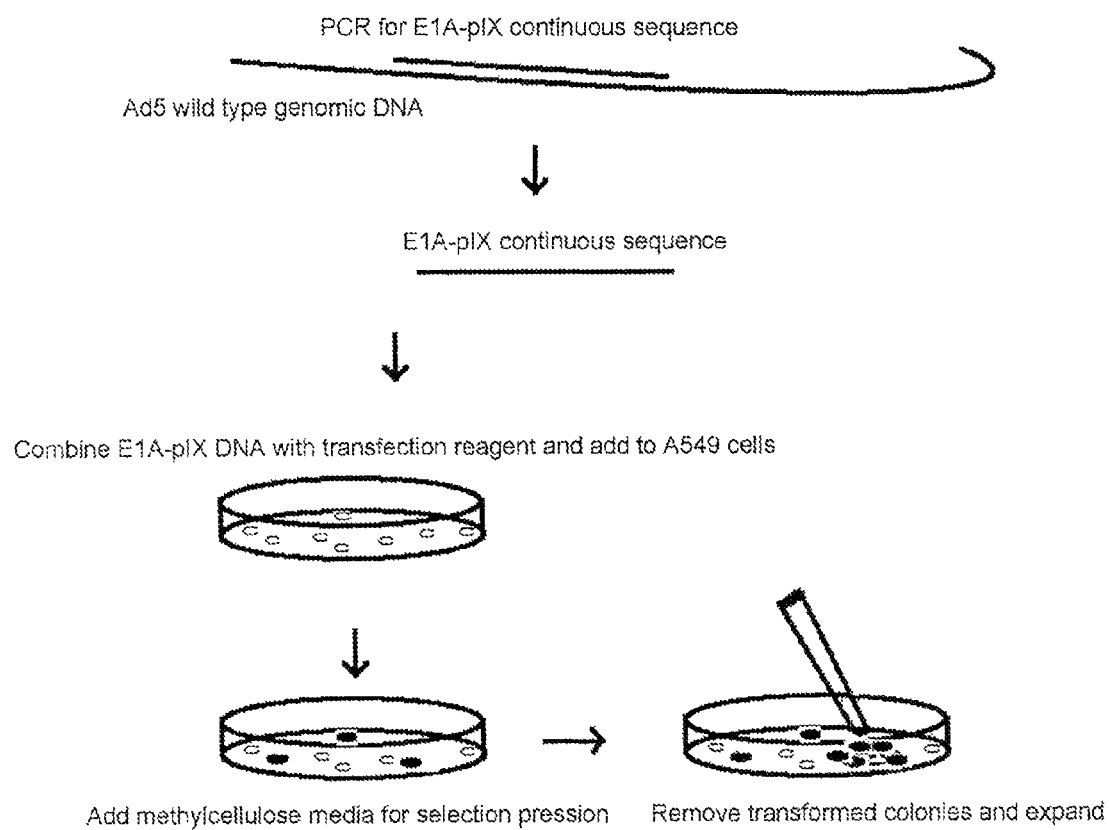
FIG. 8 is a diagrammatic representation showing an embodiment of a method of producing an Adenovirus packaging cell (PC) line (mammalian cell line) expressing the E1 and IX genes from Adenovirus, permissive for production of encapsidated fully-deleted Adenovirus-based gene transfer vectors (GDVs) without helper Adenovirus. First, the E1 and IX genes are amplified by PCR from the wild-type Adenovirus DNA. Next, the E1/IX DNA is transfected into a human cell line (A549). Finally, transformed colonies of cells are isolated and expanded for testing.

Construction of an Adenoviral Packaging Cell (PC) Line Carrying the Ad5 E1 and IX Genes by Cell Transformation (FIG. 8)

As illustrated in FIG. 8, a DNA fragment containing the Ad5 E1 and IX genes was produced by polymerase chain reaction (PCR) using Ad5 genomic DNA as a template and primers: AAT ACT CGA GAT AAT GAA TTC ATA TCG CCC AGG TGT TTT TCT CAG G (SEQ ID NO: 17) and AAT AGG ATC CAT AAT GAA TTC ATA GAT CCA AAT CCA AAC AGA GTC (SEQ ID NO: 18). This amplified the Ad5 region from nt 385 to nt 4070. PCR cycling conditions were thirty cycles: 95° C., 1 min; 60° C., 2 min; and 68° C., 4 min.

A549 cells were grown to 90% confluency in a T-75 tissue culture flask with serum free RPMI (RPMI SF), Sigma R6504. On the day before transfection, the media was removed from the flask via aspiration, and the cells were detached by adding 5 ml 0.25% trypsin/EDTA (Sigma T3449) to the flask. After 5 minutes of incubation at 37° C., the solution with the cells was centrifuged for 5 min at 200×g with 10 ml RPMI in a 50 ml conical tube in a swinging rotor centrifuge (Centra CLR3). After decanting the supernatant, the cells were resuspended in 5 ml RPMI SF and pipetted up and down seven times gently to attain a single cell suspension. After quantitating the viable cells by trypan blue staining and counting in a hemacytometer, 1×106 cells were plated in each well of a 6 well tissue culture plate with 5 ml RPMI SF and swirled gently to evenly distribute the cells. The cells were incubated overnight in tissue culture incubator.

On the day of transfection, the media was removed by aspiration and immediately replaced with fresh RPMI SF (2 ml). To prepare the DNA for transfection, 12 μg of the E1/DC DNA was added to 400 μl 150 mM sterile NaCl, and then 24 μl jetPEI™ (PolyPlus 101-10) was added to 400 μl 150 mM sterile NaCl. DNA/NaCl mixture was slowly added to the jetPEI™/NaCl mixture. The solution was incubated for 20 minutes at room temperature. 200 μl of the DNA/jetPEI™ solution was added to each well. The cells were then incubated overnight in a tissue culture incubator.

The day after transfection, the medium was removed from each well via aspiration and 5 ml RPMI SF with 1.5% carboxymethyl-celluose (Sigma C5013) was added. The cultures were maintained in the tissue culture incubator and the medium was changed twice per week. The well was examined daily for proliferation beyond a monolayer of cells, that is, for cell colonies that had lost contact inhibition and were forming discernable masses above the monolayer. These colonies appear from 10 to 90 days after transfection.

When colonies are of sufficient size (>100 cells), they were removed with a sterile pipet tip and seeded on a single well in a 6 well plate (5 ml RPMI SF, without methylcellulose). The single colony cultures were grown until 90% confluence. They were then passaged by standard techniques using the same medium.

DNA was isolated from these single colony cultures using standard DNA isolation kits such as DNeasy (Qiagen 69504), and was then tested for the presence of the E1/IX DNA fragment by PCR using the conditions described above. The expression of the E1 and IX genes was then tested by RT-PCR using primer pairs for E1 (AT GAG ACA TAT TAT CTG CCA CGG (SEQ ID NO: 19) (nt 560-nt 582) and TTA TGG CCT GGG GCG TTT ACA G (SEQ ID NO: 20) (nt 1524-nt 1545) and for the IX gene (AT GAG CAC CAA CTC GTT TGA TG (SEQ ID NO: 21) (nt 3609-nt 3630) and TT AAA CCG CAT TGG GAG GGG (SEQ ID NO: 22) (nt 4012-nt 4030).

Example 5

Figure 9:
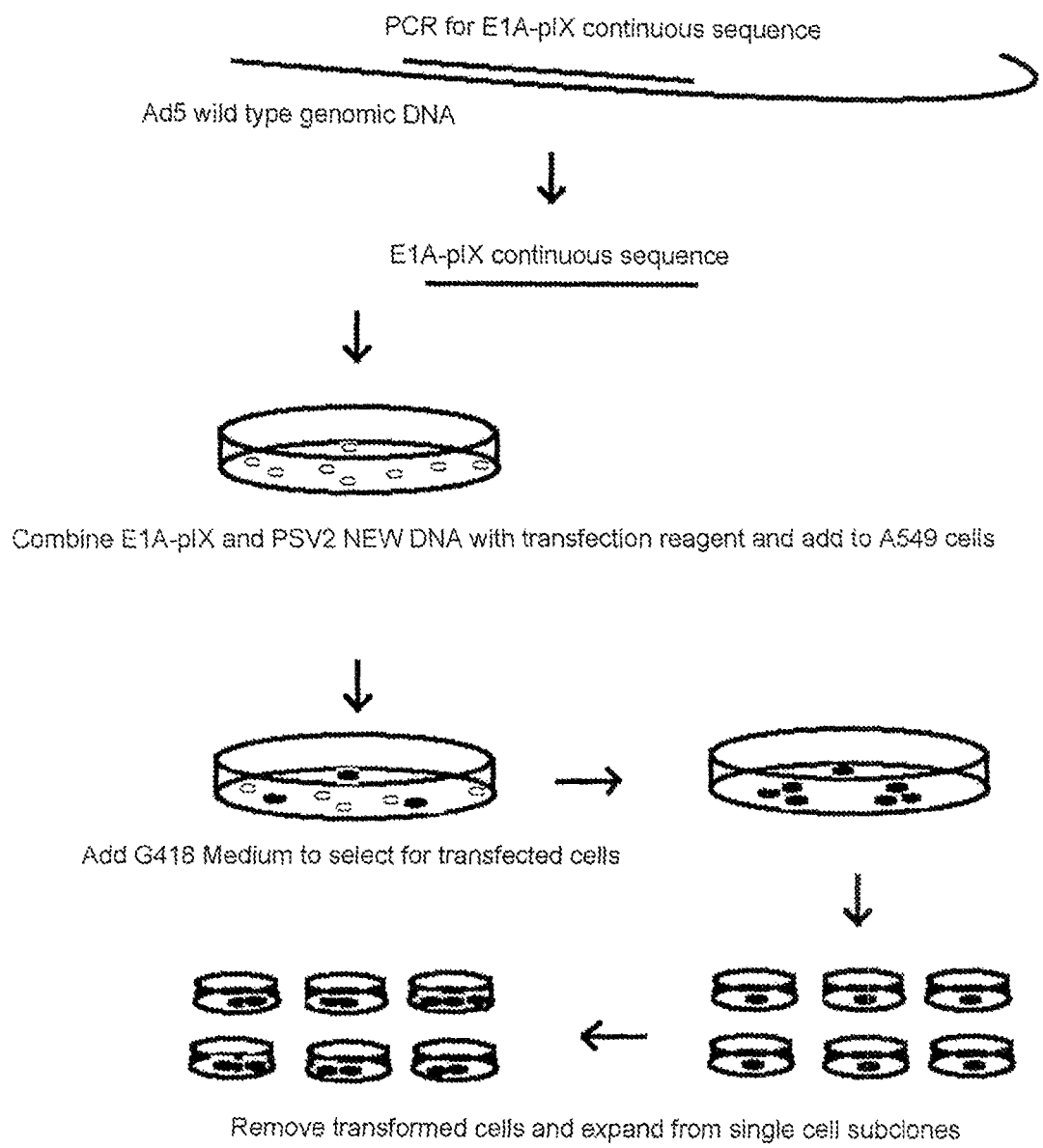
FIG. 9 is a diagrammatic representation showing an embodiment of a method of producing an Adenovirus packaging cell (PC) line (mammalian cell line) expressing the E1 and IX genes from Adenovirus using co-transfection with a neomycin selection cassette, permissive for production of encapsidated fully-deleted Adenovirus-based gene transfer vectors (GDVs) without helper Adenovirus. First, the E1 and IX genes are amplified by PCR from the wild-type Adenovirus DNA. Next, the E1/IX DNA and a neomycin selection cassette are co-transfected into a human cell line (A549). Finally, colonies resistant to G418 are isolated and tested for expression of the E1/IX genes.

Construction of an Adenoviral Packaging Cell (PC) Line Carrying the Ad5 E1 and IX Genes by Co Transfection with pSV2-Neo (FIG. 9)

As schematically illustrated in FIG. 9, A549 cells were grown to 90% confluence in a T-75 tissue culture flask with serum free RPMI (RPMI SF), Sigma R6504. On the day before transfection, the media was removed from the flask via aspiration, and the cells were detached by adding 5 ml 0.25% trypsin/EDTA (Sigma T3449) to the flask. After 5 minutes of incubation at 37° C., the solution with the cells, was centrifuged for 5 min at 200×g with 10 ml RPMI in a 50 ml conical tube in a swinging rotor centrifuge (Centra CLR3). After decanting the supernatant, the cells we re resuspended in 5 ml RPMI SF and pipetted up and down seven times gently to attain a single cell suspension. After quantitating the viable cells by trypan blue staining and counting in a hemacytometer, 1×106 cells were plated in each well of a 6 well tissue culture plate with 5 ml RPMI SF and swirled gently to evenly distribute the cells. The cells were incubated overnight in tissue culture incubator.

On the day of transfection, the media was removed by aspiration and immediately replaced with fresh RPMI SF (2 ml). To prepare the DNA for transfection, 6 μg of the E1/DC DNA was added and 6 μg of PSV2Neo DNA to 400 μl 150 mM sterile NaCl, and then 24 μl jetPEI™ (PolyPlus 101-10) was added to 400 μl 150 mM sterile NaCl. The DNA/NaCl mixture was slowly added to the jetPEI™/NaCl mixture. The solution was incubated for 20 minutes at room temperature. 200 μl of the DNA/jetPEI™ solution was added to each well. The cells were then incubated overnight in a tissue culture incubator.

Forty-eight hours after transfection, the medium was removed from the well via aspiration and 5 ml RPMI with 1.0 mg per ml G418 (geneticin) was added. The cultures were maintained in the tissue culture incubator and medium with G418 was changed daily. The well was examined daily for death of non-transfected cells and proliferation of transfected cells. Non-adherent dead cells were removed via medium changes.

When sufficient numbers of cells were present in a geneticin resistant colony (>1000 cells), they were subcloned as single colonies. The single colony cultures were grown until 90% confluence. They were then passaged by standard techniques using the same medium.

DNA was isolated from these single colony cultures using standard DNA isolation kits such as DNeasy (Qiagen 69504), and was then tested for the presence of the E1/IX DNA fragment by PCR using the conditions described above. The expression of the E1 and IX genes was then tested by RT-PCR using primer pairs for E1 (AT GAG ACA TAT TAT CTG CCA CGG (SEQ ID NO: 19) (nt 560-nt 582) and TTA TGG CCT GGG GCG TTT ACA G (SEQ ID NO: 20) (nt 1524-nt 1545) and for the IX gene (AT GAG CAC CAA CTC GTT TGA TG (SEQ ID NO: 21) (nt 3609-nt 3630) and TT AAA CCG CAT TGG GAG GGG (SEQ ID NO: 22) (nt 4012-nt 4030).

Example 6

Packaging of a FDV Carrying the Human Factor VIII Coding Sequence by Co-Transfection with a Packaging Construct (pPack) to Propagate GDVs (FIG. 10)

QBI293A cells were grown to 90% confluence in a T-75 tissue culture flask with serum free RPMI 10% FCS (RPMI), Sigma R6504. On the day before transfection, media was removed from the flask via aspiration, and cells were detached by adding 5 ml 0.25% trypsin/EDTA (Sigma T3449) to the flask. After 5 minutes of incubation at 37° C., the solution with the cells was centrifuged for 5 min at 200×g with 10 ml RPMI in a 50 ml conical tube using a swinging rotor centrifuge (Centra CLR3). After decanting the supernatant, cells were resuspended in 5 ml RPMI SF and pipetted up and down seven times gently to attain a single cell suspension. After quantitating the viable cells by trypan blue staining and counting in a hemacytometer, 1×10$^6$ cells were plated in each well of a 6 well tissue culture plate with 5 ml RPMI and swirled gently to evenly distribute the cells. The cells were incubated overnight in a tissue culture incubator.

On the day of transfection, the media was removed by aspiration and immediately replaced with fresh RPMI (2 ml). To prepare the DNA for co-transfection, 4 µg of DNA of a fully-deleted Ad vector carrying Factor VIII and 4 µg of DNA from a plasmid carrying the Ad 5 sequences (nt 3534-28,129, and nt 30,821-35931) were added to 400 µl 150 mM sterile NaCl, and then 24 µl jetPEI™ was added (PolyPlus 101-10) to 400 µl 150 mM sterile NaCl. The DNA/NaCl mixture was added slowly to the jetPEI™/NaCl mixture. The solution was incubated for 20 minutes at room temperature. Next, 200 µl of the DNA/jetPEI™ solution was added to each well. The cells were incubated for four hours in a tissue culture incubator. After incubation, the medium was replaced with 5 ml RPMI and the cells were returned to a tissue culture incubator.

Forty-eight hours after transfection the cells were scraped from the surface of each well using a cell scraper (Falcon 353086). The solution was transferred to a 50 ml conical tube, combining like wells. The cell suspension was centrifuged for five minutes at 200×g and supernatant was decanted without disturbing the cell pellet. The pellet was resuspended in 100 µl RPMI. The pellet was frozen in a dry ice/isopropanol bath for three minutes and was then thawed in a 37° C. water bath for three minutes. The freeze thaw cycle was repeated a total of three times. The resultant cell lysate was centrifuged for eight minutes at 1200×g. The supernatant was removed with a micropipet and diluted 10 times with RPMI. The supernatant, GDV Factor VIII preparation, was stored at −80° until infection.

Figure 10A:
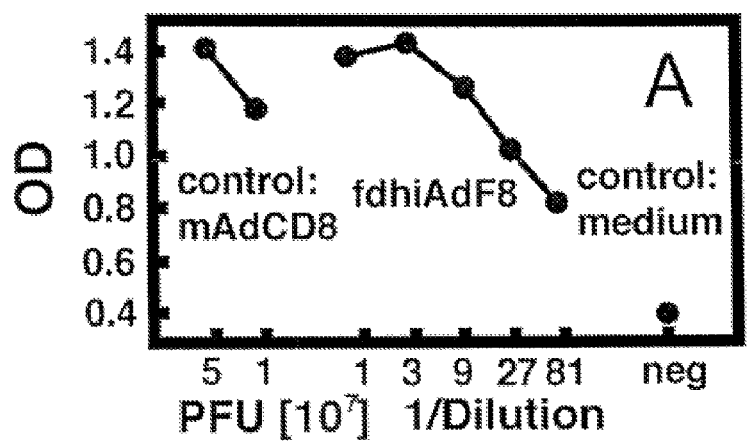
FIG. 10A-C shows the expression of Factor VIII using a GDV of the present invention with a DNA insert of a F8 gene. The GDV was produced by co-transfection with a packaging plasmid into QBI cells (QBiogene). The amount of GDV produced in packaging cells was measured by an Adenovirus-specific capture ELISA. mAdCD8 was used as a positive control (FIG. 10A). Fibroblasts were infected with the GDV. Factor VIII DNA was detected in transduced cells (virus), in mock-infected cells (neg), or in the GDV DNA (pos) by F8-specific PCR (FIG. 10B). The release of F8 was detected by a F8-specific EliSpot assay in the F8 producing cells (20B8, middle panel), in mock-infected cells (neg, left panel), and in GDV-transduced fibroblasts (virus, right panel) (FIG. 10C).
Figure 10B:
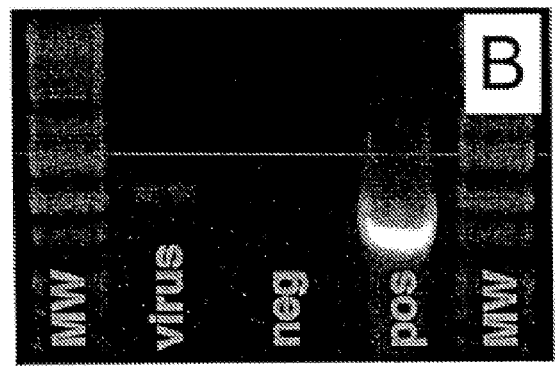

The GDV Factor VIII preparation was analyzed by quantitating virions by a sandwich ELISA using a monoclonal anti-body against Ad5 virions (FIG. 10A). This clearly showed the presence of Ad virions at only slightly lower concentration than the positive control, a first generation Ad vector carrying the mouse CD8. To demonstrate the infectivity of the GDV Factor VIII preparation, A549 human fibroblasts were infected with the GDV Factor VIII preparation. 48 hours after infection, the cells were harvested for DNA and the isolated DNA was analyzed by PCR for F8 using primers specific for the F8 transgene (Forward primer from the CMV promoter: Cgcgttacataacttacggta (SEQ ID NO: 23); Reverse primer from the Factor VIII coding sequence: ccagggaagactttatcatc (SEQ ID NO: 23)) (FIG. 10B). DNA from cells infected with GDV Factor VIII gave a positive PCR signal, while uninfected cells did not. This showed the transduction of the GDV Factor VIII DNA into cells infected with the GDV Factor VIII.

To demonstrate the secretion of F8 from cells infected with GDV Factor VIII, an EliSpot assay for F8 secreting cells was used. An Elispot plate (Millipore MSIPS4W10) was wetted with 15 µl/well 35% sterile ethanol. This was followed with three 150 µl sterile PBS washes. F8 capture antibody (Abcam 53203) was added at a 1 to 5000 dilution, 100 µl/well in PBS. The plate was incubated overnight at 4° C. The plate was washed two times with 150 µl PBS/well, and was then blocked overnight with 3% BSA in PBS 150 µl/well.

A549 cells grown to 90% confluence in a T-75 flask were trypsinized and resuspended, and the cells were counted using a hemacytometer. The cells were seeded on an Elispot plate at 50 thousand cells/well in a volume of 50 µl RPMI/well. The cells were incubated overnight in a tissue culture incubator. On the following day, 50 µl of GDV Factor VIII supernatant (above) was added to each well of cells. The cells were held overnight in tissue culture incubator.

Figure 10C:
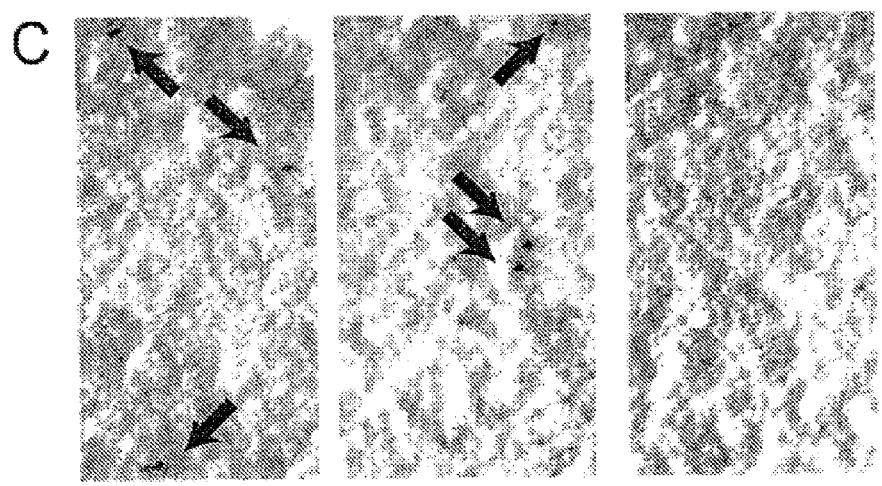

Plate development began with five washes of 150 µl/well of PBS/0.01% Tween-20 and two washes 150 µl PBS to remove cells. F8-HRP conjugated antibody (American Diagnostica ESH-8R) at 1 to 4000 dilution in PBS 0.5% BSA was added to each well, and the plate was incubated for 1.5 hours at 37° C. The plate was then washed seven times with 200 µl PBS/well. The substrate was prepared by dissolving 4.0 mg 3-Amino 9ethyl carbazole (Sigma 038K1032) in 1 ml dimethyl formamide (Sigma D-4451), which was then added to 14 ml citrate-phosphate buffer, 0.1M pH 6.0, and 15 µl 30% $H_2O_2$. 100 µl of the substrate solution was added to each well, incubated for ten minutes at room temperature and then washed liberally with tap water. Cells infected with GDV Factor VIII gave positive signal in the EliSpot assay indicating their secretion of F8 (FIG. 10C).

Example 7

Keratinocyte and Fibroblast Isolation, Characterization, Engineering and Transplantation As a prelude to establishing a skin transplantation model, keratinocytes and fibroblasts were isolated from neonatal and adult mice using the following protocol:

Day old neonatal mouse pups were sacrificed by decapitation then all limbs were removed. The body was immersed in providone/iodine for 2 minutes then rinsed in 70% ethanol for 2 more minutes, followed by 2 more minutes in PBS/PSN. The skin was surgically removed by first making a ventral incision anterior to posterior then, the skin was gently peeled off in one piece. Skins were rinsed briefly in PBS/PSN then placed in 5 mls Dispase, (BD) at 4° C. for 16 hours. After Dispase treatment the skins were rinsed in PBS/PSN and transferred to a 10 cm Petri dish with 10 mls PBS/PSN. The epidermis was gently peeled off the dermis in one continuous sheet. The epidermal sheets were floated on 1 ml drops of trypsin at room temp for 15 to 20 minutes. The epidermal sheets were then gently agitated with forceps to release keratinocyte clumps. 10 mls of PBS/PSN 10% FCS was added and the skins were pipetted up and down with a 25 ml pipette to further release keratinocytes. The volume was brought to 50 mls with PBS/PSN 10% FCS and filtered through a 100 µm cell strainer. The cells were pelleted at 300×g for 4 minutes, washed with PBS/PSN 10% FCS, resuspended in growth medium, and counted.

After step six above, the dermis was collected and briefly rinsed in PBS/PSN. The dermis was incubated for 15 to 20 minutes in 10 mls of 1 mg/ml collagenase type V, (Sigma) in PBS, with gentle inversion at 37° C. The collagenase was neutralized with the addition of 20 mls PBS/PSN 10% FCS. The cell clumps were dissociated with gentle pipetting using a 25 ml pipette. The volume was brought to 50 mls with PBS/PSN 10% FCS and the cells were filtered through a 100 µm cell strainer. The cells were pelleted at 300×g for 5 minutes, washed with PBS/PSN 10% FCS, resuspended in growth media and counted.

Keratinocytes and fibroblasts harvested from both neonates and adults were then analyzed by FACS analysis both for the expression of MHC class I and class II expression, and for tissue specific markers. Representative data from adult keratinocytes are presented in Table 5.

TABLE 5

FACS analysis of keratinocytes harvested from
adult mice. Numbers are % positive cells.

Surface Antigen

|  | MHC I | MHC II | CD98 | Integrin 6 | epCAM |
|---|---|---|---|---|---|
| Positive [%] | 84.5 | 5.6 | 95.4 | 88.4 | 0.7 |

In contrast, neither neonatal fibroblasts nor keratinocytes expressed high levels of MHC or differentiation markers (Table 6). Prolonged incubation of neonatal keratinocytes and fibroblasts lead to increased expression of both MHC and tissue specific antigens.

TABLE 6

FACS analysis of keratinocytes and fibroblasts from neonatal mice.

Surface Antigen - [%] Positive

|  | MHC I | MHC II | CD98 | Integrin 6 | epCAM |
|---|---|---|---|---|---|
| Keratinocytes | 0.6 | 0.5 | 67 | 31.7 | 0.1 |
| Fibroblastsz | 0.7 | 1.7 | 91.1 | 2.3 | 0 |

As reported in the literature, keratinocytes showed different growth requirements. While keratinocytes required specialty media (e.g. Cnt o2 from Millipore), fibroblasts grew well on standard Eagle's medium. This is an important consideration when producing engineered skin containing both keratinocytes and fibroblasts.

We used three different matrices to produce engineered skin: decellularized mouse dermis, Neomem membrane (Citagenix), and Transwell-col (Corning International Life Sciences). In all cases, fibroblasts were "pre-seeded" on the membrane, before the keratinocytes were, and the membranes were incubated in medium especially designed to foster growth of keratinocytes on matrices (Con02-3D, Millipore). Both keratinocytes and fibroblasts will be infected with a GDV of the present disclosure that is based on Human Serotype 5, carrying CD8, and preferably the human CD8α-chain. In an embodiment, the viral capsid can be altered (pseudotyped) in the hypervariable region of the viral hexon. Infection efficiency will be determined by FACS analysis for cell surface expression of CD8.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

---

What is claimed is:

1. An Adenovirus packaging cell line permissive for replication of a fully-deleted Adenoviral vector independent of helper Adenovirus, the cell line comprising an Adenovirus early region 1 (E1) coding sequence and an Adenovirus pIX coding sequence, both of which are stably integrated into the cell line; and further comprising a replication defective circular packaging construct having at least a subset of Adenoviral late genes selected from the group consisting of L1, L2, L3, L4, L5, E2A, and E4, while being absent of at least one inverted terminal repeat and a packaging signal;
wherein upon transfection of a fully-deleted Adenoviral vector construct into the cell line, a fully-deleted adenoviral-based gene transfer vector can be encapsidated independent of helper Adenovirus,
wherein the encapsidated fully-deleted adenoviral-based gene transfer vector includes both adenoviral inverted terminal repeats, the packaging signal, and at least one DNA insert encoding a protein of interest, and
wherein the encapsidated fully-deleted adenoviral-based gene transfer vector is absent of adenoviral structural genes.

2. The Adenovirus packaging cell line of claim 1 wherein the cell line is selected from one of A549 cells or primary cells.

3. The Adenovirus packaging cell line of claim 1 wherein the E1 coding sequence and the pIX coding sequence is of Adenovirus type 5.

4. The Adenovirus packaging cell line of claim 1 wherein the E1 coding sequence and the pIX coding sequence are driven by an E1 promoter and terminated by a heterologous polyadenylation site.

5. The Adenovirus packaging cell line of claim 1 wherein the E1 coding sequence and the pIX coding sequence are stably integrated at different sites in the cell line.

6. A system comprising:
(a) an Adenovirus packaging cell line;
(b) a fully-deleted Adenoviral vector construct; and
(c) a replication defective circular packaging construct, having at least a subset of Adenoviral late genes selected from the group consisting of L1, L2, L3, L4, L5, E2A, and E4, while being absent of at least one inverted terminal repeat and a packaging signal;
wherein the fully-deleted Adenoviral vector construct and the packaging construct can transfect the Adenovirus packaging cell line resulting in the encapsidation of a fully-deleted Adenoviral gene transfer vector independent of helper Adenovirus;
wherein the encapsidated fully-deleted Adenoviral gene transfer vector includes both adenoviral inverted terminal repeats, the packaging signal, and at least one DNA insert encoding a protein of interest, and
wherein the encapsidated fully-deleted Adenoviral gene transfer vector is absent of adenoviral structural genes.

7. The system of claim 6 wherein the packaging construct itself is incapable of being packaged.

8. The system of claim 6 wherein the Adenovirus packaging cell line is selected from one of A549 cells or primary cells.

9. The system of claim 6 wherein the encapsidated fully-deleted Adenoviral vector is replication deficient.

10. The system of claim 6 wherein:
the Adenovirus packaging cell line comprises an Adenovirus early region 1 (E1) coding sequence stably integrated into the cell line,
the fully-deleted Adenoviral vector construct comprises LITR, Ψ, and RITR from Adenovirus, a gene expression construct, and human genomic stuffer DNA, and
the packaging construct comprises an Adenovirus late region coding sequence, or a subset thereof, and an Adenovirus pIX coding sequence.

11. The system of claim 6 wherein:
the Adenovirus packaging cell line comprises an Adenovirus early region 1 (E1) coding sequence and an Adenovirus pIX coding sequence stably integrated into the cell line, and
the fully-deleted Adenoviral vector construct comprises LITR, Ψ, and RITR from Adenovirus, a gene expression construct, and human genomic stuffer DNA.

12. The system of claim 6 wherein:
the Adenovirus packaging cell line comprises an Adenovirus early region 1 (E1) coding sequence and a non-Adenoviral viral early region coding sequence stably integrated into the cell line,
the fully-deleted Adenoviral vector construct comprises LITR, Ψ, and RITR from Adenovirus, a gene expression construct, and human genomic stuffer DNA, and
the packaging construct comprises an Adenovirus late region coding sequence or a subset thereof, an Adenovirus pIX coding sequence, and a non-Adenoviral origin of replication (ori).

13. The system of claim 6 wherein:
the Adenovirus packaging cell line comprises an Adenovirus early region 1 (E1) coding sequence, an Adenovirus pIX coding sequence, and a non-Adenoviral viral early region coding sequence stably integrated into the cell line,
the fully-deleted Adenoviral vector construct comprises LITR, Ψ, and RITR from Adenovirus, a gene expression construct, and human genomic stuffer DNA, and
the packaging construct comprises an Adenovirus late region coding sequence or a subset thereof and a non-Adenoviral origin of replication (ori).

14. The system of claim 6 wherein:
the Adenovirus packaging cell line comprises a first nucleic acid having an Adenovirus early region 1 (E1) coding sequence; and a second nucleic acid having an Adenovirus late region coding sequence under control of an inducible promoter, and an Adenovirus pIX coding sequence, wherein each nucleic acid is stably integrated into the cell line,
the fully-deleted Adenoviral vector construct comprises LITR, Ψ, and RITR from Adenovirus, a gene expression construct, a transcriptional activator, and human genomic stuffer DNA, and
no packaging construct is present.

15. The system of claim 6 wherein:
the Adenovirus packaging cell line comprises a first nucleic acid having an Adenovirus early region 1 (E1) coding sequence and an Adenovirus pIX coding sequence under control of an inducible promoter; and a second nucleic acid having an Adenovirus late region coding sequence, wherein each nucleic acid is stably integrated into the cell line,
the fully-deleted Adenoviral vector construct comprises LITR, Ψ, and RITR from Adenovirus, a gene expression construct, a transcriptional activator, and human genomic stuffer DNA, and
no packaging construct is present.

16. The system of claim 6 wherein:
the Adenovirus packaging cell line comprises a first nucleic acid having an Adenovirus early region 1 (E1) coding sequence; and a second nucleic acid having a subset of an Adenovirus late region coding sequence under control of an inducible promoter and an Adenovirus pIX coding sequence, wherein each nucleic acid is stably integrated into the cell line,
the fully-deleted Adenoviral vector construct comprises LITR, Ψ, and RITR from Adenovirus, a gene expression construct, a subset of Adenovirus late region coding sequence, a transcriptional activator, and human genomic stuffer DNA, and
no packaging construct is present.

17. The system of claim 6 wherein:
the Adenovirus packaging cell line comprises a first nucleic acid having an Adenovirus early region 1 (E1) coding sequence and an Adenovirus pIX coding sequence; and a second nucleic acid having an Adenovirus late region coding sequence under control of an inducible promoter, wherein each nucleic acid is stably integrated into the cell line,
the fully-deleted Adenoviral vector construct comprises LITR, Ψ, and RITR from Adenovirus, a gene expression construct, a subset of Adenovirus late region coding sequence, a transcriptional activator, and human genomic stuffer DNA, and
no packaging construct is present.

18. The system of claim 6 wherein:
the Adenovirus packaging cell line comprises a first nucleic acid having an Adenovirus early region 1 (E1) coding sequence; and a second nucleic acid having an Adenovirus late region coding sequence and an Adenovirus pIX coding sequence under control of an inducible promoter, non-Adenoviral viral early region coding sequence under control of an inducible promoter, and a non-Adenoviral origin of replication (ori), wherein each nucleic acid is stably integrated into the cell line,
the fully-deleted Adenoviral vector construct comprises LITR, Ψ, and RITR from Adenovirus, a gene expression construct, one or more transcriptional activators, and human genomic stuffer DNA, and
no packaging construct is present.

19. The system of claim 6 wherein:
the Adenovirus packaging cell line comprises a first nucleic acid having an Adenovirus early region 1 (E1) coding sequence and an Adenovirus pIX coding sequence; and a second nucleic acid having an Adenovirus late region coding sequence under control of an inducible promoter, a non-Adenoviral viral early region coding sequence under control of an inducible promoter, and a non-Adenoviral origin of replication (ori), wherein each nucleic acid is stably integrated into the cell line,
the fully-deleted Adenoviral vector construct comprises LITR, Ψ, and RITR from Adenovirus, a gene expression construct, one or more transcriptional activators, and human genomic stuffer DNA, and
no packaging construct is present.

20. The system of claim 6 wherein:
the Adenovirus packaging cell line comprises a first nucleic acid having an Adenovirus early region 1 (E1) coding sequence; and a second nucleic acid having a subset of an Adenovirus late region coding sequence under control of an inducible promoter, an Adenovirus pIX coding sequence, a non-Adenoviral viral early region coding sequence under control of an inducible promoter, and a non-Adenoviral origin of replication (ori), wherein each nucleic acid is stably integrated into the cell line,
the fully-deleted Adenoviral vector construct comprises LITR, Ψ, and RITR from Adenovirus, a gene expression construct, a subset of an Adenovirus late region coding sequence under control of one or more transcriptional activators, and human genomic stuffer DNA, and
no packaging construct is present.

21. The system of claim 6 wherein:
the Adenovirus packaging cell line comprises a first nucleic acid having an Adenovirus early region 1 (E1) coding sequence and an Adenovirus pIX coding sequence; and a second nucleic acid having an Adenovirus late region coding sequence under control of an inducible promoter, a non-Adenoviral viral early region coding sequence under control of an inducible promoter, and a non-Adenoviral origin of replication (ori), wherein each nucleic acid is stably integrated into the cell line,
the fully-deleted Adenoviral vector construct comprises LITR, Ψ, and RITR from Adenovirus, a gene expression construct, a subset of an Adenovirus late region coding sequence under control of one or more transcriptional activators, and human genomic stuffer DNA, and
no packaging construct is present.

22. The system of claim 6 wherein:
the Adenovirus packaging cell line comprises a first nucleic acid having an Adenovirus early region 1 (E1) coding sequence and a repressor gene coding sequence; and a second nucleic acid having an Adenovirus late region coding sequence or a subset thereof under control of a repressible promoter and an Adenovirus pIX coding sequence, wherein each nucleic acid is stably integrated into the cell line,
the fully-deleted Adenoviral vector construct comprises LITR, Ψ, and RITR from Adenovirus, a gene expression construct, and human genomic stuffer DNA, and
no packaging construct is present.

23. The system of claim 6 wherein:
the Adenovirus packaging cell line comprises a first nucleic acid having an Adenovirus early region 1 (E1) coding sequence, an Adenovirus pIX coding sequence under control of a repressible promoter, and a repressor gene coding sequence; and a second nucleic acid having an Adenovirus late region coding sequence or a subset thereof under control of a repressible promoter, wherein each nucleic acid is stably integrated into the cell line,
the fully-deleted Adenoviral vector construct comprises LITR, Ψ, and RITR from Adenovirus, a gene expression construct, and human genomic stuffer DNA, and
no packaging construct is present.

24. The system of claim 6 wherein:
the Adenovirus packaging cell line comprises a first nucleic acid having an Adenovirus early region 1 (E1) coding sequence and a repressor gene coding sequence; and a second nucleic acid having an Adenovirus late region coding sequence or a subset thereof under control of a repressible promoter, an Adenovirus pIX coding sequence, a non-Adenoviral early coding sequence under control of an inducible promoter, and a non-Adenoviral origin of replication (ori), wherein each nucleic acid is stably integrated into the cell line,
the fully-deleted Adenoviral vector construct comprises LITR, Ψ, and RITR from Adenovirus, a gene expression construct, a transcriptional activator, and human genomic stuffer DNA, and
no packaging construct is present.

25. The system of claim 6 wherein:
the Adenovirus packaging cell line comprises a first nucleic acid having an Adenovirus early region 1 (E1) coding sequence, an Adenovirus pIX coding sequence, and a repressor gene coding sequence; and a second nucleic acid having an Adenovirus late region coding sequence or a subset thereof under control of a repressible promoter, a non-Adenoviral early coding sequence under control of an inducible promoter, and a non-Adenoviral origin of replication (ori), wherein each nucleic acid is stably integrated into the cell line,
the fully-deleted Adenoviral vector construct comprises LITR, Ψ, and RITR from Adenovirus, a gene expression construct, a transcriptional activator, and human genomic stuffer DNA, and
no packaging construct is present.

* * * * *

UNITED STATES PATENT AND TRADEMARK OFFICE
CERTIFICATE OF CORRECTION

PATENT NO. : 9,719,107 B2
APPLICATION NO. : 14/921421
DATED : August 1, 2017
INVENTOR(S) : Miles B. Brennan et al.

It is certified that error appears in the above-identified patent and that said Letters Patent is hereby corrected as shown below:

On the Title Page

(72) Inventors, last inventor: replace "Xianghua Zhang, Auroroa, CO (US)" with Xianghua Zhang, Aurora, CO (US).

Signed and Sealed this
Thirty-first Day of July, 2018

Andrei Iancu
*Director of the United States Patent and Trademark Office*